(12) United States Patent
Bornarth et al.

(10) Patent No.: US 10,024,863 B2
(45) Date of Patent: Jul. 17, 2018

(54) METHODS FOR DYE SELECTION FOR PROTEIN MELT TEMPERATURE DETERMINATIONS

(71) Applicant: LIFE TECHNOLOGIES CORPORATION, Carlsbad, CA (US)

(72) Inventors: Carole Bornarth, Fremont, CA (US); Mousumi Rath, San Ramon, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 14/213,204

(22) Filed: Mar. 14, 2014

(65) Prior Publication Data

US 2014/0315190 A1    Oct. 23, 2014

Related U.S. Application Data

(60) Provisional application No. 61/789,334, filed on Mar. 15, 2013.

(51) Int. Cl.
| | |
|---|---|
| *G01N 33/557* | (2006.01) |
| *G01N 33/58* | (2006.01) |
| *G01N 33/68* | (2006.01) |
| *C09B 23/10* | (2006.01) |
| *C09B 23/14* | (2006.01) |

(52) U.S. Cl.
CPC .......... *G01N 33/582* (2013.01); *C09B 23/10* (2013.01); *C09B 23/105* (2013.01); *C09B 23/107* (2013.01); *C09B 23/145* (2013.01); *G01N 33/6803* (2013.01)

(58) Field of Classification Search
CPC .. G01N 33/582; G01N 33/6803; C09B 23/10; C09B 23/105; C09B 23/107; C09B 23/145
See application file for complete search history.

(56) References Cited

U.S. PATENT DOCUMENTS

| | | | | |
|---|---|---|---|---|
| 5,616,502 A | * | 4/1997 | Haugland | ........ G01N 27/44726 |
| | | | | 422/504 |
| 6,020,141 A | | 2/2000 | Pantoliano et al. | |
| 6,162,616 A | | 12/2000 | Shyjan | |
| 2011/0130305 A1 | * | 6/2011 | Patton | ................... C09B 23/141 |
| | | | | 506/15 |

FOREIGN PATENT DOCUMENTS

| | | |
|---|---|---|
| WO | WO1997/042500 | 11/1997 |
| WO | WO1999/024050 | 5/1999 |
| WO | WO-2002/026891 | 4/2002 |
| WO | WO-2011/065980 | 6/2011 |
| WO | WO-2014/144360 | 9/2014 |

OTHER PUBLICATIONS

Brown et al., "Use of Nile Red as a long-wavelength fluorophore in dual-probe studies of ligand-protein interactions.", *Journal of Fluorescence*, vol. 3, No. 3, Sep. 1993, 129-130.
Ericsson et al., "Thermofluor-based high-throughput stability optimization of proteins for structural studies", *Analytical Biochemistry*, vol. 357, No. 2, Oct. 15, 2006, 289-298.
Intl Application No. PCT/US2014/028736, International Search Report and Written Opinion dated Sep. 15, 2014, 1-16.
Lavinder et al., "High-throughput thermal scanning: a general, rapid dye-binding thermal shift screen for protein engineering", *Journal of the American Chemical Society*, vol. 131, No. 11, Mar. 25, 2009, 3794-3795.
PCT/US2014/028736 International Preliminary Report on Patentability dated Sep. 24, 2015.

* cited by examiner

*Primary Examiner* — Shafiqul Haq

(57) ABSTRACT

According to the present teachings, compositions, kits, and methods for protein melt analysis are provided that utilizing one or more fluorophore dyes. In some embodiments, a method comprises preparing a sample by mixing at least one protein with two or more dyes, and applying a controlled heating, while recording the fluorescence emission of the sample. The methods can be used, for example, for screening conditions for optimized protein stability, screening for ligands that bind and enhance protein stability (e.g., protein-protein interactions), screening for mutations for enhanced stability, screening crystallization conditions for protein stability, screening storage conditions for protein stability, and screening conditions in which a protein will be used (e.g., production conditions, treatment conditions, etc.) for protein stability.

22 Claims, 35 Drawing Sheets

METHODS FOR DYE SELECTION FOR PROTEIN MELT TEMPERATURE DETERMINATIONS

CROSS-REFERENCE TO RELATED APPLICATIONS

This application claims the benefit under 35 U.S.C. 119(e) of U.S. Provisional Application No. 61/789,334, filed Mar. 15, 2013 (LT00681 PRO), the contents of which is incorporated herein by reference in its entirety.

BACKGROUND

Proteins are typically the key molecule studied as the drug target for drug development generation. High throughput screening of small-molecule and ligand libraries that bind to protein targets is an important part of the process—requiring screening of thousands of small molecules and ligands with a variety of different assays. This screening can require months of time. Protein targets are challenging to work with due to their susceptibility to degradation and aggregation, so protein stability screening is often an important component of lead generation programs. Protein stability screening, performed using the protein melting method, is employed in other research programs that involve native proteins. Protein melting is an extremely useful screening method for the identification of ligands and/or solution (buffer) conditions that maximally stabilize a protein as part of protein purification, crystallization, and functional characterization. The use of fluorescence techniques to monitor protein unfolding is well known to those of ordinary skill in the art. For example, see Eftink, M. R., Biophysical J. 66: 482-501 (1994).

Historically, the methodologies to perform protein melt screening are either very slow and tedious, analyzing one sample at a time—or if high-throughput, require milligram amounts of protein sample and incur high costs in either reagents, or protein samples, or both. It would be useful to have new and useful systems, methods and reagents to screen proteins, including antibodies, to identify ligands, mutations/modifications, buffer conditions, or other factors that affect their melting temperature ($T_m$) and relative stability.

SUMMARY OF THE DISCLOSURE

Various embodiments of systems and methods for protein melt analysis according to the present teachings provide for the determination of protein melt temperature ($T_m$) using mixtures of dyes. The methods may include Protein Thermal Shift (PTS) assays. The methods involve functionally classifying a protein that is capable of unfolding due to a thermal change. The methods may involve screening a ligand, buffer conditions, mutations, and/or crystallization conditions for their ability to shift the thermal unfolding curve of the protein alone or in the presence of a binding partner. The methods may involve screening one or more conditions (e.g., buffer, etc.) during use, storage and/or crystallization of one or more proteins for the ability to stabilize the protein(s) as measured by a shift the thermal unfolding curve of the protein in the presence of the one or more conditions. A shift in the thermal unfolding curve indicates that the molecule binds to the protein or affects the stability in a measurable way, generating an activity spectrum for the protein wherein the activity spectrum reflects a change in the stability as affected by the binding partner and/or buffer. The methods can involve the identification of the best fluorophore dye or dye mixtures for use in determining the protein melt temperature. In at least one embodiment, the methods involve the use of at least two dyes and/or a mixture of dyes (e.g., a SYPRO® orange, SYPRO® Red, and SYPRO® Tangerine mixture). The one or more proteins may include a protein/ligand pair, a protein/antibody pair, a protein/protein pair, etc.

In one aspect, the invention provides a method for measuring the stability of at least one protein, by forming a sample solution mixture including at least one protein and a mixture of at least two fluorophore dyes, applying controlled heating to the mixture; and measuring fluorescence emitted over a temperature range. In certain embodiments, the sample solution mixture may be formed when the at least one protein is in its native state. In various embodiments, when the at least one protein is present in its native state, then each of the at least two fluorophore dyes may be configured to provide at least a minimally fluorescent signal and when the at least one protein is present in an unfolded state, then each of the at least two fluorophore dyes may be configured to provide a substantially increased fluorescent signal. In some embodiments, each of the at least two fluorophore dyes may be spectrally distinct. In some embodiments, the at least minimally fluorescent signal of at least one of the at least two fluorophore dyes may be a nonfluorescent signal. In some embodiments, the measuring step may be performed in the presence of a filter. In various embodiments, the filter may have an excitation filter of 580±10 nm and an emission filter of 623±14 nm. In other embodiments, the filter may have an excitation filter of 640±10 nm and an emission filter of 680±14 nm. In various embodiments, at least one of the mixture of at least two fluorophore dyes may be Nile Red. In some embodiments, at least one of the mixture of at least two fluorophore dyes may be a styryl dye.

In various embodiments, the styryl dye may have a structure of the formula Q-B-M, where Q is a quaternized nitrogen heterocycle having a quaternizing group TAIL; B is a covalent bridge that is an ethenyl or polyethenyl bridging moiety, and M is an aromatic heterocyclic moiety or activated methylene moiety. In some embodiments, the styryl dye of formula Q-B-M may have a structure of formula $Q_a$-B-$M_a$; where $Q_a$ has a structure of the formula:

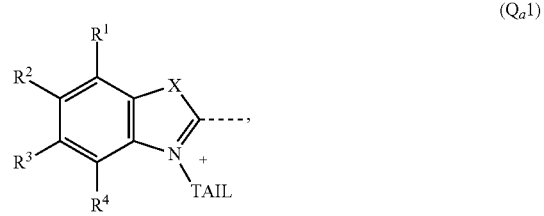

($Q_a$1)

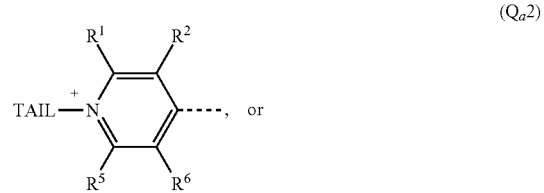

($Q_a$2)

, or

-continued

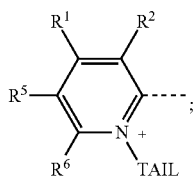

(Q$_a$3)

X is —S—, —O—, —NR$^7$—, or —CR$^7$R$^8$; R$^7$ and R$^8$ are optionally and independently H, Cl, F, phenyl, or C$_1$-C$_6$ alkyl; or R$^7$ and R$^8$ taken in combination form a 5- or 6-membered saturated ring; R$^1$ and R$^2$ are optionally and independently H, Cl, F, sulfo, carboxy, salt of sulfo, salt of carboxy, C$_1$-C$_6$ alkyl or C$_1$-C$_6$ alkoxy; or R$^1$ and R$^2$, when taken in combination, form a fused 6-membered aromatic ring that is optionally further substituted one or more times by H, Cl, F, C$_1$-C$_6$ alkyl or C$_1$-C$_6$ alkoxy, carboxy, sulfo or salts of carboxy or sulfo; R$^3$, R$^4$, R$^5$, and R$^6$ are optionally and independently H, Cl, F, C$_1$-C$_6$ alkyl or C$_1$-C$_6$ alkoxy; or any two adjacent R$^3$, R$^4$, R$^5$ and R$^6$, when taken in combination, form a fused 6-membered aromatic ring that is optionally further substituted one or more times by H, Cl, F, C$_1$-C$_6$ alkyl or C$_1$-C$_6$ alkoxy, carboxy, sulfo or salts of carboxy or sulfo; TAIL is attached to the nitrogen atom of Q$_a$ through a carbon atom and contains a total of 1-22 non-hydrogen atoms, where the non-hydrogen atoms are selected from the group consisting of C, O, N or S, such that within TAIL each heteroatom is separated from any adjacent heteroatoms by at least two carbon atoms, and further where TAIL is composed of bonds selected from the group consisting of carbon-carbon bonds (C—C), ether bonds (C—O—C), thioether bonds (C—S—C) or amine bonds (C—NR$^9$—C); where any carbon atom in TAIL is optionally further substituted by hydroxy, carboxy, sulfo, amino, or ammonium, and where any amine bond, amino or ammonium in TAIL is optionally substituted by an R$^9$ that is C$_2$-C$_6$ alkyl optionally further substituted by hydroxy, carboxy, sulfo, amino, amino substituted by 1-2 C$_1$-C$_6$ alkyls or ammonium substituted by 1-3 C$_1$-C$_6$ alkyls; or the nitrogen atoms of TAIL form either one or two saturated 5- or 6-membered rings in combination with other C or N atoms in TAIL; B has a structure of the formula —(CR$^7$=CR$^8$)$_n$—; where n is an integer of 1-3, M$_a$ has a structure of the formula:

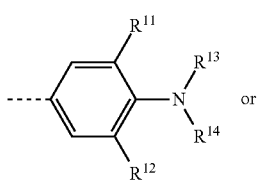

(M$_a$1)

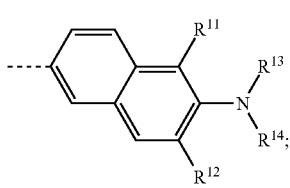

(M$_a$2)

R$^{11}$ and R$^{12}$ are independently H, F, Cl, or —CH$_3$; the ring substituents not specified are hydrogen; R$^{13}$ and R$^{14}$ are independently C$_1$-C$_8$ alkyls that are linear, branched, saturated or unsaturated, and are optionally substituted one or more times by F, hydroxy or C$_1$-C$_6$ alkoxy; or R$^{13}$ and R$^{14}$, when taken in combination, form a 5- or 6-membered saturated ring that contains 0 or 1 oxygen heteroatom; or R$^{11}$ taken in combination with R$^{13}$ and R$^{14}$ taken in combination with R$^{12}$ are independently —(CH$_2$)$_2$— or —(CH$_2$)$_3$—.

In some embodiments, the styryl dye of formula Q-B-M has a structure of formula Q$_b$-B-M$_b$;

where Q$_b$ has a structure of one of the following formulae:

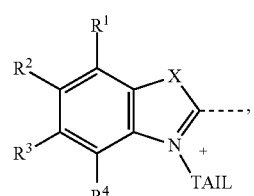

(Q$_b$1)

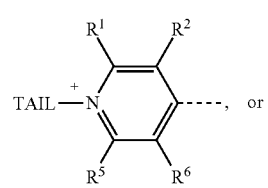

(Q$_b$2)

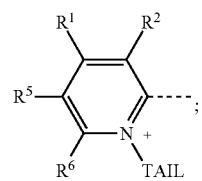

(Q$_b$3)

where X is —S—, —O—, —NR$^7$—, or —CR$^7$R$^8$; R$^7$ and R$^8$ are independently H, Cl, F, phenyl, or C$_1$-C$_6$ alkyl; or R$^7$ and R$^8$ taken in combination form a 5- or 6-membered saturated ring; R$^1$ and R$^2$ are independently H, Cl, F, sulfo, carboxy, salt of sulfo, salt of carboxy, C$_1$-C$_6$ alkyl or C$_1$-C$_6$ alkoxy; or R$^1$ and R$^2$, when taken in combination, form a fused 6-membered aromatic ring optionally further substituted one or more times by H, Cl, F, C$_1$-C$_6$ alkyl or C$_1$-C$_6$ alkoxy, carboxy, sulfo or salts of carboxy or sulfo; R$^3$, R$^4$, R$^5$, and R$^6$ are independently H, Cl, F, C$_1$-C$_6$ alkyl or C$_1$-C$_6$ alkoxy; or any two adjacent substituents of R$^3$, R$^4$, R$^5$ and R$^6$, when taken in combination, form a fused 6-membered aromatic ring optionally further substituted one or more times by H, Cl, F, C$_1$-C$_6$ alkyl or C$_1$-C$_6$ alkoxy, carboxy, sulfo or salts of carboxy or sulfo;

TAIL is attached to the nitrogen atom of Q$_b$ through a carbon atom and is —(CH$_2$)$_m$SO$_3$— or —(CH$_2$)$_m$CO$_2^-$, m=1 to 6, and the negative charge is balanced by a positive charge on the nitrogen heterocycle Q$_b$; or TAIL is —(CH$_2$)$_m$NR$_a$R$_b$ or —(CH$_2$)$_m$N$^+$R$_a$R$_b$R$_c$, where R$_a$, R$_b$ and R$_c$, which may be the same or different, are H or C$_1$-C$_6$ alkyl or R$_a$ and R$_b$ taken in combination form a 3-6 membered ring, optionally containing a heteroatom that is O, NR$_d$ or S, where R$_d$ is H or C$_1$-C$_6$ alkyl; B has the formula —(CH=CH)$_n$—, where n has a value of 1-3; M$_b$ has a structure of the formula:

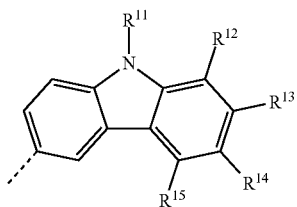

where $R^{11}$ is $C_1$-$C_6$ alkyl, phenyl, or phenyl substituted one or more times by H, Cl, F, $C_1$-$C_6$ alkyl or $C_1$-$C_6$-alkoxy; and $R^{12}$, $R^{13}$, $R^{14}$ and $R^{15}$ are H, Cl, F, $C_1$-$C_6$ alkyl or $C_1$-$C_6$ alkoxy. In some embodiments, the mixture of at least two of fluorophore dyes may include Nile Red and a styryl dye.

In other embodiments, the step of measuring the fluorescence emission may measure fluorescence from each of the at least two fluorophore dyes. In some embodiments, the method may include calculating a $T_m$ of the at least one protein using the measured fluorescence.

In various embodiments, the sample solution mixture may include a ligand which is configured to form a protein/ligand complex with the at least one protein. In some embodiments, the protein/ligand complex is an antibody/antigen complex. In various embodiments, the ligand may be a peptide, a polynucleotide, or an aptamer.

In various embodiments, the method may include the steps of performing the steps of forming a sample solution mixture including at least one protein and a mixture of at least two fluorophore dyes, applying controlled heating to the mixture; and measuring fluorescence emitted over a temperature range, and calculating a $T_m$ of the at least one protein using the measured fluorescence when the sample solution mixture contains only the at least one protein; and forming a sample solution mixture including at least one protein and a mixture of at least two fluorophore dyes, applying controlled heating to the mixture; and measuring fluorescence emitted over a temperature range, and calculating a $T_m$ of the at least one protein using the measured fluorescence when the sample solution mixture contains the at least one protein and a ligand in a protein/ligand complex; comparing the $T_m$ obtained for the at least one protein alone and the $T_m$ obtained for the at least one protein and ligand; and thereby analyzing the change in stability upon forming the protein/ligand complex with the at least one protein.

In various embodiments, the controlled heating may be a thermal ramp. In some embodiments, the thermal ramp may be from about 20° C. to about 95° C. In other embodiments, the controlled heating may be isothermal heating.

In various embodiments, the sample solution mixture may further include a buffer. In other embodiments, the sample solution mixture may further include a surfactant. In some embodiments, the surfactant may be present at a concentration that is at least the critical micelle concentration. In some other embodiments, the sample solution mixture may further include a polyol. In some embodiments, the polyol may be glycerol. In other embodiments, the polyol may be a polysaccharide.

In various embodiments, the method further includes the steps of calculating a first $T_m$ from the measured fluorescence obtained from the at least one protein and the mixture of at least two fluorophore dyes wherein the sample solution mixture comprises a first buffer; calculating a second $T_m$ from the measured fluorescence obtained from the at least one protein and the mixture of at least two fluorophore dyes wherein the sample solution mixture comprises a second buffer, and comparing the first $T_m$ and the second $T_m$, thereby analyzing the stability of the at least one protein in the presence of the first buffer compared to the stability obtained in the presence of the second buffer. In various embodiments, the method further includes analyzing the stability of the at least one protein under conditions used for crystallization of the protein.

In another aspect of the invention, a composition is provided including at least one protein, and a mixture of at least two fluorophore dyes, where each of the at least two fluorophore dyes is configured to provide at least a minimally fluorescent signal when the at least one protein is present in its native state and when the at least one protein is present in an unfolded state, then each of the at least two fluorophore dyes is configured to provide a substantially increased fluorescent signal. In some embodiments, each of the at least two fluorophore dyes may be spectrally distinct from each other. In various embodiments, one of the at least two fluorophore dyes may be Nile Red. In some embodiments, one of the at least two fluorophore dyes may be a styryl dye.

In various embodiments, the styryl dye of the composition may have a structure of the formula Q-B-M, where Q is a quaternized nitrogen heterocycle having a quaternizing group TAIL; B is a covalent bridge that is an ethenyl or polyethenyl bridging moiety, and M is an aromatic heterocyclic moiety or activated methylene moiety. In some embodiments, the styryl dye of formula Q-B-M may have a structure of formula $Q_a$-B-$M_a$; where $Q_a$ has a structure of the formula:

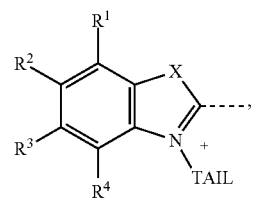

(Q$_a$1)

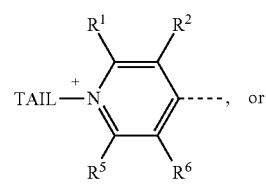

(Q$_a$2)

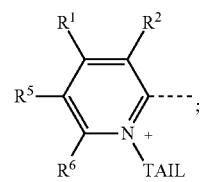

(Q$_a$3)

X is —S—, —O—, —NR$^7$—, or —CR$^7$R$^8$; R$^7$ and R$^8$ are optionally and independently H, Cl, F, phenyl, or $C_1$-$C_6$ alkyl; or R$^7$ and R$^8$ taken in combination form a 5- or 6-membered saturated ring; R$^1$ and R$^2$ are optionally and independently H, Cl, F, sulfo, carboxy, salt of sulfo, salt of carboxy, $C_1$-$C_6$ alkyl or $C_1$-$C_6$ alkoxy; or R$^1$ and R$^2$, when taken in combination, form a fused 6-membered aromatic ring that is optionally further substituted one or more times by H, Cl, F, $C_1$-$C_6$ alkyl or $C_1$-$C_6$ alkoxy, carboxy, sulfo or salts of carboxy or sulfo; $R^3$, $R^4$, $R^5$, and $R^6$ are optionally and independently H, Cl, F, $C_1$-$C_6$ alkyl or $C_1$-$C_6$ alkoxy; or any two adjacent $R^3$, $R^4$, $R^5$ and $R^6$, when taken in combination, form a fused 6-membered aromatic ring that is optionally further substituted one or more times by H, Cl, F, $C_1$-$C_6$ alkyl or $C_1$-$C_6$ alkoxy, carboxy, sulfo or salts of carboxy or sulfo; TAIL is attached to the nitrogen atom of $Q_a$ through a carbon atom and contains a total of 1-22 non-hydrogen atoms, where the non-hydrogen atoms are selected from the group consisting of C, O, N or S, such that within TAIL each heteroatom is separated from any adjacent heteroatoms by at least two carbon atoms, and further where TAIL is composed of bonds selected from the group consisting of carbon-carbon bonds (C—C), ether bonds (C—O—C), thioether bonds (C—S—C) or amine bonds (C—$NR^9$—C); where any carbon atom in TAIL is optionally further substituted by hydroxy, carboxy, sulfo, amino, or ammonium, and where any amine bond, amino or ammonium in TAIL is optionally substituted by an $R^9$ that is $C_2$-$C_6$ alkyl optionally further substituted by hydroxy, carboxy, sulfo, amino, amino substituted by 1-2 $C_1$-$C_6$ alkyls or ammonium substituted by 1-3 $C_1$-$C_6$ alkyls; or the nitrogen atoms of TAIL form either one or two saturated 5- or 6-membered rings in combination with other C or N atoms in TAIL; B has a structure of the formula —$(CR^7$=$R^8)_n$—; where n is an integer of 1-3, $M_a$ has a structure of the formula:

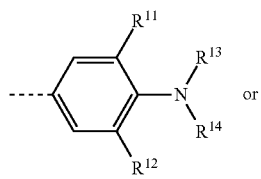

(M$_a$1)

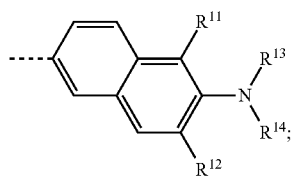

(M$_a$2)

$R^{11}$ and $R^{12}$ are independently H, F, Cl, or —$CH_3$; the ring substituents not specified are hydrogen; $R^{13}$ and $R^{14}$ are independently $C_1$-$C_8$ alkyls that are linear, branched, saturated or unsaturated, and are optionally substituted one or more times by F, hydroxy or $C_1$-$C_6$ alkoxy; or $R^{13}$ and $R^{14}$, when taken in combination, form a 5- or 6-membered saturated ring that contains 0 or 1 oxygen heteroatom; or $R^1$ taken in combination with $R^{13}$ and $R^{14}$ taken in combination with $R^{12}$ are independently —$(CH_2)_2$— or —$(CH_2)_3$—.

In some embodiments, the styryl dye of formula Q-B-M has a structure of formula $Q_b$-B-$M_b$;

where $Q_b$ has a structure of one of the following formulae:

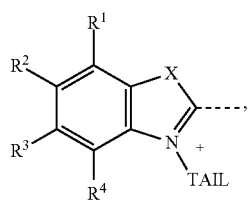

(Q$_b$1)

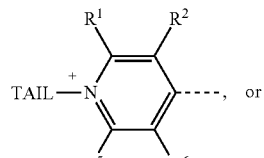

(Q$_b$2)

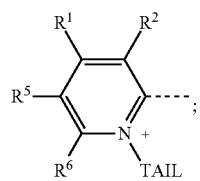

(Q$_b$3)

where X is —S—, —O—, —$NR^7$—, or —$CR^7R^8$; $R^7$ and $R^8$ are independently H, Cl, F, phenyl, or $C_1$-$C_6$ alkyl; or $R^7$ and $R^8$ taken in combination form a 5- or 6-membered saturated ring; $R^1$ and $R^2$ are independently H, Cl, F, sulfo, carboxy, salt of sulfo, salt of carboxy, $C_1$-$C_6$ alkyl or $C_1$-$C_6$ alkoxy; or $R^1$ and $R^2$, when taken in combination, form a fused 6-membered aromatic ring optionally further substituted one or more times by H, Cl, F, $C_1$-$C_6$ alkyl or $C_1$-$C_6$ alkoxy, carboxy, sulfo or salts of carboxy or sulfo; $R^3$, $R^4$, $R^5$, and $R^6$ are independently H, Cl, F, $C_1$-$C_6$ alkyl or $C_1$-$C_6$ alkoxy; or any two adjacent substituents of $R^3$, $R^4$, $R^5$ and $R^6$, when taken in combination, form a fused 6-membered aromatic ring optionally further substituted one or more times by H, Cl, F, $C_1$-$C_6$ alkyl or $C_1$-$C_6$ alkoxy, carboxy, sulfo or salts of carboxy or sulfo;

TAIL is attached to the nitrogen atom of $Q_b$ through a carbon atom and is —$(CH_2)_mSO_3^-$ or —$(CH_2)_mCO_2^-$, m=1 to 6, and the negative charge is balanced by a positive charge on the nitrogen heterocycle $Q_b$; or TAIL is —$(CH_2)_mNR_aR_b$ or —$(CH_2)_mN^+R_aR_bR_c$, where $R_a$, $R_b$ and $R_b$, which may be the same or different, are H or $C_1$-$C_6$ alkyl or $R_a$ and $R_b$ taken in combination form a 3-6 membered ring, optionally containing a heteroatom that is O, $NR_d$ or S, where $R_d$ is H or $C_1$-$C_6$ alkyl; B has the formula —(CH=CH)$_n$—, where n has a value of 1-3; $M_b$ has a structure of the formula:

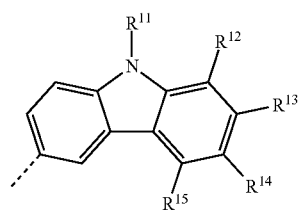

M$_b$ where $R^{11}$ is $C_1$-$C_6$ alkyl, phenyl, or phenyl substituted one or more times by H, Cl, F, $C_1$-$C_6$ alkyl or $C_1$-$C_6$-alkoxy; and $R^{12}$, $R^{13}$, $R^{14}$ and $R^{15}$ are H, Cl, F, $C_1$-$C_6$alkyl or $C_1$-$C_6$ alkoxy. In some embodiments, the mixture of at least two of fluorophore dyes may include Nile Red and a styryl dye.

In some embodiments, the at least one protein of the composition may further include a protein/ligand complex. In other embodiments, the protein/ligand complex may be an antibody/antigen complex. In some embodiments, the ligand may be a peptide, a polynucleotide, or an aptamer. In various embodiments, the composition may further include one or more of a buffer, a surfactant, or a polyol.

In yet another aspect of the invention, a kit is provided which includes a composition including at least two fluorophore dyes, where each of the at least two fluorophore dyes is configured to provide at least a minimally fluorescent signal when at least one protein is in its native state and when the at least one protein is present in an unfolded state, then each of the at least two fluorophore dyes is configured to provide a substantially increased fluorescent signal. In various embodiments, each of the at least two fluorophore dyes may be spectrally distinct from each other. In other embodiments, one of the at least two fluorophore dyes may be Nile Red. In some embodiments, one of the at least two fluorophore dyes may be a styryl dye.

In various embodiments, the styryl dye of the kit may have a structure of the formula Q-B-M, where Q is a quaternized nitrogen heterocycle having a quaternizing group TAIL; B is a covalent bridge that is an ethenyl or polyethenyl bridging moiety, and M is an aromatic heterocyclic moiety or activated methylene moiety. In some embodiments, the styryl dye of formula Q-B-M may have a structure of formula $Q_a$-B-$M_a$; where $Q_a$ has a structure of the formula:

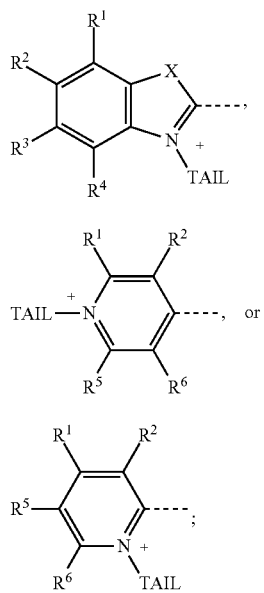

X is —S—, —O—, —$NR^7$—, or —$CR^7R^8$; $R^7$ and $R^8$ are optionally and independently H, Cl, F, phenyl, or $C_1$-$C_6$ alkyl; or $R^7$ and $R^8$ taken in combination form a 5- or 6-membered saturated ring; $R^1$ and $R^2$ are optionally and independently H, Cl, F, sulfo, carboxy, salt of sulfo, salt of carboxy, $C_1$-$C_6$ alkyl or $C_1$-$C_6$ alkoxy; or $R^1$ and $R^2$, when taken in combination, form a fused 6-membered aromatic ring that is optionally further substituted one or more times by H, Cl, F, $C_1$-$C_6$ alkyl or $C_1$-$C_6$ alkoxy, carboxy, sulfo or salts of carboxy or sulfo; $R^3$, $R^4$, $R^5$, and $R^6$ are optionally and independently H, Cl, F, $C_1$-$C_6$ alkyl or $C_1$-$C_6$ alkoxy; or any two adjacent $R^3$, $R^4$, $R^5$ and $R^6$, when taken in combination, form a fused 6-membered aromatic ring that is optionally further substituted one or more times by H, Cl, F, $C_1$-$C_6$ alkyl or $C_1$-$C_6$ alkoxy, carboxy, sulfo or salts of carboxy or sulfo; TAIL is attached to the nitrogen atom of $Q_a$ through a carbon atom and contains a total of 1-22 non-hydrogen atoms, where the non-hydrogen atoms are selected from the group consisting of C, O, N or S, such that within TAIL each heteroatom is separated from any adjacent heteroatoms by at least two carbon atoms, and further where TAIL is composed of bonds selected from the group consisting of carbon-carbon bonds (C—C), ether bonds (C—O—C), thioether bonds (C—S—C) or amine bonds (C—$NR^9$—C); where any carbon atom in TAIL is optionally further substituted by hydroxy, carboxy, sulfo, amino, or ammonium, and where any amine bond, amino or ammonium in TAIL is optionally substituted by an $R^9$ that is $C_2$-$C_6$ alkyl optionally further substituted by hydroxy, carboxy, sulfo, amino, amino substituted by 1-2 $C_1$-$C_6$ alkyls or ammonium substituted by 1-3 $C_1$-$C_6$ alkyls; or the nitrogen atoms of TAIL form either one or two saturated 5- or 6-membered rings in combination with other C or N atoms in TAIL; B has a structure of the formula —$(CR^7$=$CR^8)_n$—; where n is an integer of 1-3, $M_a$ has a structure of the formula:

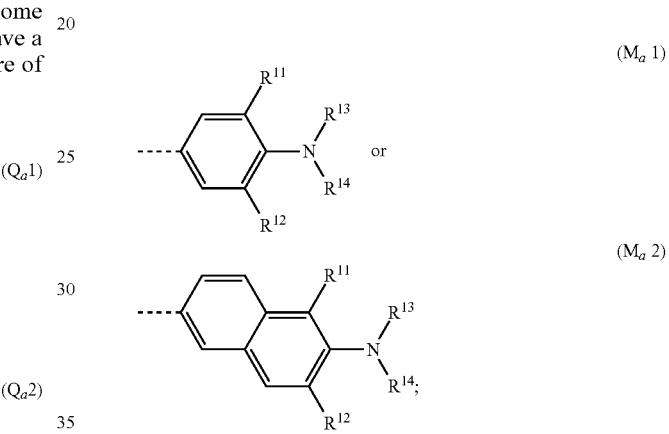

$R^{11}$ and $R^{12}$ are independently H, F, Cl, or —$CH_3$; the ring substituents not specified are hydrogen; $R^{13}$ and $R^{14}$ are independently $C_1$-$C_8$ alkyls that are linear, branched, saturated or unsaturated, and are optionally substituted one or more times by F, hydroxy or $C_1$-$C_6$ alkoxy; or $R^{13}$ and $R^{14}$, when taken in combination, form a 5- or 6-membered saturated ring that contains 0 or 1 oxygen heteroatom; or $R^{11}$ taken in combination with $R^{13}$ and $R^{14}$ taken in combination with $R^{12}$ are independently —$(CH_2)_2$— or —$(CH_2)_3$—.

In some embodiments, the styryl dye of formula Q-B-M has a structure of formula $Q_b$-B-$M_b$;

where $Q_b$ has a structure of one of the following formulae:

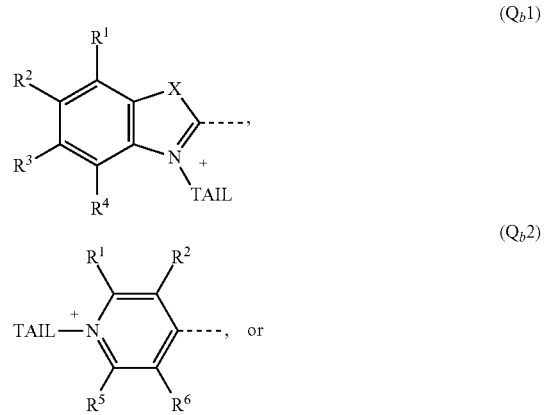

-continued

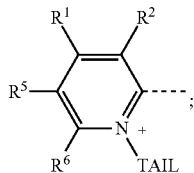

(Q$_b$3)

where X is —S—, —O—, —NR$^7$—, or —CR$^7$R$^8$; R$^7$ and R$^8$ are independently H, Cl, F, phenyl, or C$_1$-C$_6$ alkyl; or R$^7$ and R$^8$ taken in combination form a 5- or 6-membered saturated ring; R$^1$ and R$^2$ are independently H, Cl, F, sulfo, carboxy, salt of sulfo, salt of carboxy, C$_1$-C$_6$ alkyl or C$_1$-C$_6$ alkoxy; or R$^1$ and R$^2$, when taken in combination, form a fused 6-membered aromatic ring optionally further substituted one or more times by H, Cl, F, C$_1$-C$_6$ alkyl or C$_1$-C$_6$ alkoxy, carboxy, sulfo or salts of carboxy or sulfo; R$^3$, R$^4$, R$^5$, and R$^6$ are independently H, Cl, F, C$_1$-C$_6$ alkyl or C$_1$-C$_6$ alkoxy; or any two adjacent substituents of R$^3$, R$^4$, R$^5$ and R$^6$, when taken in combination, form a fused 6-membered aromatic ring optionally further substituted one or more times by H, Cl, F, C$_1$-C$_6$ alkyl or C$_1$-C$_6$ alkoxy, carboxy, sulfo or salts of carboxy or sulfo;

TAIL is attached to the nitrogen atom of Q$_b$ through a carbon atom and is —(CH$_2$)$_m$SO3$^-$ or —(CH$_2$)$_m$CO$_2^-$, m=1 to 6, and the negative charge is balanced by a positive charge on the nitrogen heterocycle Q$_b$; or TAIL is —(CH$_2$)$_m$NR$_a$R$_b$ or —(CH$_2$)$_m$N$^+$R$_a$R$_b$R$_c$, where R$_a$, R$_b$ and R$_c$, which may be the same or different, are H or C$_1$-C$_6$ alkyl or R$_a$ and R$_b$ taken in combination form a 3-6 membered ring, optionally containing a heteroatom that is O, NR$_d$ or S, where R$_d$ is H or C$_1$-C$_6$ alkyl; B has the formula —(CH=CH)$_n$—, where n has a value of 1-3; M$_b$ has a structure of the formula:

M$_b$

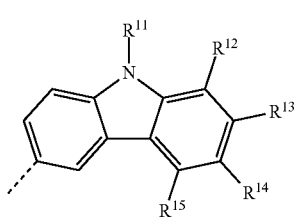

where R$^{11}$ is C$_1$-C$_6$ alkyl, phenyl, or phenyl substituted one or more times by H, Cl, F, C$_1$-C$_6$ alkyl or C$_1$-C$_6$-alkoxy; and R$^{12}$, R$^{13}$, R$^{14}$ and R$^{15}$ are H, Cl, F, C$_1$-C$_6$alkyl or C$_1$-C$_6$ alkoxy. In some embodiments, the mixture of at least two of fluorophore dyes may include Nile Red and a styryl dye.

In various embodiments, the kit may further include one or more one or more of a buffer, a surfactant, or a polyol.

BRIEF DESCRIPTION OF THE DRAWINGS

FIG. 2A is a melt curve with normalized reporter. FIG. 2B shows the first derivative graph of the PTS of FIG. 2A.

FIG. 3A shows a melt curve of three mutated proteins. FIG. 3B shows the first derivative graph of the PTS of FIG. 3A. FIG. 3C shows a melt curve of the three mutated proteins complexed with an oligonucleotide.

FIG. 4A shows the melt curve with normalized reporter. FIG. 4B shows the first derivative graph of the PTS of FIG. 4A.

FIGS. 6A and 6B are melt curves of PTS data for human plasma using SYPRO® Red in comparison to SYPRO® Orange.

FIGS. 8A through 8D shows PTS of membrane proteins using a variety of dyes as comparison according to various embodiments of systems and methods of the present teachings.

DETAILED DESCRIPTION

Figure 1:
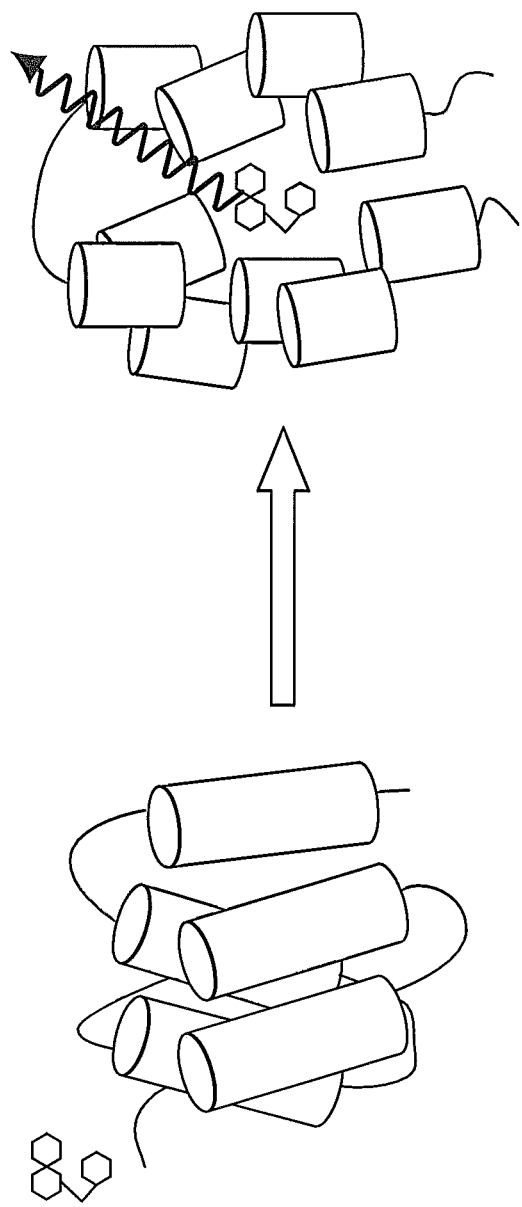
FIG. 1 is a schematic of the predicted behavior of SYPRO® Orange dye according to various embodiments of systems and methods of the present teachings.

The present teachings relate to embodiments of systems and methods providing fluorophore dye selection for optimizing protein melt temperature determinations such as protein thermal shift assays (PTS). The methods involve forming a sample solution mixture, where the sample solution mixture includes at least one protein and at least one fluorophore dye, applying a controlled heating to the mixture, and measuring the fluorescence emitted over a temperature range. Other methods involve forming a sample solution mixture of at least one protein and a mixture of at least two fluorophore dyes.

It has been discovered that mixtures of at least two fluorophore dyes provide surprisingly improved ability to study protein thermal melt performance. Depending on the nature of the folded protein, the use of a single dye may provide a high background to the melt curve. However, using mixtures of dyes, decreased background can be obtained. Additionally, when attempting to sturdy proteins with multiphasic melts, clear differentiation may be possible, using the methods described herein to arrive at optimized dye mixtures and filters. Much greater detail of the unfolding events may be evident using the methods and compositions described herein.

The methods can be used to screen buffer conditions for optimized protein stability. The methods can be used to screen for ligands that bind to and enhance protein stability. The methods can be used to screen through point mutations for those that result in enhanced stability. The methods can be used to screen for conditions that enhance stability for protein crystallization, storage and/or use of the proteins. The methods can further include optimizing the dye choice by using one or a mixture of at least two fluorophore dyes depending on the protein or protein mixtures being used in a PTS assay. In some embodiments, the methods can further include optimizing the dye choice by a mixture of at least two fluorophore dyes depending on the protein or protein mixtures being used in a PTS assay.

The Protein Thermal Shift (PTS) Assay is a high-throughput screening method which enables researchers to rapidly monitor protein thermo-stability and to identify optimal conditions that favor protein stability, including the investigation of protein-ligand interactions and mutations in protein sequences. Protein Thermal Shift is based on temperature-induced protein denaturation, monitored using an environmentally sensitive dye, such as SYPRO® Orange. The PTS assay does not require any prior knowledge of protein function or ligand activity. These methods may be used with any suitable instrument capable of delivering controlled heat and recording the spectrally distinct fluorescence of the mixture of one or more fluorophore dyes. Any instruments capable of delivering controlled heat and recording the fluorescence can be used, including, but not limited to, Applied Biosystems' Real-time PCR Systems. In at least one embodiment, the protein of interest is analyzed within a test buffer environment to identify buffers that increase the stability of the protein or proteins. In at least one embodiment, the protein of interest is analyzed in the presence of a test ligand to identify whether the ligand increases the stability of the protein of interest. The methods allow for comparison of fluorescence and/or $T_m$ values obtained using a range of buffer conditions, addition of different ligands, or protein sequence mutations that alter protein folding and stability. In Example 1, the utility of this assay using protein thermal shift (PTS) in buffer and ligand screening for T4 DNA ligase is demonstrated by the observed shift in the $T_m$ of T4 DNA ligase in the presence of ATP. Further embodiments show the use of Protein Thermal Shift Assays as screening tools for X-ray crystallographers looking for conditions that promote the stability of their protein of interest. In addition, the utility of the PTS Assay to discriminate between point mutation variants of M-MLV. SuperScript®II and SuperScript®III Reverse-Transcriptase is demonstrated in Example 4. Further, the examples demonstrate that the PTS assay can effectively detect the binding of antibodies to the target protein (see Example 5).

Thus, methods and systems are provided herein to identify the best dyes (optimized dyes) for a specific PTS analysis of one or more proteins, a protein/ligand, a complex mixture of proteins, membrane proteins and/or for specific conditions (e.g., buffers, surfactants and/or polyols). The dyes may be used alone or in combination. Various combinations of dyes may be used in the methods of the invention to identify a single fluorophore dye or specific combinations of fluorophore dyes which provide the best melting curve for analysis of protein folding for a specific protein under any of the conditions described herein. Further methods are provided for using mixtures of dyes in PTS methods. Further methods are provided for screening conditions for optimized protein stability, screening for ligands that bind and enhance protein stability (e.g., protein-protein interactions and/or protein-ligand interactions), screening for mutations for enhanced stability, screening crystallization conditions for protein stability, screening storage conditions for protein stability, and screening conditions in which a protein will be used (e.g., production conditions, treatment conditions, etc.) for protein stability.

As used herein, "substituted" refers to a molecule wherein one or more hydrogen atoms are replaced with one or more non-hydrogen atoms, functional groups or moieties. For example an exemplary unsubstituted ethenyl group may be represented —CH=CH—. Substituted ethenyl groups may include, for example, but are not limited by, —CH=CH—COOH, —CH=CHCOOR, —CH=CH-Aryl and —CH=CH-Aryl-OR where, for example, R is alkyl or substituted alkyl. As one of ordinary skill in the art is apprised, for a variety of organic dye molecules, some non-limiting exemplary substituents include: halogen, alkyl, cycloalkyl, branched alkyl, alkene, cyclic alkene, branched alkene, alkyne, branched alkyne, carboxyl, ester, sulfate, sulfonate, sulfone, amino, ammnonium, amido, nitrile, alkoxy, phenoxy, phenyl, polycyclic aromatic, and electron-rich heterocycle. As will be discussed in more detail subsequently, non-limiting examples of substituents for various embodiments of dyes of the present teachings may include halogen, acid, ester, cycloakyl, alkyl, aryl, heteroaryl, arylalkyl, alkenyl, azido, alkynyl, and sulfo; alone or in combination. Such substituents by themselves may be substituted by non-limiting examples such as halogen, alkyl, cyano, carboxylate ester, carboxamide, aryl, or heteroaryl. In the instances where substituents are described specifically in the following sections, the detailed description substitution patterns will control.

"Native" as used herein, refers to the folded and/or assembled form of a protein, which is operative and functional. A mutated protein, while having an altered structure and, optionally, an altered functionality and/or operability relative to a parent, non-mutated protein, has its own respective native state under the conditions of the methods described here and may also demonstrate a melt curve that can be mathematically derivatized to find a $T_m$ for the mutated protein.

"Ligand" as used herein, refers to a biomolecule or a synthetic organic molecule that may interact with the at least one protein in the methods described here. The ligand may be of any suitable class. In some embodiments, the at least one protein is an antibody and the ligand is an antigen, which interact to form an antibody/antigen complex. In other embodiments, the at least one protein interacts with a ligand which is a second protein. In yet other embodiments, the ligand that interacts with the at least one protein is a peptide, polynucleotide, or an aptamer. In other embodiments, the ligand is a synthetic organic molecule which may be capable of interacting with the at least one protein to stabilize or destabilize the protein. In some embodiments, the ligand that is a synthetic organic molecule interacts with the at least one protein to modify the normal function of the at least one protein.

The term "unfolding" refers to the loss of structure, such as crystalline ordering of amino acid side-chains, secondary, tertiary, or quaternary protein structure.

The term s "folding," "refolding," and "renaturing" refer to the acquisition of the correct amino acid side-chain ordering, secondary, tertiary, or quaternary structure, of a protein, which affords the full chemical and biological function of the biomolecule.

An "unfolding curve" is a plot of the physical change associated with the unfolding of a protein as a function temperature, denaturant concentration, pressure, etc. A "denaturation curve" is a plot of the physical change associated with the denaturation of a protein or a nucleic acid as a function of temperature, denaturant concentration, pressure, etc. A "thermal unfolding curve" is a plot of the physical change associated with the unfolding of a protein or a nucleic acid as a function of temperature. A "thermal denaturation curve" is a plot of the physical change associated with the denaturation of a protein or a nucleic acid as a function of temperature. See, for example, Davidson et al., Nature Structure Biology 2: 859 (1995); and Clegg, R. M. et al., Proc. Natl. Acad. Sci. US. A. 90: 2994-2998 (1993).

The term "shift in the thermal unfolding curve" refers to a displacement relative to observed temperature (for a thermal ramp) or time (for isothermal heating) of the amount of fluorescence measured in the thermal unfolding curve for a protein that is: a) bound to a ligand, relative to the thermal unfolding curve of the protein in the absence of the ligand; b) a protein subjected to the thermal unfolding methods described here where buffer, surfactant or polyol conditions differ; c) different dye mixtures are used; or d) different mutated proteins are subjected to the thermal unfolding methods.

The term "modification of stability" refers to the change in the amount of pressure, the amount of heat, the concentration of detergent, or the concentration of denaturant that is required to cause a given degree of physical change in a target protein that is bound by one or more ligands, relative to the amount of pressure, the amount of heat, the concentration of detergent, or the concentration of denaturant that is required to cause the same degree of physical change in the target protein in the absence of any ligand. Modification of stability can be exhibited as an increase or a decrease in stability. Modification of the stability of a protein by a ligand indicates that the ligand binds to the protein. Modification of the stability of a protein by more than one ligand indicates that the ligands bind to the protein.

The term "modification of thermal stability" refers to the change in the amount of thermal energy that is required to cause a given degree of physical change in a target protein that is bound by one or more ligands, relative to the amount of thermal energy that is required to cause the same degree of physical change in the target protein in the absence of any ligand. Modification of thermal stability can be exhibited as an increase or a decrease in thermal stability.

Modification of the thermal stability of a protein by a ligand indicates that the ligand binds to the protein. Modification of the thermal stability of a protein by more than one ligand indicates that the ligands bind to the protein.

The "midpoint temperature, $T_m$" or melting temperature is the temperature midpoint of a thermal unfolding curve. The $T_m$ can be readily determined using methods well known to those skilled in the art. See, for example, Weber. P. C. et al., J. Am. Chem. Soc. 116: 2717-2724 (1994); and Clegg, R. M. et al. Proc. Natl. Acad. Sci. U.S.A 90: 2994-2998 (1993).

As discussed above, it is preferable to determine the effect of one or more molecules on the thermal stability of a target protein according to a change in the T of the thermal unfolding curve for the protein. Alternatively the effect of one or more molecules on the thermal stability of a target protein can be determined according to the change in entire thermal unfolding curve for the target protein.

The term "fluorophore dye" refers to an extrinsic fluorophore, which is a fluorescent molecule or a compound which is capable of associating with at least one unfolded or denatured protein or ligand/protein complex of interest and, after excitement by light of a defined wavelength, emits fluorescent energy. Further, a fluorophore dye useful for the methods described herein does not fluoresce or provides a minimally fluorescent signal when present in a composition containing at least one protein or ligand/protein complex of interest where the at least one protein or ligand/protein complex is in its native or folded state. "Minimally fluorescent" refers to a fluorescence signal that may be not measurably above background or it may be measurably fluorescent but does not obscure the measurement of the fluorescence emission increase provided upon unfolding of the at least one protein with subsequent access to increased hydrophobic environment by the fluorophore dye or dyes. A fluorophore dye useful for the methods provides a substantially increased fluorescence emission when the least one protein in the sample solution mixture unfolds. "Substantially increased" refers to an increased fluorescence signal measured as the at least one protein unfolds and the environment in the sample solution mixture permits the fluorophore dye or dyes to fluoresce. A substantially increased fluorescence signal will provide a thermal melt curve that is capable of mathematical derivation to provide a $T_m$ for the at least one protein.

As used herein, the term "spectrally distinct" refers to the ability to detect each of the at least two fluorophore dyes independently from each other. As recognized in the art, many fluorophore dyes have emission spectra permitting selective detection of each dye when used in a combination of several dyes. One of skill in the art may select a combination of dyes that have emission spectral properties that permit differentiable detection of each of the combination of fluorophore dyes.

Protein Thermal Shift (PTS) Assay.

Protein Thermal Shift is a rapid tool for screening of suitable conditions that maximize protein stability. Methods of providing fluorophore dye selection for optimizing protein melt temperature determinations such as protein thermal shift assays (PTS) are provided. The methods involve forming a sample solution mixture, where the sample solution mixture includes at least one protein (e.g., a protein of interest) and a mixture of at least two fluorophore dyes, applying a controlled heating to the mixture, and measuring the fluorescence emitted over a temperature range. In at least one embodiment, the at least one protein is in its native state. When the protein or proteins are in their native state, the fluorophore dye or dyes in the sample solution mixture are configured to provide a minimally fluorescent signal or a nonfluorescent signal. Further, when the protein or proteins are present in the unfolded state in the sample solution mixture, the fluorophores are configured to provide a substantially increased fluorescent signal. The fluorophore dye is chosen based on these characteristics. Any fluorophore dye that has these characteristics alone or in combination with another fluorescent dye can be used in the methods. In at least one embodiment, one of the dyes is nonfluorescent under aqueous conditions, but is fluorescent under more hydrophobic conditions such as may exist when the dye is present in the sample solution mixture and exposed to an unfolded protein's hydrophobic regions. In at least one embodiment, when more than one fluorophore dye is included, the dyes are spectrally distinct.

The use of a non-specific fluorophore dye, such as SYPRO® Orange, alleviates any requirement for prior knowledge of protein function or ligand activity in an assay. In the presence of a native protein, this type of dye is naturally quenched due to its exposure to a primarily aqueous environment, in which it provides a minimally or non-fluorescent signal. When the protein of interest starts to denature in response to, for example, an increase in temperature, the hydrophobic core of the protein is exposed. The fluorophore dye will react to this change in environment and will start to fluoresce (see FIG. 1).

Currently available PTS applications use SYPRO® Orange which provides adequate results for many simple protein folding/unfolding experiments. However, in the case of multiple proteins, complex protein mixtures, membrane proteins, or proteins with external regions of hydrophobicity, the PTS melt curve can have a high background, due to protein/protein interactions or interactions of fluorophore dye with external moieties of the protein. In these cases, alternate dyes or dye mixtures can improve the curve shape, reduce background and improve the resolution of the curve so that a $T_m$ or multiple $T_m$ s can be observed and calculated. In addition, some proteins may melt in multiple phases. Changing the PTS dye or using multiple dyes can improve visualization of these complex melt profiles.

Suitable fluorophore dyes may be selected from a wide variety of dye structures.

One diverse group of dyes suitable for use herein are styryl dyes that includes a quaternary nitrogen heterocycle linked to an electron pair-donating moiety by an alkylene or polyalkylene bridge. A wide variety of electron pair-donating groups are known that stabilize the formally positive charge of the quaternary nitrogen heterocycle by resonance. Suitable electron pair-donating groups include, but are not limited to dialkylaminophenyl, dialkylaminonaphthyl, electron-rich heterocycles and acyclic moieties containing electron pair-donating groups.

Styryl dyes useful in the methods, compositions and kits described herein have a structure of Formula I:

Q-B-M                                    (Formula I)

wherein Q is a quaternized nitrogen heterocycle having a quaternizing group TAIL; B is a covalent bridge that is an ethenyl or polyethenyl bridging moiety, and M is an aromatic heterocyclic moiety or activated methylene moiety.

The quaternizing moiety. TAIL, is attached to the nitrogen atom of Q through a carbon atom and contains a total of 1-22 non-hydrogen atoms, wherein the non-hydrogen atoms are selected from the group consisting of C, O, N or S, such that within TAIL each heteroatom is separated from any adjacent heteroatoms by at least two carbon atoms. TAIL is composed of bonds that are selected from the group consisting of carbon-carbon bonds (C—C), ether bonds (C—O—C), thioether bonds (C—S—C) or amine bonds (C—NR—C). Any carbon atom in TAIL is optionally further substituted by hydroxy, carboxy, sulfo, amino, or ammonium. Any amine bond, amino or ammonium in TAIL is optionally substituted by an $R^9$ that is $C_2$-$C_6$ alkyl that is optionally further substituted by hydroxy, carboxy, sulfo, amino, amino substituted by 1-2 $C_1$-$C_6$ alkyls or ammonium substituted by 1-3 $C_1$-$C_6$ alkyls. Alternatively, the nitrogen atoms of TAIL form either one or two saturated 5- or 6-membered rings in combination with other C or N atoms in TAIL, such that the resulting rings are pyrrolidines, piperidines, piperazines or morpholines.

The covalent bridge, B, has the formula:

—(CR$^7$=CR$^8$)$_n$—, wherein $R^7$ and $R^8$ are optionally and independently H, Cl, F, or $C_1$-$C_6$ alkyl; alternatively, $R^7$ and $R^8$ taken in combination complete a 5- or 6-membered saturated ring (—(CH$_2$)$_4$— or —(CH$_2$)$_5$—). The subscript n has a value of 1-3, and determines how many conjugated alkenyl moieties are joined to form the bridge. The spectral properties of the resulting dye are highly dependent upon the length of the bridge moiety, with the excitation and emission wavelengths shifting to longer wavelengths with the addition of each alkenyl moiety.

Depiction of the instant dyes herein does not differentiate between cis and trans isomers; that is, isomers that differ only in the stereo chemistry of the ethylenyl moieties of B. It is to be understood that, except where expressly stated, the compounds implicitly include the cis isomer, the trans isomer, or a mixture thereof.

In some embodiments, a styryl dye of Formula Q-B-M, is a merocyanine dye suitable for use as a fluorophore dye as described herein and is described by the general formula:

$Q_a$-B-$M_a$

The quaternized nitrogen heterocycle $Q_a$ has the formula:

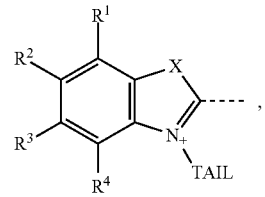

(Q$_a$1)

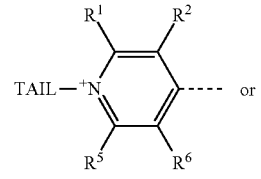

(Q$_a$2)

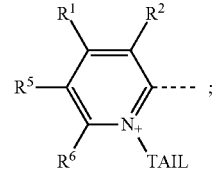

(Q$_a$3)

where the ring substituents $R^1$, $R^2$, $R^3$ and $R^4$ are optionally and independently H, Cl, F, $C_1$-$C_6$ alkyl, $C_1$-$C_6$ perfluoroalkyl, $C_1$-$C_6$ alkoxy, amino, or amino substituted by 1-2 $C_1$-$C_6$ alkyls. Alternatively, any two adjacent substituents of $R^1$, $R^2$, $R^3$ and $R^4$, when taken in combination, form a fused 6-membered aromatic ring that is optionally further substituted by Cl, F, $C_1$-$C_6$ alkyl, $C_1$-$C_6$ perfluoroalkyl, $C_1$-$C_6$ alkoxy, amino, or amino substituted by 1-2 $C_1$-$C_6$ alkyls. The ring substituents $R^5$ and $R^6$ are optionally and independently H, Cl, F, $C_1$-$C_6$ alkyl, $C_1$-$C_6$ perfluoroalkyl, $C_1$-$C_6$ alkoxy, amino, amino substituted by 1-2 $C_1$-$C_6$ alkyls, or phenyl, where the phenyl ring is optionally further substituted by Cl, F, $C_1$-$C_6$ alkyl, $C_1$-$C_6$ perfluoroalkyl, $C_1$-$C_6$ alkoxy, amino, or amino substituted by 1-2 $C_1$-$C_6$ alkyls. Alternatively, $R^5$ and $R^6$, when taken in combination, form a fused 6-membered aromatic ring (yielding a benzo-substituted pyridinium, or quinolinium moiety). The additional ring on the quinolinium that is thereby formed is optionally and independently substituted one or more times by Cl, F, $C_1$-$C_6$ alkyl, $C_1$-$C_6$ perfluoroalkyl, $C_1$-$C_6$ alkoxy, amino, or amino substituted by 1-2 $C_1$-$C_6$ alkyls. Additionally, the quinolinium ring is optionally substituted by an additional fused 6-membered aromatic ring (yielding a naphtho-substituted pyridinium, or a benzoquinoline), that is also optionally and independently substituted one or more times by Cl, F, $C_1$-$C_6$ alkyl, $C_1$-$C_6$ perfluoroalkyl, $C_1$-$C_6$ alkoxy, amino, or amino substituted by 1-2 $C_1$-$C_6$ alkyls. In some embodiments, $R^5$ and $R^6$ are H, or form a substituted or unsubstituted benzo moiety. In some other embodiments, $R^5$ and $R^6$, taken in combination, form a fused 6-membered substituted or unsubstituted benzo moiety yielding a quinolinium ring system.

In the benzazole ring $Q_a1$, the ring fragment X is optionally —S—, —O—, —$NR^7$—, or —$CR^7R^8$—, wherein $R^7$ and $R^8$ are optionally and independently H, Cl, F, or $C_1$-$C_6$ alkyl; alternatively, $R^7$ and $R^8$ taken in combination complete a 5- or 6-membered saturated ring (—$(CH_2)_4$— or —$(CH_2)_5$—). In some embodiments, where X is —$CR^7R^8$, $R^7$ and $R^8$ may be selected to be $CH_3$. In some embodiments, X is O or S. In certain embodiments, X is S.

The quaternizing moiety, TAIL, is attached to the nitrogen atom of $Q_a$ through a carbon atom and contains a total of 1-22 non-hydrogen atoms, wherein the non-hydrogen atoms are selected from the group consisting of C, O, N or S, such that within TAIL each heteroatom is separated from any adjacent heteroatoms by at least two carbon atoms. TAIL is composed of bonds that are selected from the group consisting of carbon-carbon bonds (C—C), ether bonds (C—O—C), thioether bonds (C—S—C) or amine bonds (C—NR—C). Any carbon atom in TAIL is optionally further substituted by hydroxy, carboxy, sulfo, amino, or ammonium. Any amine bond, amino or ammonium in TAIL is optionally substituted by $C_2$-$C_6$ allyl that is optionally further substituted by hydroxy, carboxy, sulfo, amino, amino substituted by 1-2 $C_1$-$C_6$ alkyls or ammonium substituted by 1-3 $C_1$-$C_6$ alkyls. Alternatively, the nitrogen atoms of TAIL form either one or two saturated 5- or 6-membered rings in combination with other C or N atoms in TAIL, such that the resulting rings are pyrrolidines, piperidines, piperazines or morpholines.

In one embodiment, the TAIL moiety includes at least one nitrogen heteroatom, wherein in some other embodiments, the nitrogen atom is a dialkylamino or a trialkylammonium substituent, and where the alkyl substituents are methyl or ethyl. In some embodiments, TAIL, is —$CH_3$, or $CH_2$ $CH_3$, or TAIL is a $C_3$-$C_{22}$ alkyl chain that is linear or branched, saturated or unsaturated, and that is optionally substituted one or more times by hydroxy, carboxy, sulfo, amino, amino substituted by 1-2 $C_1$-$C_6$alkyls, or ammonium substituted by 1-3 $C_1$-$C_6$ alkyls. By "sulfo" is meant sulfonic acid (—$SO_3H$) or the common alkali metal salts of sulfonic acid. More preferably, TAIL is a $C_3$-$C_{12}$ alkyl chain that is linear and saturated, and substituted at its free terminus by hydroxy, carboxy, sulfo, amino, amino substituted by 1-2 $C_1$-$C_6$ alkyls, or ammonium substituted by 1-3 $C_1$-$C_6$ alkyls. In other embodiments, the TAIL moiety is a $C_3$-$C_4$ alkyl that is substituted once by sulfo or carboxy.

The covalent bridge, B, has the formula:

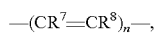

where $R^7$ and $R^8$ have been defined as previously. The subscript n has a value of 1-3, and determines how many conjugated alkenyl moieties are joined to form the bridge. The spectral properties of the resulting dye are highly dependent upon the length of the bridge moiety, with the excitation and emission wavelengths shifting to longer wavelengths with the addition of each alkenyl moiety. In some embodiments, $R^7$ and $R^8$ are both H. In some embodiments, n=1 or 2.

The moiety $M_a$ has the formula:

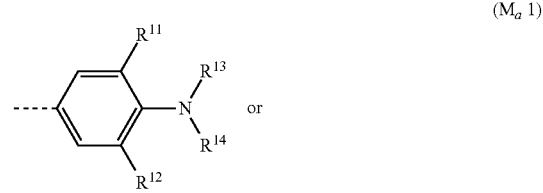

(M$_a$1)

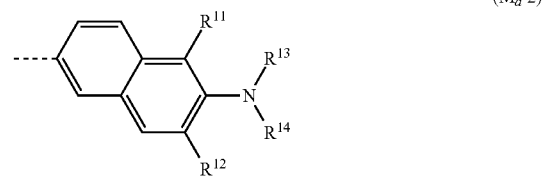

(M$_a$2)

where the ring substituents $R^{11}$ and $R^{12}$ are independently H, F, Cl, or —$CH_3$. In some embodiments, $R^1$ and $R^{12}$ are H. The other ring substituents not specified in formulae $M_a1$ or $M_a2$ are each hydrogen. The amino substituents $R^3$ and $R^{14}$ are independently $C_1$-$C_5$ alkyls that are linear, branched, saturated or unsaturated, and are optionally substituted one or more times by F, hydroxy or $C_1$-$C_6$ alkoxy. Alternatively, $R^3$ and $R^{14}$, when taken in combination, form a 5- or 6-membered saturated ring that optionally contains an oxygen heteroatom. In another embodiment of the dyes, $R^{11}$ taken in combination with $R^3$ and $R^{14}$ taken in combination with $R^{12}$ are independently —$(CH_2)_2$— or —$(CH_2)_3$—, forming 5- or 6-membered rings. In other embodiments, $R^{13}$ and $R^{14}$ are each linear alkyls, which may be the same or different, each having 4-8 carbon atoms, more preferably each having 5 to 7 carbon atoms.

Alternatively, the electron pair-donating moiety $M_a$ has the formula:

(M$_a$3)

(M$_a$4)

(M$_a$5)

Electron pair-donating moieties of formula $M_m3$ are acyclic, and are typically derivatives of malonic acid, cyanoacetic acid or malononitrile, while moieties of formula $M_a4$ or $M_a5$ are 5- and 6-membered heterocycles, respectively.

For all embodiments of $M_a$, Y is —OH, —SH, —O$^-$ or —S$^-$. In some embodiments, Y is —O$^-$ or —S$^-$. In other embodiments, Y is —O$^-$.

For the acyclic moiety $M_a3$, Z is —$OR^{15}$, —$SR^{15}$, —$N(R^{15})_2$, preferably —$OR^{15}$, where $R^{15}$ is H or $C_1$-$C_6$ alkyl. Where Z' is part of the heterocyclic rings of $M_a4$ and $M_a5$, Z' is one of —O—, —S—, or —$NR^{17}$—, where $R^{17}$ is H, $C_1$-$C_6$ alkyl, $C_1$-$C_6$ carboxyalkyl, phenyl or phenyl substituted by sulfo. In some embodiments, Z' is —O— or —$NR^{17}$—. In other embodiments, $R^{17}$ is alkyl, phenyl or phenyl substituted by sulfo. Where $R^{17}$ is phenyl substituted by sulfo, the sulfo may be at the para position of the phenyl ring.

W is a strong electron withdrawing group, and is one of CN, —(C═O)—$R^{16}$, or —(C═S)—$R^6$, preferably CN or —(C═O)—$R^{16}$, where $R^{16}$ is —$OR^{15}$, —$SR^{15}$, or —$N(R^{15})_2$, where $R^{is}$ is defined as above. In the 5-membered heterocyclic ring systems, W' is —O—, —S—, or —$NR^{17}$—, —(C═)—, —(C═S)— or —(C═$NR^1$)—, where $R^{17}$ is defined as above. In the 6-membered heterocyclic ring systems, W'' is —(C═)—, —(C═S)— or —(C═$NR^{17}$)—, where $R^{17}$ is defined as above.

The 5-membered ring fragment $R^{18}$ is one of —O—, —S—, or —$NR^{16}$—. Alternatively, W' and $R^{18}$, when taken in combination and in that order, form the fragment —$CR^{17}$═N—. In another alternative, Z' and $R^{18}$, when taken in combination and in that order, form the fragment —$CR^{17}$═N—. For both of these alternatives, $R^{17}$ may be alkyl, phenyl or phenyl substituted by sulfo, as above.

The 6-membered ring fragment $R^{19}$ is either —O—, —S—, or —$NR^{17}$—, where $R^{17}$ has been defined previously. The additional 6-membered ring fragment, L, is either —(C═O)—, —(C═S)— or —($CNR^{17}$)—. Additionally, W''' and $R^{19}$, when taken in combination and in that order, form the fragment —$CR^7$═N—.

In no embodiment of either the $M_a4$ or $M_a5$ moieties can the heterocycle contain ring segments that include O—O, S—S, O—S or N—N—N bonds.

Dyes that possess an electron pair-donating moiety having the formula $M_a3$, $M_a4$ or $M_a5$ are well known, and have been extensively described (Brooker et al., J. AM. CHEM. SOC. 73, 5326 (1951)). The description of these electron pair-donating moieties includes, but is not limited to, the specific dye fragments described in Table 1, where R is H, alkyl, carboxyalkyl, phenyl or sulfophenyl3

TABLE 1

Selected electron pair-donating moieties:

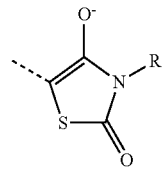

5-pyrazolone

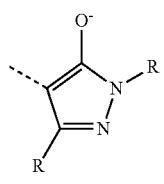

2-thiohydantoin

TABLE 1-continued

Selected electron pair-donating moieties:

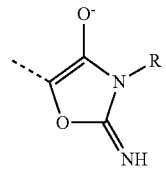

2,4,thiazolidinedione

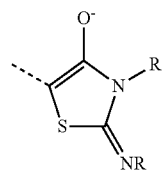

2-imino-4-oxazolone

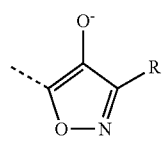

2-imino-4-thizaolidone

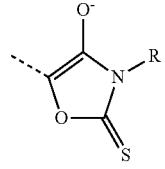

5(4H) isoxazolone

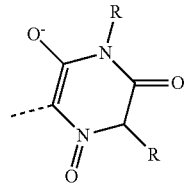

2-thio-2,4-oxazolidinedione

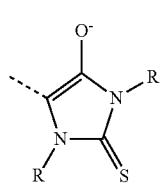

barbituric acid

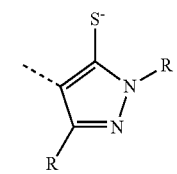

5-thiopyrazolone

TABLE 1-continued

Selected electron pair-donating moieties:

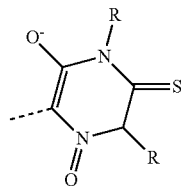

2-thiobarbituric acid

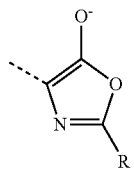

5(4H0-oxazolone

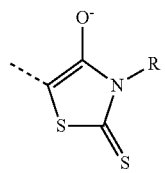

3-thio-2,4-thiazolidinedione

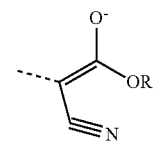

cyanoacetate

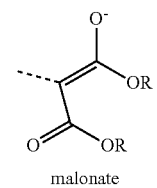

malonate

In some embodiments, a styryl dye of the formula $Q_a$-B-$M_a$ has a structure where $Q_a$ is a nitrogen heterocycle of the formula $Q_a1$, $Q_a2$, or $Q_a3$, where $R^1$, $R^2$, $R^3$ and $R^4$ are optionally and independently H, Cl, F, $C_1$-$C_6$ alkyl, $C_1$-$C_6$ perfluoroalkyl, $C_1$-$C_6$ alkoxy, amino or amino substituted by 1-2 $C_1$-$C_6$ alkyls; $R^5$ and $R^6$ are optionally and independently H, Cl, F, $C_1$-$C_6$ alkyl, $C_1$-$C_6$ perfluoroalkyl, $C_1$-$C_6$ alkoxy, amino, or amino substituted by 1-2 $C_1$-$C_6$ alkyls; or $R^5$ and $R^6$ taken in combination form a fused 6-membered aromatic ring that is optionally and independently substituted one or more times by Cl, F, $C_1$-$C_6$ alkyl, $C_1$-$C_6$ perfluoroalkyl, $C_1$-$C_6$ alkoxy, amino, amino substituted by 1-2 $C_1$-$C_6$ alkyls, or said fused 6-membered aromatic ring is optionally substituted by an additional fused 6-membered aromatic ring that is optionally and independently substituted by Cl, F, $C_1$-$C_6$ alkyl, $C_1$-$C_6$ perfluoroalkyl, $C_1$-$C_6$ alkoxy, amino, amino substituted by 1-2 $C_1$-$C_6$ alkyls; X is —S—, —O—, —NR$^7$—, or —CR$^7$R$^8$—, wherein R$^7$ and R$^8$ are optionally and independently H, Cl, F, phenyl, $C_1$-$C_6$ alkyl; or R$^7$ and R$^8$ taken in combination complete a 5- or 6-membered saturated ring; TAIL is attached to $Q_a$ through a carbon atom and contains 1-22 non-hydrogen atoms, wherein said non-hydrogen atoms are selected from the group consisting of C, O, N and S, such that each heteroatom is separated from any adjacent heteroatoms by at least two carbon atoms; and further such that TAIL is composed of carbon-carbon bonds (C—C), ether bonds (C—O—C), thio-ether bonds (C—S—C) or amine bonds (C—NR$^9$—C); where any carbon atom in TAIL is optionally further substituted by hydroxy, carboxy, sulfo, amino or ammonium; and where any amine bond, amino or ammonium in TAIL is optionally substituted by an R$^9$ that is a $C_2$-$C_6$ alkyl that is optionally further substituted by hydroxy, carboxy, sulfo, amino, amino substituted by 1-2 $C_1$-$C_6$ alkyls, or ammonium substituted by 1-3 $C_1$-$C_6$ alkyls, or said N atoms form either one or two saturated 5- or 6-membered rings in combination with additional C or N atoms in TAIL; B is a covalent bridge having the formula —(CR$^7$=CR$^8$)$_n$— where R$^7$ and R$^8$ are as defined previously; n=1, 2 or 3; and $M_a$ is an electron pair-donating moiety having a structure of $M_a1$ or $M_a2$, where R$^{11}$ and R$^{12}$ are independently H, F, Cl, or —CH$_3$; R$^{13}$ and R$^{14}$ are independently $C_1$-$C_{18}$ alkyl that is linear, branched, saturated or unsaturated, and is optionally substituted one or more times by F, hydroxy or $C_1$-$C_6$ alkoxy; or R$^{13}$ and R$^{14}$ taken in combination form a 5- or 6-membered saturated ring containing 0 or 1 oxygen heteroatoms; or R$^{13}$ taken in combination with R$^{11}$ and R$^{14}$ taken in combination with R$^{12}$ independently are —(CH$_2$)$_2$— or —(CH$_2$)$_3$—; or $M_a$ is of the formula $M_a3$, where Y is —OH, —SH, —O$^-$ or —S$^-$; Z is —OR$^{15}$, —SR$^{15}$, —N(R$^{15}$)$_2$; W is CN, —(C=O)—R$^{16}$, or —(C=S)—R$^{16}$; R$^{15}$ is H or $C_1$-$C_6$ alkyl; R$^{16}$ is —OR$^{15}$, —SR$^{15}$, —N(R$^{15}$)$_2$; or $M_a$ is of the formula $M_a4$ where Y is as defined previously; Z' is —O—, —S—, or —NR$^{17}$—; W' is —O—, —S—, —NR$^{17}$, —(C=O)—, —(C=S)—, or —(C=NR$^{17}$)—; R$^{17}$ is H, $C_1$-$C_6$ alkyl, $C_1$-$C_6$ carboxyalkyl, phenyl or phenyl substituted by sulfo; R$^{18}$ is —O—, —S—, —NR$^{17}$—, —(C=O)—, —(C=S)—, or —(C=NR$^{17}$)—; or W' and R$^{18}$ taken in combination are —CR$^{17}$=N—; or Z' and R$^{18}$ taken in combination are —CR$^{17}$=N—; or $M_a$ is of the formula $M_a5$, where Y and Z' are as defined previously; L is —(C=O)—, or —(C=S)—; R$^{19}$ is —O—, —S—, or =NR$^{17}$—; or W'' and R$^{19}$ taken in combination are —CR$^{17}$=N—; such that the resulting heterocycle does not include any O—O, S—S, O—S, or N—N—N bonds.

Another class of styryl dyes having a structure of formula Q-B-M, is a styryl dye having a structure of formula:

$Q_b$-B-$M_b$ where Qb$_a$ is a quaternized substituted or unsubstituted nitrogen heterocycle where the quaternizing group is a TAIL group. The quaternized nitrogen heterocycle $Q_b$ has a structure of one of the following formulae:

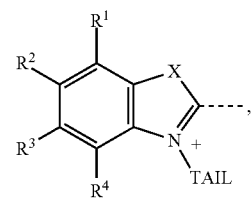

(Q$_b$1)

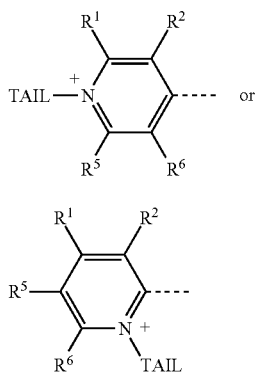

(Q$_b$2)

(Q$_b$3)

where X is —S—, —O—, —NR$^7$—, or —CR$^7$R$^8$, wherein R$^7$ and R$^8$ are optionally and independently H, Cl, F, phenyl, or C$_1$-C$_6$ alkyl; or R$^1$ and R$^8$ taken in combination complete a 5- or 6-membered saturated ring. The ring substituents R$^1$ and R$^2$ are optionally and independently H, Cl, F, sulfo, carboxy, salt of sulfo, salt of carboxy, C$_1$-C$_6$ alkyl or C$_1$-C$_6$ alkoxy. Alternatively, R$^1$ and R$^2$, when taken in combination, form a fused 6-membered aromatic ring that is optionally further substituted one or more times by H, Cl, F, C$_1$-C$_6$ alkyl or C$_1$-C$_6$ alkoxy, carboxy, sulfo or salts of carboxy or sulfo.

The substituents R$^3$, R$^4$, R$^5$, and R$^6$ are optionally and independently H, Cl, F, C$_1$-C$_6$ alkyl or C$_1$-C$_6$ alkoxy. Alternatively, any two adjacent substituents of R$^3$, R$^4$, R$^5$ and R$^6$, when taken in combination, form a fused 6-membered aromatic ring that is optionally further substituted one or more times by H, Cl, F, C$_1$-C$_6$ alkyl or C$_1$-C$_6$ alkoxy, carboxy, sulfo or salts of carboxy or sulfo. In some embodiments, a fluorophore dye is a TAIL-quaternized pyridinium, quinolinium or benzazolium dye. Where R$^5$ and R$^6$, taken in combination, form a fused 6-membered aromatic ring the resulting heterocycle is a benzo-substituted pyridinium, i.e. a quinolinium moiety. Any additional ring that is thereby formed is optionally and independently substituted one or more times by Cl, F, C$_1$-C$_6$ alkyl, C$_1$-C$_6$ alkoxy, carboxy, sulfo or salts of carboxy or sulfo. Typically, R$^5$ and R$^6$ are H, or form a substituted or unsubstituted benzo moiety. Preferably R$^5$ and R$^6$, taken in combination, form a fused 6-membered substituted or unsubstituted benzo moiety yielding a quinolinium ring system. Preferentially the quinolinium ring is unsubstituted or is substituted by sulfo or salts of sulfo.

The quaternizing moiety, TAIL, is attached to the nitrogen atom of Q$_b$ through a carbon atom and is either —(CH$_2$)$_m$SO$_3$$^-$ or —(CH$_2$)$_m$CO$_2$$^-$, where the subscript m=1 to 6 and the negative charge is balanced by a positive charge on the nitrogen heterocycle Q$_b$. Alternatively, TAIL is —(CH$_2$)$_m$NR$_a$R$_b$ or —(CH$_2$)$_m$N$^+$R$_a$R$_b$R$_c$, where R$_a$, R$_b$ and R$_c$, which may be the same or different, are H or C$_1$-C$_6$ alkyl or R$_a$ and R$_b$ taken in combination form a 3-6 membered ring, optionally containing a heteroatom that is O, NR$_d$ or S, where R$_d$ is H or C$_1$-C$_6$ alkyl. Any net positive charges on the dye are balanced by organic or inorganic anions. Typical inorganic anions include halides, nitrates, sulfates, phosphates and the like. Typical organic anions include carboxylates and aliphatic or aromatic sulfonates. Any net negative charges on the dye are balanced by organic or inorganic cations. Typical inorganic cations are ammonia or alkali or alkaline earth metals. Typical organic cations are ammonium or substituted ammonium salts.

The covalent bridge, B, has the formula —(CH=CH)$_n$—. The subscript n has a value of 1-3, and determines how many conjugated alkenyl moieties are joined to form the bridge. The spectral properties of the resulting dye are highly dependent upon the length of the bridge moiety, with the excitation and emission wavelengths shifting to longer wavelengths with the addition of each alkenyl moiety. In some embodiments, n=1 or 2.

The M$_b$ aromatic heterocyclic moiety is a carbazolyl moiety attached at its 3-position to covalent B, wherein M$_b$ has a structure of the formula:

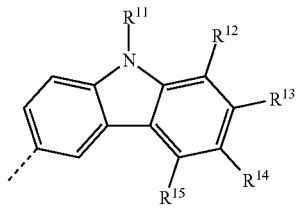

M$_b$ where R$^{11}$ is C$_1$-C$_6$ alkyl or is phenyl, or is phenyl substituted one or more times by H, Cl, F, C$_1$-C$_6$ alkyl or C$_1$-C$_6$-alkoxy. R$^{12}$, R$^{13}$, R$^{14}$ and R$^{15}$ are H, Cl, F, C$_1$-C$_6$ alkyl or C$_1$-C$_6$ alkoxy. Preferably all of R$^{12}$, R$^{13}$, R$^{14}$ and R$^{15}$ are H. In some embodiments, R$^{11}$ is methyl, ethyl or phenyl.

The TAIL-quaternized nitrogen heterocycle may be a TAIL-quaternized pyridine, quinoline or benzazole. However, carbazolylvinyl dyes that contain additional fused rings such as acridinium or phenanthridinium compounds, or wherein the pyridinium or quinolinium rings contain additional nitrogen atoms, such as azaquinolines, azabenzazoles or pyrimidines, may also be useful for the present invention provided that they selectively stain proteins when tested according to the protocols in the examples below. To obtain the proper charge delocalization in pyridines and quinolines, the point of attachment of the double bond on the quaternary nitrogen is either at the carbon atom immediately adjacent to the quaternary nitrogen atoms (e.g. 2-pyridiniums) or at a position removed from the quaternary nitrogen atom by a carbon-carbon double bond (e.g. 4-pyridiniums). In benzazolium dyes, the point of attachment is at the 2-position of the benzazolium ring. In some embodiments, all substituents on the TAIL-quaternized heterocycle other than on TAIL are H, although pyridinium, quinolinium and benzazolium dyes that optionally contain additional substituents that are lower alkyl, alkoxy, halogens, carboxy, or sulfo may be used to further tune the spectral properties of the dye to match a desired excitation or emission wavelength or to adjust the lipophilicity/hydrophilicity or other attributes of the dye. These can be prepared from appropriately substituted methylpyridines, methylquinolines, methylbenzazoles or other methyl-substituted nitrogen heterocycles.

In some embodiments, a dye of formula Q$_b$-B-M$_b$ is a compound where Q$_b$ is a nitrogen heterocycle having a structure of Q$_a$1, Q$_a$2, or Q$_a$3, wherein R$^1$ and R$^2$ are optionally and independently H, Cl, F, sulfo, carboxy, salt of sulfo, salt of carboxy, C$_1$-C$_6$ alkyl or C$_1$-C$_6$ alkoxy; or R$^1$ and R$^2$ taken in combination form a fused 6-membered aromatic ring that is itself optionally further substituted one or more times by H, Cl, F, C$_1$-C$_6$ alkyl or C$_1$-C$_6$ alkoxy, carboxy, sulfo or salts of carboxy or sulfo; R$^3$, R$^4$, R$^5$, and R$^6$ are optionally and independently H, Cl, F, $C_1$-$C_6$ alkyl or $C_1$-$C_6$ alkoxy; or any two adjacent substituents of $R^3$, $R^4$, $R^5$ and $R^6$, when taken in combination, form a fused 6-membered aromatic ring that is optionally and independently substituted one or more times by H, Cl, F, $C_1$-$C_6$ alkyl, $C_1$-$C_6$ alkoxy, carboxy, sulfo or salts of carboxy or sulfo; X is —S—, —O—, —NR'—, or —$CR^7R^8$, wherein $R^7$ and $R^8$ are optionally and independently H, Cl, F, phenyl, or $C_1$-$C_6$ alkyl; or $R^7$ and $R^8$ taken in combination complete a 5- or 6-membered saturated ring; TAIL is a quaternizing moiety that is attached to the nitrogen atom of Q through a carbon atom and is either —$(CH_2)_mSO_3^-$ or —$(CH_2)_mCO_2^-$, where the subscript m=1 to 6 and the negative charge is balanced by a positive charge on the nitrogen heterocycle Q; or TAIL is —$(CH_2)_mNR_aR_b$ or —$(CH_2)_mN^+R_aR_bR_c$, where $R_a$, $R_b$ and $R_c$, which may be the same or different, are H or $C_1$-$C_6$ alkyl or $R_a$ and $R_b$ taken in combination form a 3-6 membered ring, optionally containing a heteroatom that is O, $NR_d$ or S, where $R_d$ is H or $C_1$-$C_6$ alkyl; and wherein any net positive charges on the dye are balanced by organic or inorganic anions; B is a covalent bridge having the formula —(CH=CH)$_n$— where n=1, 2 or 3; and Z is carbazolyl moiety of the formula $_{Mb}$, where $^{R11}$ is $_{C1-C6}$ alkyl or is phenyl, or is phenyl substituted one or more times by H, Cl, F, $_{C1-C6}$ alkyl or $_{C1-C6}$ alkoxy; and $^{R12}$, $^{R13}$, $^{R14}$ and $^{R15}$ are H, Cl, F, $_{C1-C6}$ alkyl or, $_{C1-C6}$-alkoxy.

For all dyes of the invention, any net positive or negative charges possessed by the dye are balanced by a counterion or counterions. Where necessary, the counterion is depicted as Ψ and the polarity of the charge is indicated. Any of the common counterions currently used in conjunction with biomolecules is a suitable counterion for the dyes of the present invention. Examples of useful counterions for dyes having a net positive charge include, but are not limited to, chloride, bromide, iodide, sulfate, alkanesulfonate, arylsulfonate, phosphate, perchlorate, tetrafluoroborate, nitrate and anions of aromatic or aliphatic carboxylic acids. Preferred negative counterions are chloride, iodide, perchlorate and various sultanates. Examples of useful counterions for dyes having a net negative charge include, but are not limited to, alkali metal ions, alkaline earth metal ions, transition metal ions, ammonium or substituted ammonium ions.

TABLE 2

Selected useful dyes of the Formula $Q_a$—B—$M_a$ or $Q_b$—B—$M_b$ are shown.

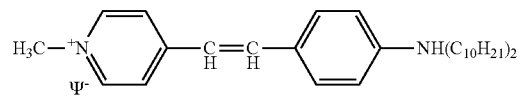

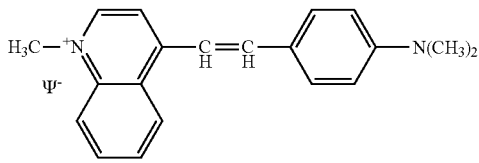

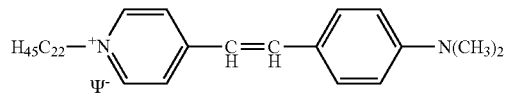

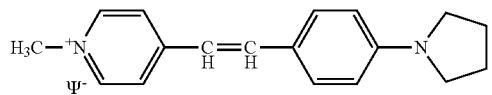

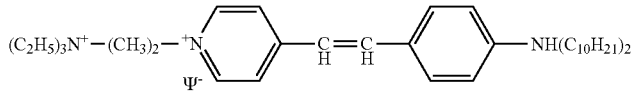

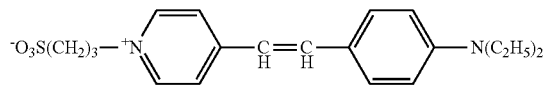

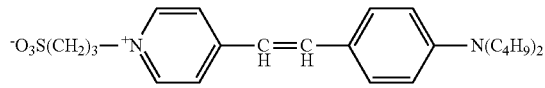

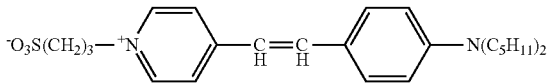

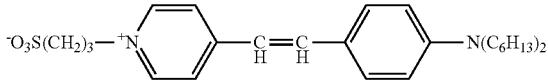

TABLE 2-continued
Selected useful dyes of the Formula Q$_a$—B—M$_a$ or Q$_b$—B—M$_b$ are shown.
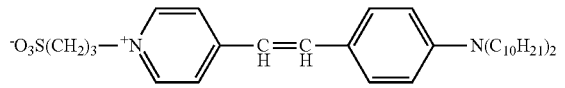
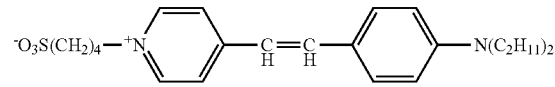
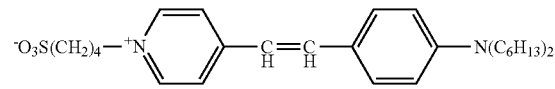
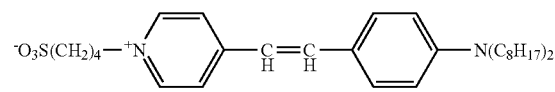
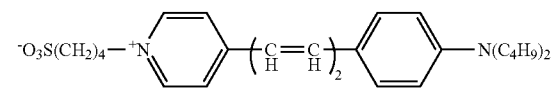
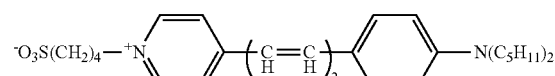
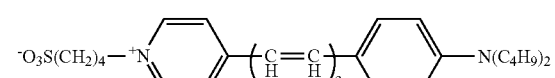
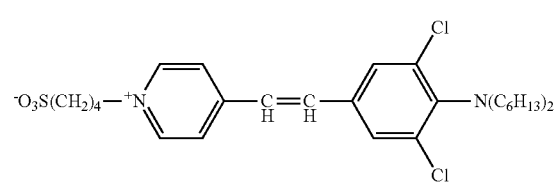
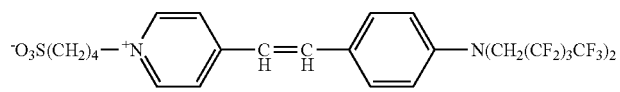
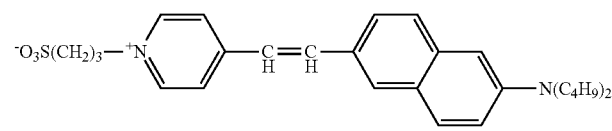
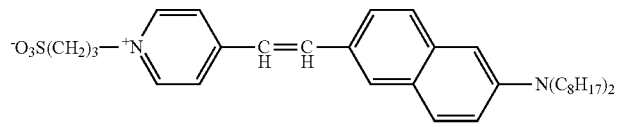
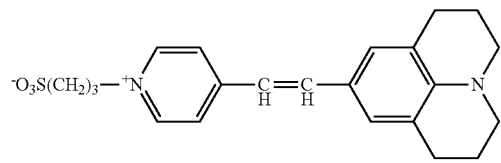
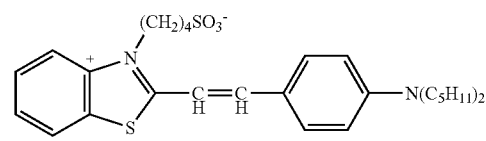

TABLE 2-continued
Selected useful dyes of the Formula $Q_a$—B—$M_a$ or $Q_b$—B—$M_b$ are shown.
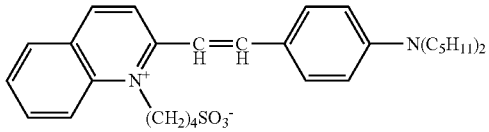
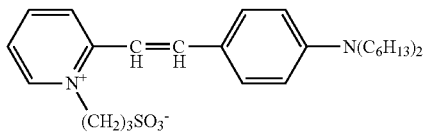
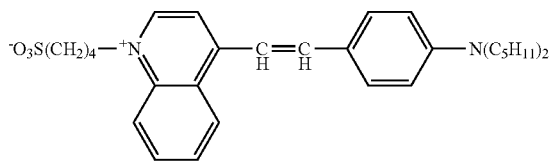
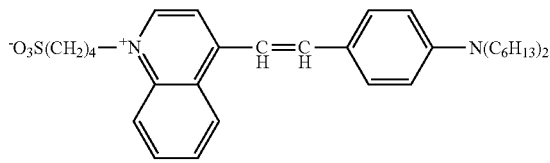
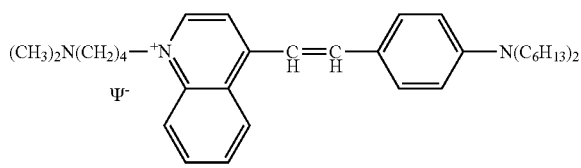
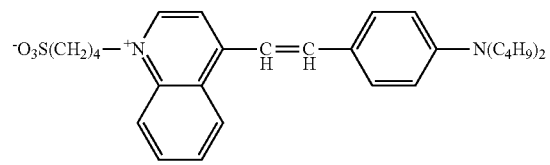
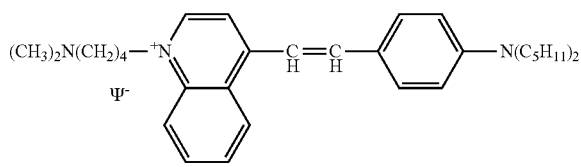
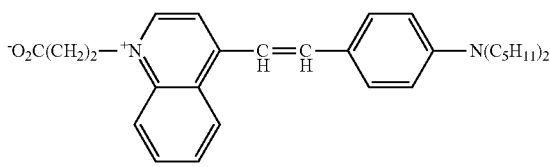
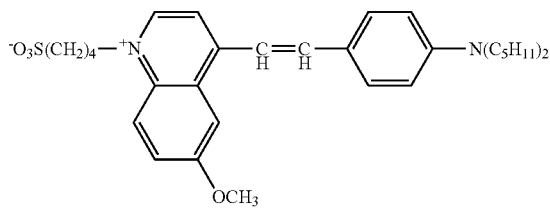

TABLE 2-continued
Selected useful dyes of the Formula $Q_a$—B—$M_a$ or $Q_b$—B—$M_b$ are shown.
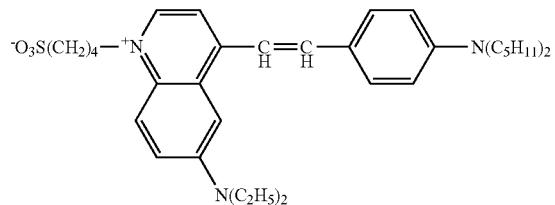
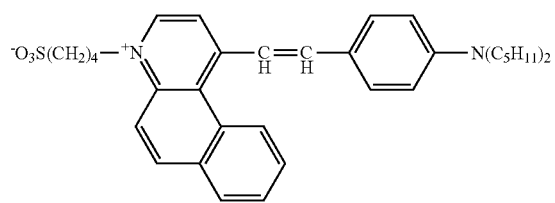
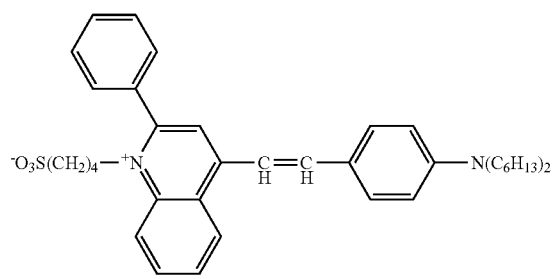
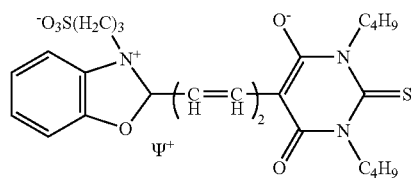
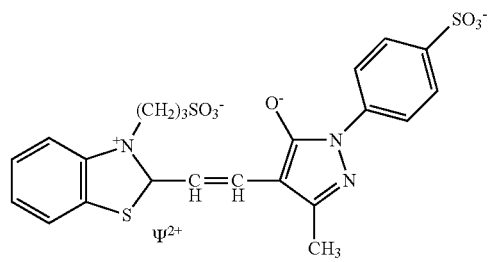
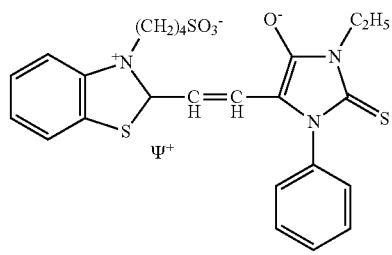

TABLE 2-continued
Selected useful dyes of the Formula $Q_a$—B—$M_a$ or $Q_b$—B—$M_b$ are shown.
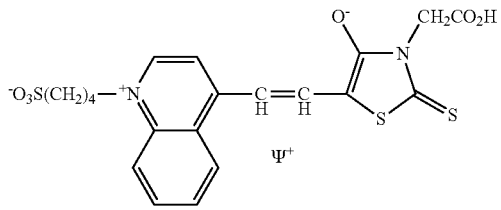
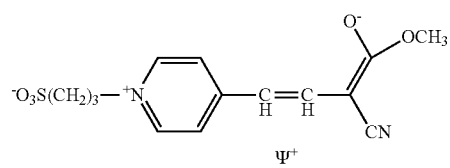
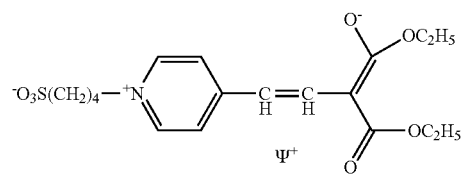
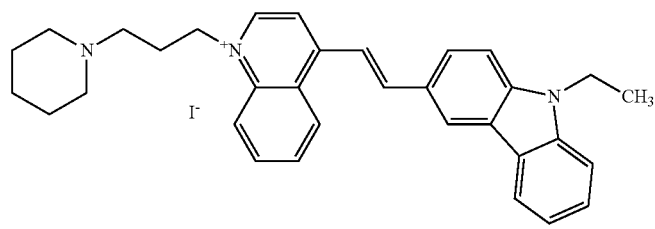 [SMILES: CCn1c2ccccc2c2cc(/C=C/c3cc[n+](CCCN4CCCCC4)c4ccccc34)ccc21 ; [I-]]
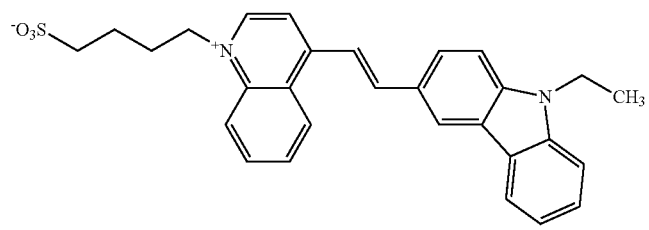
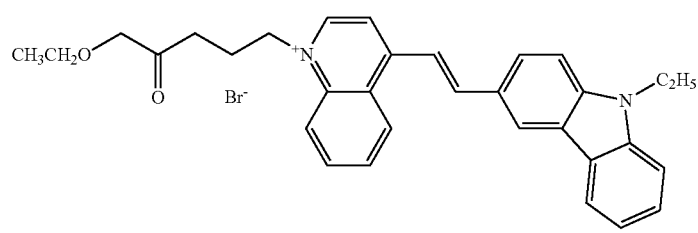
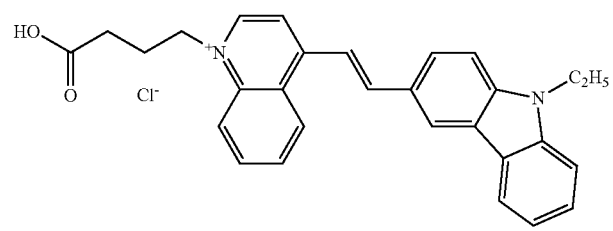 [SMILES: CCn1c2ccccc2c2cc(/C=C/c3cc[n+](CCCC(=O)O)c4ccccc34)ccc21 ; [Cl-]]

TABLE 2-continued
Selected useful dyes of the Formula $Q_a$—B—$M_a$ or $Q_b$—B—$M_b$ are shown.
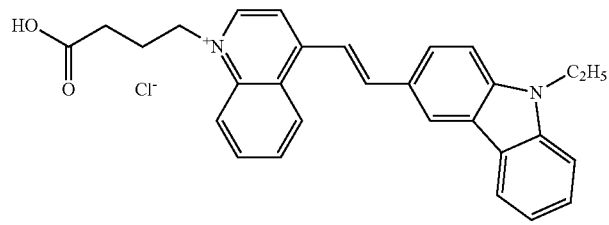 [SMILES: CCn1c2ccccc2c2cc(/C=C/c3cc[n+](CCCC(=O)O)c4ccccc34)ccc21 ; [Cl-]]
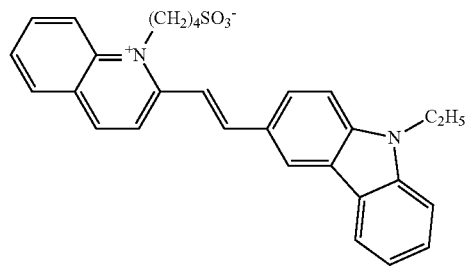
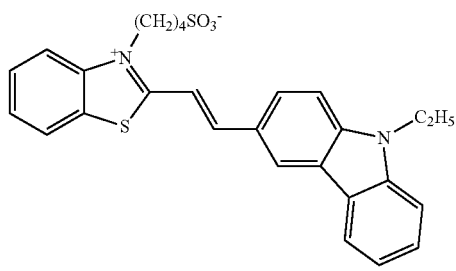
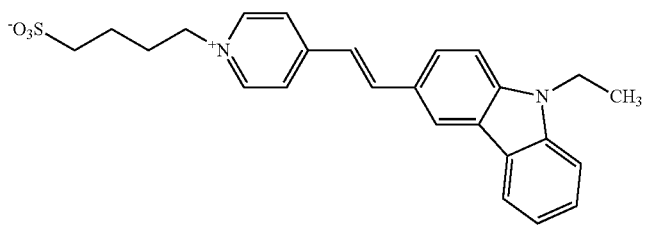
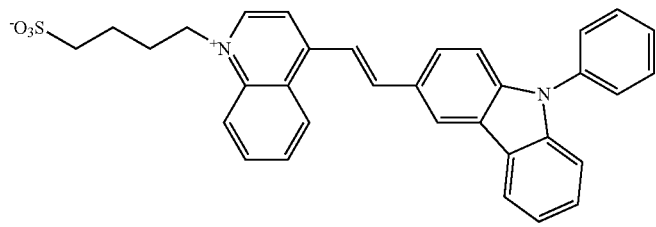
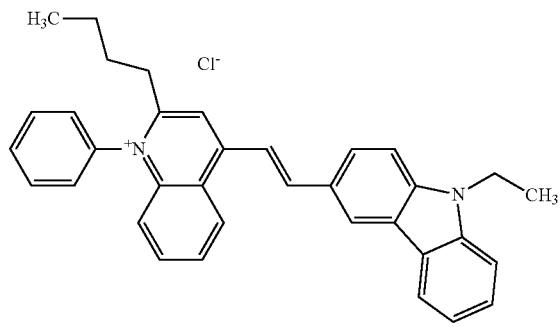 [SMILES: CCCCc1cc(/C=C/c2ccc3c(c2)c2ccccc2n3CC)c2ccccc2[n+]1-c1ccccc1 ; [Cl-]]

TABLE 2-continued

Selected useful dyes of the Formula $Q_a$—B—$M_a$ or $Q_b$—B—$M_b$ are shown.

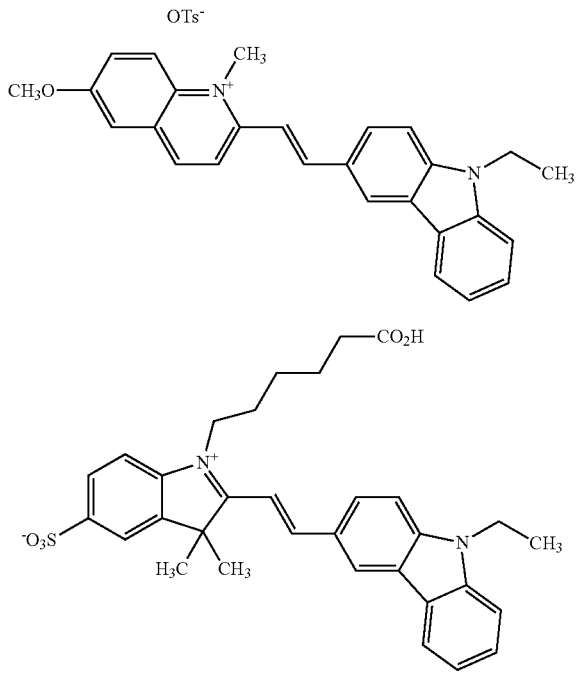

SYPRO® Orange, SYPRO® Red, and SYPRO® Tangerine are members of the styryl dye class described above and are shown in Table 2.

Other fluorophore dyes suitable for use include, but are not limited to, thioinosine, and N-ethenoadenosine, formycin, dansyl, dansyl derivatives, fluorescein derivatives, 6-propionyl-2-(dimethylamino)-napthalene (PRODAN), 2-anilinonapthalene, and N-arylamino-naphthalene sulfonate derivatives such as 1-anilinonaphthalene-8-sulfonate (1, 8-ANS), 2-anilinonaphthalene-6-sulfonate (2, 6-ANS), 2-amino-naphthalene-6-sulfonate, N, N-dimethyl-2-aminonaphthalene-6-sulfonate, N-phenyl-2-aminonaphthal-ene, N-cyclohexyl-2-aminonaphthalene-6-sulfonate, N-phenyl-2-amino-naphthalene-6-sulfonate, N-phenyl-N-methyl-2-aminonaphthalene-6-sulfonate, N-(o-toluyl)-2-amino-naphthalene-6-sulfonate, N-(m-toluyl)-2-amino-naphthalene-6-sulfonate, N-(p-toluyl)-2-aminonaphthalene-6-sulfonate, 2-(p-toluidinyl)-naphthalene-6-sulfonic acid (2, 6-TNS), 4-(dicyanovinyl) julolidine (DCVJ), 6-dodecanoyl-2-dimethylaminonaphthalene (LAURDAN), 6-hexadecanoyl-2-(((2-(trimethylammonium) ethyl) methyl)-amino) naphthalene chloride (PATMAN). Nile red (9-diethylamino-5H-benzo[a]phenoxazine-5-one), N-phenyl-1-naphthylamine, 1, 1-dicyano-2-[6-(dimethylamino) naphthalen-2-yl] propene (DDNP), 4, 4'-dianilino-1, 1-binaphthyl-5, 5-disulfonic acid (bis-ANS), and 5-(4"-dimethylaminophenyl)-2-(4'-phenyl) oxazole derivative dyes, sold under the trademark DAPOXYL™ (Molecular Probes, Inc., Eugene, Oreg.), including the 5-(4"-dimethylaminophenyl)-2-(4'-phenyl) oxazole dyes provided in Diwu, Z. et al., Photochemistry and Photobiology 66 (4): 424-431 (1997), and in BioProbes 25; pp. 8-9. Molecular Probes, Inc., Eugene, Oreg. (1997).

Examples of 5-(4"-dimethylaminophenyl)-2-(4'-phenyl) oxazole derivative dyes, and the corresponding Molecular Probes catalogue number, include 5-(4"-dimethylaminophe-nyl)-2-(4'-phenyl) oxazole burylsulfonamide (D-12801), 5-(4"-dimethylaminophenyl)-2-(4'-phenyl) oxazole-(2-aminoethyl) sulfonamide (D-10460), 5-(4"-dimethylaminophenyl)-2-(4'-phenyl) oxazole butylsulfonamide (D-12801), 5-(4"-dimethylaminophenyl)-2-(4'-phenyl) oxazole-3-sulfonamidophyenylboronic acid (D-10402), 5-(4"-dimethylaminophenyl)-2-(4'-phenyl) oxazole sulfonic acid, sodium salt (D-12800), 5-(4"-dimethylaminophenyl)-2-(4'-phenyl) oxazole sulfonyl hydrazine (D-10430), 5-(4"-dimethylaminophenyl)-2-(4'-phenyl) oxazole-(2-bromoacetamidoethyl) sulfonamide (D-10300), 5-(4"-dimethylaminophenyl)-2-(4'-phenyl) oxazole-2-(3-(2-pyridyldithio) propionamidoethyl) sulfonamide (D-103 01), 5-(4"-dimethylaminophenyl)-2-(4'-phenyl) oxazole sulfonyl chloride (D-10160), 5-(4"-dimethylaminophenyl)-2-(4'-phenyl) oxazole-3-sulfonamidopropionic acid, succinimnidyl ester (D-10162), 5-(4"-dimethylamninophenyl)-2-(4'-phenyl) oxazole carboxylic acid, succinimidyl ester (D-10161).

In some embodiments, a mixture of at least two fluorophore dyes includes one or more styryl dye having the structure Q-B-M, as defined above. In other embodiments, a mixture of at least two fluorophore dyes includes Nile Red and at least one styryl dye. In yet other embodiments, the mixture of at least two fluorophore dyes includes two or more styryl dyes. In some embodiments, the mixture of at least two fluorophore dyes includes two or more styryl dyes having a structure of $Q_a$-B-$M_a$ or $Q_b$-B-$M_b$. In other embodiments, the mixture of at least fluorophore dyes includes three styryl dyes having a structure of $Q_a$-B-$M_a$ or $Q_b$-B-$M_b$. In various embodiments the mixture of at least two fluorophore dyes includes Nile Red and at least two styryl dyes having a structure of $Q_a$-B-$M_a$ or $Q_b$-B-$M_b$.

Examples of fluorophore dyes suitable for use in the methods, kits and compositions described herein that are commercially available include, but are not limited to, Nile Red, SYPRO® Red, SYPRO® Orange, and SYPRO® Tangerine.

The following fluorophore dyes are used in the examples: SYPRO® Protein Gel Stain Starter Kit; S12012; Contains SYPRO® Tangerine, SYPRO® Red, SYPRO® Orange. The styryl fluorophore dyes; SYPRO® Tangerine, SYPRO® Red, and SYPRO® Orange are each capable of fast, easy and sensitive detection of proteins. Nile Red, though typically used to localize and quantitate lipids, is also useful alone or in combination with the styryl fluorophore dyes.

Any instrument capable of delivering controlled heat and recording the fluorescence, i.e. an instrument having a CCD camera or other means of collecting and recording the fluorescence, can be used for PTS. In at least one embodiment, the controlled heating is a thermal ramp. In at least one embodiment, the thermal ramp is between about 20° C. and about 95° C. In at least one embodiment, the controlled heating is isothermal heating. In at least one embodiment, the instrument can plot the fluorescence data throughout the thermal melt assay, generating a fluorescence profile specific to the protein of interest. In at least one embodiment, the instrument has the ability to calculate the $T_m$ of the protein of interest. In at least one embodiment, the instrument includes a MATLAB based TmTool™ to calculate the $T_m$ of the protein from the fluorescence melt plot (e.g., using the Boltzmann equation). In at least one embodiment, the instrument has operational software allowing for the collection of fluorescent data across a wide temperature range at any desired ramp speed. In at least one embodiment, the instrument allows for easily viewing data within the system software, or exportation for further analysis offline.

Examples of instruments that can be used for PTS Assays, include, but are not limited to, Applied Biosystems® Real Time PCR Systems (Life Technologies), including the 7900 HT, 7500 Fast and StepOnePlus™, and Viia™7 Real Time PCR Instruments. The instruments used in the examples provided the benefits of automatic generation of a $T_m$, flexibility of run-method programs and the ability to reset the temperature range in the case of more complexes melt profiles. Further benefits included small reaction volumes, fast and accurate results, and the necessity to use only a few μg of protein.

The protein thermal shift method may be performed variously as described herein. Additional methods of PTS which may be suitable for use in the methods of this invention are described in PCT/US98/24035, Nov. 12, 1997, entailed 'High Throughput Method for Functionally Classifying Proteins Identified Using a Genomics Approach', herein incorporated by reference in its entirety. Variations or changes in the methods may be made by one of skill to the methods as described here, while remaining within the scope of this invention. Some variations are described in the accompanying examples.

In some embodiments, the PTS methods include a buffer. In some embodiments, the buffer may include one of the so-called "Good's" buffers. "Good's" buffers include BES (N,N-bis[2-hydroxyethyl]-2-aminoethanesulfonic acid; 2-[bis(2-hydroxyethyl)amino]ethanesulfonic acid), BICINE (N,N-bis[2-hydroxyethyl]glycine), CAPS (3[cyclohexylamino]-I-propanesulfonic acid), EPPS (N-[2hydroxyethyl] piperazine-N'-[3-propanesulfonic acid]), HEPES ((N-[2-hydroxyethyl]piperazine-N'-[2ethanesulfonic acid]), MES (2-[N-morpholino] ethanesulfonic acid), MOPS (3-[N-morpholino]propanesulfonic acid), PIPES (piperazine-N,N'-bis[2ethanesulfonic acid]; 1,4-piperazinediethanesulfonic acid), TAPS (N-tris[hydroxymethyl]methyl-3-aminopropanesulfonic acid; ([2-hydroxy-1,1-bis(hydroxymethyl) ethyl]amino-1-propanesulfonic acid), TES(N-tris[hydroxymethyl]methyl-2-aminoethanesulfonic acid; 2-([2-hydroxy-1, 1-bis(hydroxymethyl)ethylamino) ethanesulfonic acid), or TRICINE (N-tris[hydroxymethyl] methylglycine; N-[2-hydroxy-1,1 bis(hydroxymethyl)ethyl] glycine). Other buffers may include tris (tris(hydroxymethyl)-aminomethane) or bistris (2-[Bis(2-hydroxyethyl) amino]-2-(hydroxymethyl)-1,3-propanediol).

Other buffers may include inorganic salts such as chloride, or organic salts such as formate, citrate, acetate, heterocycles, including but not limited to imidazole and piperazine, and phosphate, Exemplary buffers include but are not limited to N-(2-hydroxyethyl)-N'-(2-sulfoethyl)piperazine, imidazole, N-(2-hydroxyethylpiperazine)-N'-2ethanesulfonic acid, phosphate, Tris(hydroxymethyl)aminomethane acetate, or Tris(hydroxymethyl)aminomethane hydrochloride.

The buffer or mixture of buffers may be present in the staining mixture at a concentration of 5 mM to 500 mM, preferably about 10 mM to about 200 mM.

The mixture can further include a polyol. The polyol can be added to further stabilize a protein or proteins. A polyol is an alcohol containing multiple hydroxyl groups. Examples of a polyol include but are not limited to, glycerin, ethylene glycol, sucrose, and pentaerythritol. The mixture can further include a surfactant. The surfactant can be added to further stabilize a protein or proteins. In at least one embodiment, the surfactant is present at a concentration that is at least the critical micelle concentration. The critical micelle concentration is the concentration of surfactants above which micelles form and all additional surfactants added to the system become micelles. Surfactants are compounds that lower the surface tension (or interfacial tension) between two liquids or between a liquid and a solid. Surfactants may act as detergents, wetting agents, emulsifiers, foaming agents, and dispersants. The surfactants may be anionic or cationic surfactants. The surfactants may be any surfactants that are usable with biochemical molecules (e.g., proteins). Examples of surfactants include, but are not limited to, ammonium lauryl sulfate, sodium lauryl sulfate (SDS, sodium dodecyl sulfate), sodium laureth sulfate (also known as sodium lauryl ether sulfate (SLES)), sodium myreth sulfate, sodium stearate, sodium lauroyl sarcosinate.

Filters.

In any of the compositions, methods and kits as described here, an optical filter set, hereafter referred to as a "filter", may be used in collecting and viewing the data. A filter may be used in the sample solution mixture to permit selected regions of fluorescence emission to be collected. Removing some undesirable regions of fluorescence emission from detection may permit more finely detailed fluorescence emission information to be collected by the system, and thus provides $T_m$ calculation otherwise difficult to obtain. In some instances of forming a sample solution mixture with the at least one protein and a mixture of at least two fluorophore dyes, the at least two fluorophore dyes may form non-specific interactions with the exterior of a protein in its native or folded state, especially when the protein has significant regions of exterior hydrophobicity, including but not limited to membrane proteins. Employing a filter setting of appropriate wavelength range, the fluorescence not related specifically to the unfolding process can be removed. The methods described herein also include methods of evaluating different filter settings to determine which filter may permit the mixture of at least two fluorophore dyes to provide a minimally fluorescent signal when present in the sample solution mixture with the at least one protein in its native state.

TABLE 3

| | Filter characteristics | | | | | |
|---|---|---|---|---|---|---|
| | m1 (520 ± 15 nm) | m2 (558 ± 11 nm) | m3 (586 ± 10 nm) | m4 (623 ± 14 nm) | m5 (682 ± 14 nm) | m6 (711 ± 12 nm) |
| x1 (470 ± 15 nm) | ♦ | | | | | |
| x2 (520 ± 10 nm) | | ♦ | | | | |
| x3 (550 ± 11 nm) | | | ♦ | | | |
| x4 (580 ± 10 nm) | | | | ♦ | | |
| x5 (640 ± 10 nm) | | | | | ♦ | |
| x6 (550 ± 11 nm) | | | | | | |

Filters may be devised having differing emission/excitation characteristics. Any suitable filter may be used in the methods of the invention to provide a minimally fluorescent signal and when the at least one protein is present in an unfolded state, then each of the at least two fluorophore dyes is configured to provide a substantially increased fluorescent signal. In the table above the "m" numbers indicate an emission ("Em) filter range, and the "x" numbers indicate the excitation ("Ex") filter range. A specific filter may be referred to as, for example, an X1-M1 filter, which would have an excitation filter range of Ex 470±15 nm-Em 520±15 nm. The checked boxes in the table above are exemplary filters often available on instrumentation used for these assays. Any suitable filter range may be used in the methods of the invention and identification of such filter is within the scope of ordinary experimentation. In some embodiments, a suitable filter for the methods of the invention may include an X4-M4 filter having Ex580±10 nm-Em 623±14 nM. In other embodiments, a suitable filter may be an X5-M5 filter having a Ex640±10 nm-Ex 680±14 nm.

Methods.

One of ordinary skill in the art may employ various assays utilizing the determination of the melting temperature ($T_m$) of a protein. The process in which a protein having a tertiary structure goes from a tertiary structure to a random coil structure may be referred to in the art by terms including, but not limited to, protein denaturation, protein unfolding, and protein melt. Additionally, a protein under various sample solution conditions may show a variation or shift in the observed $T_m$ for that protein as a function of the sample solution conditions. Various terms such as thermal melt assays (TMA), thermal shift assay (TSA), protein thermal shift (PTS) analysis, and differential scanning fluorimetry (DSF) are examples of terms of the art in which the determination of the $T_m$ of a protein or proteins is central to the analysis.

In addition to the determination of a melting temperature ($T_m$), various embodiments of isothermal denaturation (ITD) may be utilized, in which a time to denaturation ($D_t$) is determined. For example, in some embodiments of ITD, a thermal ramp may be applied to a protein sample under a set of baseline sample solution conditions (pH, salt, ligand, buffer composition, surfactants, polyols, etc.), and the $T_m$ determined for those conditions. In a subsequent experiment or set of experiments, a protein sample may be subjected to various sample solution conditions. However, for the subsequent analysis, instead of a temperature ramp, the temperature determined for the baseline sample solution conditions would be used in the experiment, and the fluorescence signal would be monitored as a function of time. The experiment may be repeated at temperatures close to the predetermined $T_m$ in order to compare the rate of denaturation as a function of time and sample solution conditions.

The use of a mixture of dyes can provide an advantage over a single dye in some cases by increasing the fluorescence signal over background. In other embodiments, the mixture of fluorophore dyes used in the PTS methods provides additional detail in the mode of protein unfolding as different dyes will associate with different regions of the at least one protein as portions of its hydrophobic core, including but not limited to protein loops, functional domains, helical bundles, beta-barrels, or other structural/functional motifs) becomes exposed to the sample solution mixture environment during the controlled heating. The differential association and $T_m$ for each area of interaction can be observed using spectrally different dyes. Additionally, for investigation of a protein where little or no knowledge exists about its structure of behavior upon exposure to a ligand, the use of a mixture of dyes does not require advance knowledge for experiment design.

Useful combinations of fluorophore dye and protein mixtures for PTS identified herein include, but are not limited to, protein-ligand complexes and SYPRO® Orange (e.g., T4DNA ligase-ATP); Rec A and SYPRO® Orange; T4DNA ligase and SYPRO® Orange; protein mutants and SYPRO® Orange (e.g., SuperScript®II and SuperScript®III); protein-antibody complexes and SYPRO® Orange (e.g., Decorin-antibody); BSA and SYPRO® Red; Human Plasma and SYPRO® Red or a mixture of SYPRO® Orange, SYPRO® Red, and SYPRO® Tangerine; Membrane proteins and a mixture of Nile Red and SYPRO® Orange; SuperScript®II or SuperScript®III and a mixture of Nile Red and SYPRO® Orange; RecA and a mixture of SYPRO® Orange, SYPRO® Red, and SYPRO® Tangerine; Proteinase K and SYPRO® Red; and RNAse A and SYPRO® Red. It is envisioned that the results can be extrapolated to like proteins and/or protein combinations. For example, SYPRO® Orange may show similar utility when used with other protein-ligand complexes.

Another advantage provided by the methods disclosed herein is that the methods provide for the use of miniaturized assay volumes (e. g., 1-5 pL), which facilitates the use of high density microplate assay arrays of 16×24 (384 well), 32×48 (1536 well), or further customized arrays. Only about 5 to 40 picomole of protein may be required (0.1 pg to 1.0 llg for a 25 kDa protein) per assay well, for a final protein concentration of about 1 to 4 uM. Thus, 1.0 mg of protein may be used to conduct $10^3$ to $10^4$ assays in the miniaturized format.

The methods of using PTS disclosed herein may include identifying an optimized fluorophore dye or dye mixture to allow for identifying partial or complete unfolding of a protein due to a thermal change. The methods include screening single fluorophore dyes and/or mixtures of fluorophore dyes to identify which fluorophore dyes give the best results in a PTS assay for a given protein, protein-protein interaction, and/or protein-ligand interaction.

The screening method may include the steps of forming a sample solution mixture having at least one protein. In some embodiments the at least one protein is in its native state, which may include having a tertiary structure that is folded. In some embodiments, the sample solution mixture having at least one protein further includes a ligand which is potentially capable of interacting with the at least one protein. In some embodiments, the interaction with the at least one protein is with the protein in its native state. In other embodiments, the interaction of the ligand with the at least one protein is with the protein where the protein still has a tertiary structure, but the tertiary structure is modified from the native state when the ligand interacts with the at least one protein. The sample solution mixture may also include a fluorophore dye or a fluorophore dye mixture. In some embodiments, the sample solution mixture includes a mixture of at least two fluorophore dyes. Once the sample solution is formed, a controlled heating is applied to the sample solution mixture. Fluorescent emissions from the fluorophore dye or fluorophore dye mixture are measured over a range of temperatures. The range of temperatures may include the temperatures both below and above an expected $T_m$ of the at least one protein. In some embodiments, the range of temperatures may include the temperatures in an extended range above an expected $T_m$. In other embodiments, the range of temperatures is pre-selected to be a standard range of temperatures. In some embodiments, measurements are made at the temperature the sample solution mixture exhibits before the controlled heating is applied and throughout the whole range of temperatures achieved by the sample solution mixture while heating is applied. The steps described above are then repeated using a different fluorophore dye or different fluorophore dye mixture, and fluorescence measured as described.

In some embodiments, the at least one protein, ligand (if present), and fluorophore dye or mixture of fluorophore dyes are kept the same while varying filters, in order to identify the best filter for the above combination in the sample solution. Fluorescence profiles of the melt curve using each filter may be obtained and compared to identify the most suitable filter, i.e. providing the most minimally fluorescent signal when the at least one protein is still folded, and/or providing the most substantially fluorescent signal when the at least one protein unfolds, with or without the ligand being present. In some embodiments, a suitable filter may be an X4-M4 filter having Ex580±10 nm-Em 623±14 nM. In other embodiments, a suitable filter may be an X5-M5 filter having an Ex640±10 nm Ex 6801±14 nm.

Comparison of the fluorescence profile (also referred to as a protein melt curve) obtained from each individual experiment using a different fluorophore dye, a different mixture of fluorophore dyes, a different mixture of at least two fluorophore dyes, or a different filter can be used to determine the conditions which provide the fluorescence profile that is most useful in the thermal shift assays to be conducted. In some embodiments, the fluorescence profile is transformed mathematically to provide a first derivative trace, which permits identification of the $T_m$, observable as an inflection point. Once the best fluorophore dye, fluorophore dye mixture, or filter is identified. PTS can be used in the other methods of the invention, which include identifying molecules that increase or decrease the stability of the protein, protein-protein interaction, and/or protein-ligand interaction. Alternatively, PTS can be used to identify the best conditions for use or storage of the protein, protein-protein interaction, and/or protein-ligand interaction (e.g., for crystallization). In at least one embodiment, one or more fluorophore dyes are chosen from Nile Red and styryl dyes. In some embodiments, a styryl dye such as SYPRO® Orange, SYPRO® Red, or SYPRO® Tangerine can be used.

The methods may include the steps of measuring the stability of the at least one protein, either in the presence of a ligand, or with no ligand present, in differing buffers, by forming a sample solution mixture of the at least one protein and a mixture of at least two fluorophore dyes in a first buffer, applying a controlled heating to the mixture, measuring fluorescence emitted over a temperature range and identifying a first $T_m$ for the protein in the first buffer. Subsequently, a second $T_m$ may be calculated from the measured fluorescence obtained from the at least one protein and the mixture of at least two fluorophore dyes in a second buffer. Comparison of the first $T_m$ with the second $T_m$ thereby provides an analysis of the stability of the at least one protein in the presence of the first buffer compared to the stability obtained in the presence of the second buffer. In some embodiments the at least one protein is in its native state, which may include having a tertiary structure that is folded. In some embodiments, the sample solution mixture having at least one protein further includes a ligand which is potentially capable of interacting with the at least one protein. In some embodiments, the interaction with the at least one protein is with the protein in its native state. In some embodiments, the at least one protein and ligand form a protein/ligand complex. In other embodiments, the interaction of the ligand with the at least one protein is with the protein where the protein still has a tertiary structure, but the tertiary structure is modified from the native state when the ligand interacts with the at least one protein. Once the sample solution is formed, a controlled heating is applied to the sample solution mixture. Fluorescent emissions from the fluorophore dye mixture are measured over a range of temperatures. The range of temperatures may include the temperatures both below and above an expected $T_m$ of the at least one protein. In some embodiments, the range of temperatures may include the temperatures in an extended range above an expected $T_m$. In other embodiments, the range of temperatures is pre-selected to be a standard range of temperatures. In some embodiments, measurements are made at the temperature the sample solution mixture exhibits before the controlled heating is applied and throughout the whole range of temperatures achieved by the sample solution mixture while heating is applied.

In some embodiments, the at least one protein, ligand (if present), and fluorophore dye or mixture of fluorophore dyes are kept the same while varying filters, in order to identify the best filter for the above combination in the sample solution. Fluorescence profiles of the melt curve using each filter may be obtained and compared to identify the most suitable filter, i.e. providing the most minimally fluorescent signal when the at least one protein is still folded, and/or providing the most substantially fluorescent signal when the at least one protein unfolds, with or without the ligand being present. In some embodiments, a suitable filter may be an X4-M4 filter having Ex580±10 nm-Em 623±14 nM. In other embodiments, a suitable filter may be an X5-M5 filter having an Ex640±10 nm-Ex 680±14 nm.

Comparison of the fluorescence profile (also referred to as a protein melt curve) obtained from each individual experiment using a different buffer can be made to determine the conditions which provide the fluorescence profile that is most useful in the thermal shift assays to be conducted. In some embodiments, the fluorescence profile is transformed mathematically to provide a first derivative trace, which permits identification of the $T_m$, observable as an inflection point.

In at least one embodiment, the sample solution mixture includes a surfactant. In at least one embodiment, the surfactant is present at a concentration that is at least the critical micelle concentration. In at least one embodiment, the sample solution mixture further includes a polyol. In at least one embodiment, the polyol is glycerol or a polysaccharide. In at least one embodiment, the methods can be performed without the measurement of the $T_m$ by comparing fluorescence from the fluorophore dye or dyes.

The methods may include the steps of measuring the stability of at least one protein in the presence of a ligand and with no ligand present, by forming a sample solution mixture of at least one protein and a mixture of at least two fluorophore dyes without the ligand, applying a controlled heating to the mixture, measuring fluorescence emitted over a temperature range and identifying a first $T_m$ for the protein without the ligand. A second experiment is performed, calculating a second $T_m$ from the measured fluorescence obtained from the at least one protein and the mixture of at least two fluorophore dyes in the presence of the ligand, and comparing the first $T_m$ and the second $T_m$, thereby analyzing the stability of the at least one protein in the presence of the ligand compared to the stability observed when the ligand is not present. The ligand and the at least one protein may form a protein/ligand complex when present in the sample solution mixture.

The method for measuring stability of the at least one protein may include the steps of forming a sample solution mixture having the at least one protein and a mixture of at least two fluorophore dyes. In some embodiments the at least one protein is in its native state, which may include having a tertiary structure that is folded. In some embodiments, the sample solution mixture having at least one protein further includes a ligand which is potentially capable of interacting with the at least one protein. In some embodiments, the at least one protein and ligand form a protein/ligand complex. In some embodiments, the interaction with the at least one protein is with the protein in its native state. In other embodiments, the interaction of the ligand with the at least one protein is with the protein where the protein still has a tertiary structure, but the tertiary structure is modified from the native state when the ligand interacts with the at least one protein. The ligand may be of any suitable class. In some embodiments, the at least one protein is an antibody and the ligand is an antigen, which interact to form an antibody/antigen complex. In other embodiments, the at least one protein is interacted with a ligand which is a second protein. In yet other embodiments, the ligand that interacts with the at least one protein is a peptide, polynucleotide, or an aptamer. In other embodiments, the ligand is a synthetic organic molecule which may be capable of interacting with the at least one protein to stabilize or destabilize the protein. In some embodiments, the ligand that is a synthetic organic molecule interacts with the at least one protein to modify the normal function of the at least one protein.

Once the sample solution is formed, a controlled heating is applied to the sample solution mixture. Fluorescent emissions from the fluorophore dye or fluorophore dye mixture are measured over a range of temperatures. The range of temperatures may include the temperatures both below and above an expected $T_m$ of the at least one protein. In some embodiments, the range of temperatures may include the temperatures in an extended range above an expected $T_m$. In other embodiments, the range of temperatures is pre-selected to be a standard range of temperatures. In some embodiments, measurements are made at the temperature the sample solution mixture exhibits before the controlled heating is applied and throughout the whole range of temperatures achieved by the sample solution mixture while heating is applied. The steps described above are then repeated using a different fluorophore dye or different fluorophore dye mixture, and fluorescence measured as described.

In some embodiments, the at least one protein, ligand (if present), and fluorophore dye or mixture of fluorophore dyes are kept the same while varying filters, in order to identify the best filter for the above combination in the sample solution. Fluorescence profiles of the melt curve using each filter may be obtained and compared to identify the most suitable filter, i.e. providing the most minimally fluorescent signal when the at least one protein is still folded, and/or providing the most substantially fluorescent signal when the at least one protein unfolds, with or without the ligand being present. In some embodiments, a suitable filter may be an X4-M4 filter having Ex580±10 nm-Em 623±14 nM. In other embodiments, a suitable filter may be an X5-M5 filter having an Ex64010 nm-Ex 680±14 nm.

In some embodiments, the at least one protein, mixture of fluorophore dyes, and filter are kept the same while varying ligands. Fluorescence profiles are measured for each ligand under investigation. Comparison of the fluorescence profile (also referred to as a protein melt curve) obtained from each individual experiment using a different ligand can be made to determine which if any ligands stabilize the protein most significantly, destabilize the protein most significantly or provide a $T_m$ preselected to be desirable. In some embodiments, the fluorescence profile is transformed mathematically to provide a first derivative trace, which permits identification of the $T_m$, observable as an inflection point.

In at least one embodiment, the sample solution mixture includes a buffer. In at least one embodiment, the sample solution mixture includes a surfactant. In at least one embodiment, the surfactant is present at a concentration that is at least the critical micelle concentration. In at least one embodiment, the sample solution mixture further includes a polyol. In at least one embodiment, the polyol is glycerol or a polysaccharide. In at least one embodiment, the methods can be performed without the measurement of the $T_m$ by comparing fluorescence from the fluorophore dye or dyes.

The methods can be used to look at molecules that specifically recognize and bind to proteins (protein complexes) such as protein-antibody complexes, protein-peptide complexes, protein-ligand complexes, protein-lectin complexes, protein-aptamer complexes, etc. In the discussion, ligand will be used to refer to any molecule that specifically recognizes and binds to a protein.

The methods can involve the steps of measuring the stability of at least one protein by forming a sample solution mixture of at least one protein and at least one fluorophore dye without the ligand, applying a controlled heating to the mixture, measuring fluorescence emitted over a temperature range and identifying a first $T_m$ for the protein without the ligand. Then, calculating a second $T_m$ from the measured fluorescence obtained from the at least one protein and at least one fluorophore dyes with a ligand, and comparing the first $T_m$ and the second $T_m$, thereby analyzing the stability of the at least one protein in the presence of the ligand compared to the stability obtained without the ligand. In at least one embodiment, the same fluorophore dye or dyes are used for both steps. In at least one embodiment, the sample solution mixture includes a mixture of at least two fluorophore dyes. In at least one embodiment, the sample solution mixture includes a buffer. In at least one embodiment, the sample solution mixture includes a surfactant. In at least one embodiment, the surfactant is present at a concentration that is at least the critical micelle concentration. In at least one embodiment, the sample solution mixture further includes a polyol. In at least one embodiment, the polyol is glycerol or a polysaccharide. In at least one embodiment, the methods can be performed without the measurement of the $T_m$ by comparing fluorescence from the fluorophore dye or dyes.

Aptamers are RNA oligomers, DNA oligomers or peptides that bind specific target molecules. Aptamers can bind with excellent affinity and specificity and can rival antibodies in usefulness, but with improved stability. Aptamers can be any length, but in use, aptamers are usually ~15-60 nt long. Aptamers can be used in therapeutics (inhibitory for targets such as vascular endothelial growth factor (VEGF) and thrombin). The first aptamer was FDA approved in 2004 for Macular Degeneration. Successful aptamers are highly specific, generally non-immunogenic, and generally stable but can quickly degrade in serum unless modified. Methods of identifying aptamers that specifically bind to proteins can involve the use of PTS methods described herein.

A general method to find aptamers that bind specifically and with high affinity to a protein of interest can begin with a pool of randomly generated oligos, tested for preferential binding to the protein of interest by, for example, the SELEX technique, in which oligos compete for protein binding over multiple rounds of selection. Systematic Evolution of Ligands by Exponential Enrichment (SELEX), also referred to as in vitro selection or in vitro evolution, is a combinatorial technique in molecular biology for producing oligonucleotides of either single-stranded DNA or RNA that specifically bind to a target (e.g., a protein and/or ligand), which was first described by Tuerk et al. Science Vol. 249, p 505-510, 3 Aug. 1990.

Once identified (e.g., using SELEX), aptamers can be further tested for usefulness using the PTS methods described herein. PTS can be used to confirm and investigate aptamer binding by testing the stability of the protein in the presence of the aptamer. The addition of oligomers to proteins with a DNA/RNA binding site may stabilize the protein and has been demonstrated to result in a higher $T_m$ for that protein in Protein Thermal Shift (PTS) experiments. Thus, PTS can be used to confirm that aptamers that are identified using the SELEX technique actually do bind to and stabilize the target. Further, the PTS methods described herein can be used to prioritize aptamers by binding affinity ranking (e.g., according to $T_m$ shift). Aptamers identified by SELEX or other methods are often later modified (truncated/ chemical modification, etc.) to improve binding and/or stability. Thus, PTS can be used to identify whether modification of the aptamer increases the stability of the target/ aptamer interaction.

While there are many uses for aptamers identified in this way, once an aptamer is confirmed to recognize a protein (e.g., target) with the highest affinity relative to other aptamers, that aptamer can be immobilized onto a bead (e.g., Nemo beads) and be utilized to pull out that protein of interest (e.g., target) from complex samples, including blood, plasma, urine, or even a single lysed cell.

One exemplary embodiment of using the PTS methods described herein to confirm or identify aptamer binding, involves the following preliminary steps: (a) use of SELEX Technique to enrich a pool of random oligos for the aptamer that preferentially binds target; and (b) Utilization of sequencing by any suitable means including semiconductor (Ion Torrent™, such as Ion Chef™ or PGM™ systems) or resynthesis methods (including systems available from Illumina® and others), to identify the aptamer sequence. Confirmation of the aptamer—Protein/Target interaction may be performed by the Protein Thermal Shift methods described herein. Further directed evolution of the confirmed interacting aptamers can be identified by screening modified aptamers for binding affinity with PTS, where the aptamers are further modified modifications to improve nuclease stability using a variety of chemical modifications such as introducing modifiers such as PEG, or incorporating LNA within the aptamer sequences). Modified nucleotides may be included during the selection process, as they can influence aptamer folding and binding affinity. Further methods can include coating beads (like Nemo beads) with the aptamer sequence to isolate the protein/target from biological samples (blood, plasma, urine, lysed single cell) and to isolate the aptamerprotein target complex. The aptamer-protein-target complex can then be quantified using a quantitative PCR (e.g., qPCR-PLA™ (Proximity Ligation Assay) type mechanism. For example, the Proximity Ligation Assay is a three step process that includes: (a) binding of paired antibody-oligonucleotide probes to a protein; (b) templated ligation of the oligonucleotides bound in proximity, followed by (c) realtime PCR. This method can be modified to utilize the aptamer-protein target as the ligation targets for further amplification and detection.

Once an aptamer is confirmed to recognize a protein target with the highest affinity relative to other aptamers, that aptamer could be immobilized onto a magnetic bead and be utilized to pull out that protein of interest from complex samples, including blood, plasma, urine, or even a single lysed cell.

Alternative PTS methods which may be adapted to be used within the methods of the present invention are described in International Patent Appl. Nos. PCT/US 98/24035 (published May 20, 1999 as publication no. WO 99/24050) and PCT/US97/08154 (published Nov. 13, 1997 as publication no. WO 97/42500); U.S. patent application Ser. No. 08/853,464, filed May 9, 1997; and U.S. patent application Ser. No. 08/843,459, filed May 9, 1997, each of which is herein incorporated by reference in its entirety. In summary, the methods in PCT/US98/24035 and its US counterpart allow for functionally classifying a protein capable of unfolding due to a thermal change, by classifying the protein according to the set of molecules in a multiplicity of different molecules that shift the thermal unfolding curve of the protein. The methods involve using PTS to identify the function of an unknown protein by screening one or more of a multiplicity of different molecules for their ability to modify the stability of a protein with unknown function, wherein modification of the stability of the protein indicates that the molecule binds to the protein. An activity spectrum for the protein under investigation can be generated, which reflects a subset of molecules, from the multiplicity of different molecules screened, that modified the stability of the protein and thereby identified as ligands capable of binding to the protein. Comparison of the activity spectrum for the protein under investigation to one or more functional reference spectrum lists may permit classifying the protein according to the set of molecules in said multiplicity of different molecules that modify the stability of said protein.

PCT/US97/08154 and its US counterpart provide methods for ranking the affinity of each of a multiplicity of different molecules for a target molecule which is capable of denaturing due to a thermal change. The methods include contacting the target molecule with one molecule of the multiplicity of different molecules in each of a multiplicity of containers, simultaneously heating the multiplicity of containers, measuring in each of the containers a physical change associated with the thermal denaturation of the target molecule resulting from the heating in each of the containers, generating a thermal denaturation curve for the target molecule as a function of temperature for each of the containers and determining a midpoint temperature ($T_m$), comparing the Tin of each of the thermal denaturation curves with the $T_m$ of a thermal denaturation curve obtained for the target molecule in the absence of any of the molecules in the multiplicity of different molecules, and ranking the affinities of the multiplicity of different molecules according to the change in $T_m$ of each of the thermal denaturation curves. Variations of these methods can be used with the presently claimed methods of screening.

Methods of PTS using a single fluorophore dye or a mixture of fluorophore dyes can be used for the purposes of screening buffer conditions for optimized protein stability, screening for ligands that bind and enhance protein stability, screening protein-protein interactions for enhancement of protein stability, screening other conditions for optimized protein stability, point mutations for enhanced stability, screening other types of mutations for protein stability enhancement, screening crystallization conditions for protein stability, screening storage conditions for protein stability, screening conditions in which a protein will be used (e.g., production conditions, treatment conditions, etc.) for protein stability, etc. Other methods can include the analysis of complex proteins, analysis of crystallization conditions, identification and/or evaluation of proteins that have mutations, identification of synthetic organic molecules that modify protein function in a desired manner, and analysis of disease conditions.

The difficulty and expense often involved in isolating or obtaining a protein of interest demands that care be taken with subsequent handling or storage in order to maximize the utility and longevity of the protein and to ensure data quality is not affected by degradation or aggregation events. Conditions that favor long-term stability are a common requirement for almost all research or applied techniques involving proteins. There are many factors that may affect protein stability, including salt concentrations, pH, surfactant concentration, temperature, buffer, polyol concentration or the use of specific ligands that can interact with proteins in different ways. Given the large number of possible combinations one could test in order to determine the environmental conditions that would favor maximum stability, it is highly desirable to adopt a technique that can simplify and streamline the investigation process. The PTS Assay is a fast and convenient screening method for detecting changes in protein thermal stability. The use of on AB® Real Time PCR Systems can increase the speed and/or convenience of the assay.

The methods can involve the steps of measuring the stability of at least one protein by forming a sample solution mixture of at least one protein and at least one fluorophore dye in a first buffer, applying a controlled heating to the mixture, measuring fluorescence emitted over a temperature range and identifying a first $T_m$ for the protein in the first buffer. A second $T_m$ can then be calculated from a measured fluorescence obtained from the at least one protein and at least one fluorophore dye in a second buffer, during the application of a controlled heating. The first $T_m$ and the second $T_m$ may be compared, thereby analyzing the stability of the at least one protein in the presence of the first buffer compared to the stability obtained in the presence of the second buffer. In some embodiments the at least one protein is in its native state, which may include having a tertiary structure that is folded. In some embodiments, the sample solution mixture having at least one protein further includes a ligand which is potentially capable of interacting with the at least one protein. In some embodiments, the interaction with the at least one protein is with the protein in its native state. In some embodiments, the at least one protein and ligand form a protein/ligand complex. In other embodiments, the interaction of the ligand with the at least one protein is with the protein where the protein still has a tertiary structure, but the tertiary structure is modified from the native state when the ligand interacts with the at least one protein. Once the sample solution is formed, a controlled heating is applied to the sample solution mixture. Fluorescent emissions from the fluorophore dye or fluorophore dye mixture are measured over a range of temperatures. The range of temperatures may include the temperatures both below and above an expected $T_m$ of the at least one protein. In some embodiments, the range of temperatures may include the temperatures in an extended range above an expected $T_m$. In other embodiments, the range of temperatures is pre-selected to be a standard range of temperatures. In some embodiments, measurements are made at the temperature the sample solution mixture exhibits before the controlled heating is applied and throughout the whole range of temperatures achieved by the sample solution mixture while heating is applied.

In some embodiments, the at least one protein, ligand (if present), and fluorophore dye or mixture of fluorophore dyes are kept the same while varying filters, in order to identify the best filter for the above combination in the sample solution. Fluorescence profiles of the melt curve using each filter may be obtained and compared to identify the most suitable filter, i.e. providing the most minimally fluorescent signal when the at least one protein is still folded, and/or providing the most substantially fluorescent signal when the at least one protein unfolds, with or without the ligand being present. In some embodiments, a suitable filter may be an X4-M4 filter having Ex580 nm Em 623 nM. In other embodiments, a suitable filter may be an X5-M5 filter having an Ex640 nm Ex 680 nm.

Comparison of the fluorescence profile (also referred to as a protein melt curve) obtained from each individual experiment using a different buffer can be made to determine the conditions which the at least one protein is most stable. In some embodiments, the fluorescence profile is transformed mathematically to provide a first derivative trace, which permits identification of the $T_m$, observable as an inflection point.

In at least one embodiment, the same fluorophore dye or mixture of fluorophore dyes are used for both steps. In at least one embodiment, the sample solution mixture includes a mixture of at least two fluorophore dyes. In at least one embodiment, the sample solution mixture includes a surfactant. In at least one embodiment, the surfactant is present at a concentration that is at least the critical micelle concentration. In at least one embodiment, the sample solution mixture further includes a polyol. In at least one embodiment, the polyol is glycerol or a polysaccharide. In at least one embodiment, the methods can be performed without the measurement of the $T_m$ by comparing fluorescence from the fluorophore dye or dyes.

Methods of PTS using a single fluorophore dye or mixture of fluorophore dyes can be used to identify mutated proteins, enzymes or receptors with enhanced stability relative to wild type. For example, a fluorescence imaging system, (e.g., a fluorescence emission imaging system) can be used to monitor protein unfolding in a microplate thermal shift assay. In this embodiment, a plurality of samples each having a distinct protein having point mutations that may differ from each other is heated simultaneously between 25 to 110° C. A fluorescence emission reading is taken for each of the plurality of samples simultaneously. For example, the fluorescence in each well of a 96 or a 384 well microplate can be monitored simultaneously. Alternatively, fluorescence readings can be taken continuously and simultaneously for each sample. At lower temperatures, all samples display a low level of fluorescence.

As the temperature is increased, the fluorescence in each sample increases. Wells which contain mutated proteins which have enhanced stability shift the thermal unfolding curve to higher temperatures. As a result, wells which contain mutated proteins which have enhanced stability fluoresce less, at a given temperature above the temperature of the target molecule without mutation. If the samples are heated in incremental steps, the fluorescence of all of the plurality of samples can be simultaneously imaged at each heating step. If the samples are heated continuously, the fluorescent emission of all of the plurality of samples can be simultaneously imaged during heating.

The method for identifying mutated proteins may include the steps of forming a sample solution mixture having at least a first protein. In some embodiments the at least first one protein is in its native state, which may include having a tertiary structure that is folded. In other embodiments, the at least first protein still has a tertiary structure, but the tertiary structure is modified from a native state of a parent protein (wildtype), due to a mutation that the at least first protein has compared to that of the parent protein. The sample solution mixture may also include a fluorophore dye or a fluorophore dye mixture. In some embodiments, the sample solution mixture includes a mixture of at least two fluorophore dyes. The method also includes forming a second solution mixture having a second protein, which may be different from the first protein. In some embodiments the second protein is in its native state, which may include having a tertiary structure that is folded. In other embodiments, the second protein still has a tertiary structure, but the tertiary structure is modified from a native state of a parent protein, due to a mutation that the second protein has compared to that of the parent protein. The second sample solution mixture may also include a fluorophore dye or a fluorophore dye mixture. In some embodiments, the second sample solution mixture includes a mixture of at least two fluorophore dyes. The method may also include a plurality of sample solution mixtures each having a distinctive protein, which may be different from the first, second, or parent protein. In some embodiments each of the plurality of distinctive proteins is in its native state, which may include having a tertiary structure that is folded. In other embodiments, each of the plurality of distinctive proteins still has a tertiary structure, but the tertiary structure is modified from a native state of a parent protein, due to a mutation that each of the plurality of distinctive proteins has compared to that of the parent protein. Each of the plurality of sample solution mixtures may also include a fluorophore dye or a fluorophore dye mixture. In some embodiments, each of the plurality of sample solution mixtures includes a mixture of at least two fluorophore dyes.

Once the sample solution is formed, a controlled heating is applied to the sample solution mixture. Fluorescent emissions from the fluorophore dye or fluorophore dye mixture are measured over a range of temperatures. The range of temperatures may include the temperatures both below and above an expected $T_m$ of the at least one protein. In some embodiments, the range of temperatures may include the temperatures in an extended range above an expected $T_m$. In other embodiments, the range of temperatures is pre-selected to be a standard range of temperatures. In some embodiments, measurements are made at the temperature the sample solution mixture exhibits before the controlled heating is applied and throughout the whole range of temperatures achieved by the sample solution mixture while heating is applied. The steps described above are then repeated using a different fluorophore dye or different fluorophore dye mixture, and fluorescence measured as described.

In some embodiments, a filter is used to provide the most minimally fluorescent signal when the at least one protein is still folded, and/or providing the most substantially fluorescent signal when the at least one protein unfolds, with or without a ligand being present. In some embodiments, a suitable filter may be an X4-M4 filter having Ex580±10 nm-Em 623±14 nM. In other embodiments, a suitable filter may be an X5-M5 filter having an Ex640±10 nm-Ex 680±14 nm.

In at least one embodiment, each of the plurality of sample solution mixtures includes a buffer. In at least one embodiment, each of the plurality of sample solution mixtures includes a surfactant. In at least one embodiment, the surfactant is present at a concentration that is at least the critical micelle concentration. In at least one embodiment, each of the plurality of sample solution mixtures further includes a polyol. In at least one embodiment, the polyol is glycerol or a polysaccharide. In at least one embodiment, the methods can be performed without the measurement of the $T_m$ by comparing fluorescence from the fluorophore dye or mixture of fluorophore dyes.

Comparison of the fluorescence profile (also referred to as a protein melt curve) obtained from of the plurality of sample solution mixtures can be sued to determine which, if any of the mutated proteins is more stable or less stable than the parent protein or other reference protein. In some embodiments, the fluorescence profile is transformed mathematically to provide a first derivative trace, which permits identification of the $T_m$, observable as an inflection point.

Other methods can involve the steps of measuring the stability of the unmutated protein (wildtype) by forming a sample solution mixture of the unmutated protein and a mixture of at least two fluorophore dyes in a first buffer, applying a controlled heating to the mixture, measuring fluorescence emitted over a temperature range and identifying a first $T_m$ for the unmutated protein in the first buffer. Then, calculating a second $T_m$ from the measured fluorescence obtained from a mutated protein and the mixture of at least two fluorophore dyes in a second buffer, and comparing the first $T_m$ and the second $T_m$, thereby analyzing the stability of the mutated protein to the unmutated protein. In at least one embodiment, the sample solution mixture includes a surfactant. In at least one embodiment, the surfactant is present at a concentration that is at least the critical micelle concentration. In at least one embodiment, the sample solution mixture further includes a polyol. In at least one embodiment, the polyol is glycerol or a polysaccharide. In at least one embodiment, the methods can be performed without the measurement of the $T_m$ by comparing fluorescence from the fluorophore dye or dyes.

Methods of PTS using a single or mixture of dyes can be used to identify crystallization conditions that enhance stability for protein crystallization. For example, a fluorescence imaging system, (e.g., a fluorescence emission imaging system) can be used to monitor protein unfolding in a microplate thermal shift assay. Methods involve identifying crystallization conditions that increase the stability of a protein of interest (a protein to be crystallized). In this way, optimized conditions for crystallization of the at least one protein can be identified, which may include evaluating differing selections and/or mixtures of buffers, surfactants, polyols, pH, temperature, and salts. If the conditions result in complete or partial unfolding of the protein of interest, the conditions may not be useful for crystallization of the at least one protein.

For example, when analyzing the use of a buffer for crystallization methods, the methods can involve the steps of measuring the stability of at least one protein by forming a sample solution mixture of the at least one protein and at least one fluorophore dye in a first crystallization buffer, applying a controlled heating to the mixture, measuring fluorescence emitted over a temperature range and identifying a first $T_m$ for the protein in the first buffer. Then, calculating a second $T_m$ from the measured fluorescence obtained from the at least one protein and at least one fluorophore dye in a second crystallization buffer, and comparing the first $T_m$ and the second $T_m$, thereby analyzing the stability of the at least one protein in the presence of the first crystallization buffer compared to the stability obtained in the presence of the second crystallization buffer. In at least one embodiment, the dyes used in the first and second steps are the same fluorophore dye or dyes. In at least one embodiment, the sample solution mixture includes a mixture of at least two fluorophore dyes.

In some embodiments the at least one protein is in its native state, which may include having a tertiary structure that is folded. In some embodiments, the sample solution mixture having at least one protein further includes a ligand which is potentially capable of interacting with the at least one protein. In some embodiments, the interaction with the at least one protein is with the protein in its native state. In some embodiments, the at least one protein and ligand form a protein/ligand complex. In other embodiments, the interaction of the ligand with the at least one protein is with the protein where the protein still has a tertiary structure, but the tertiary structure is modified from the native state when the ligand interacts with the at least one protein. Once the sample solution is formed, a controlled heating is applied to the sample solution mixture. Fluorescent emissions from the fluorophore dye or fluorophore dye mixture are measured over a range of temperatures. The range of temperatures may include the temperatures both below and above an expected $T_m$ of the at least one protein. In some embodiments, the range of temperatures may include the temperatures in an extended range above an expected $T_m$. In other embodiments, the range of temperatures is pre-selected to be a standard range of temperatures. In some embodiments, measurements are made at the temperature the sample solution mixture exhibits before the controlled heating is applied and throughout the whole range of temperatures achieved by the sample solution mixture while heating is applied.

In some embodiments, a filter is used to provide the most minimally fluorescent signal when the at least one protein is still folded, and/or providing the most substantially fluorescent signal when the at least one protein unfolds, with or without a ligand being present. In some embodiments, a suitable filter may be an X4-M4 filter having Ex580±10 nm-Em 623±14 nM. In other embodiments, a suitable filter may be an X5-M5 filter having an Ex640±10 nm-Ex 680±14 nm.

Comparison of the fluorescence profile (also referred to as a protein melt curve) obtained from each individual experiment using a different buffer can be made to determine the conditions which the at least one protein is most stable. In some embodiments, the fluorescence profile is transformed mathematically to provide a first derivative trace, which permits identification of the $T_m$, observable as an inflection point.

In at least one embodiment, the sample solution mixture includes a surfactant. In at least one embodiment, the surfactant is present at a concentration that is at least the critical micelle concentration. In at least one embodiment, the sample solution mixture further includes a polyol. In at least one embodiment, the polyol is glycerol or a polysaccharide. In at least one embodiment, the methods can be performed without the measurement of the $T_m$ by comparing fluorescence from the fluorophore dye or dyes.

Methods of PTS using a single or mixture of dyes can be used to identify disease states in plasma. Protein Thermal Shift in plasma could potentially link signature melt curves to specific diseases and disease states, since plasma can contain disease specific concentrations of low molecular weight proteins, antibodies, miRNA and circulating nucleic acids and peptides. The potential also exists to look at signature melt curves from testing other body fluids, or samples concentrated from other body fluids, such as urine or sputum, to decipher melt profiles specific to disease states.

The methods can involve the steps of measuring the stability of a mixture of plasma proteins by forming a sample solution mixture including the mixture of plasma proteins from a patient and at least one fluorophore dye, applying a controlled heating to the mixture, measuring fluorescence emitted over a temperature range and identifying a first $T_m$ for the mixture of plasma proteins from a patient. A second $T_m$ can be calculated from the measured fluorescence obtained from a mixture of plasma proteins from a disease positive control and at least one fluorophore dye, and comparing the first $T_m$ and the second $T_m$, thereby analyzing the stability of the mixture of plasma proteins from a patient compared to the stability of the mixture of plasma proteins from a disease control. In at least one embodiment, the $T_m$ can be compared to a mixture of plasma proteins from a negative control.

In some embodiments the mixture of plasma proteins is each in its native state, which may include having a tertiary structure that is folded. In some embodiments, the sample solution mixture having the mixture of plasma proteins further includes a ligand which is potentially capable of interacting with at least one protein of the mixture of plasma proteins. In some embodiments, the interaction with the at least one protein is with the protein in its native state. In some embodiments, the at least one protein and ligand form a protein/ligand complex. In other embodiments, the interaction of the ligand with the at least one protein is with the protein where the protein still has a tertiary structure, but the tertiary structure is modified from the native state when the ligand interacts with the at least one protein.

Once the sample solution is formed, a controlled heating is applied to the sample solution mixture. Fluorescent emissions from the fluorophore dye or fluorophore dye mixture are measured over a range of temperatures. The range of temperatures may include the temperatures both below and above an expected $T_m$ of the mixture of plasma proteins. In some embodiments, the range of temperatures may include the temperatures in an extended range above an expected $T_m$. In other embodiments, the range of temperatures is pre-selected to be a standard range of temperatures. In some embodiments, measurements are made at the temperature the sample solution mixture exhibits before the controlled heating is applied and throughout the whole range of temperatures achieved by the sample solution mixture while heating is applied.

In some embodiments, a filter is used to provide the most minimally fluorescent signal when the at least one protein is still folded, and/or providing the most substantially fluorescent signal when the at least one protein unfolds, with or without a ligand being present. In some embodiments, a suitable filter may be an X4-M4 filter having Ex580±10 nm-Em 623±14 nM. In other embodiments, a suitable filter may be an X5-M5 filter having an Ex640±10 nm-Ex 680±14 nm.

Comparison of the fluorescence profile (also referred to as a protein melt curve) obtained from the mixture of plasma proteins from a patient and the fluorescence profile obtained from the mixture of plasma proteins from a disease positive control or a disease negative control sample can be made to determine the conditions which the at least one protein is most stable. In some embodiments, the fluorescence profile is transformed mathematically to provide a first derivative trace, which permits identification of the $T_m$, observable as an inflection point.

In at least one embodiment, the same fluorophore dye or mixture of dyes is used for both test sample (from a patient) and control sample. In at least one embodiment, the sample solution mixture includes a mixture of at least two fluorophore dyes. In at least one embodiment, the sample solution mixture includes a buffer. In at least one embodiment, the sample solution mixture includes a surfactant. In at least one embodiment, the surfactant is present at a concentration that is at least the critical micelle concentration. In at least one embodiment, the sample solution mixture further includes a polyol. In at least one embodiment, the polyol is glycerol or a polysaccharide. In at least one embodiment, the methods can be performed without the measurement of the $T_m$ by comparing fluorescence from the fluorophore dye or dyes.

Compositions.

Compositions for PTS assays are provided. The compositions can include at least one protein, and a mixture of at least two fluorophore dyes. The fluorophore dyes may provide a minimally fluorescent signal when they are in association with the protein in its native state or in a state where the at least one protein has a tertiary structure. The fluorophore dyes may provide a substantially increased fluorescent signal when the fluorophore dye is associated with the at least one protein in its unfolded state. The dyes can be any of the dyes provided herein. In at least one embodiment, when used in combination (of two, three, four, etc), the dyes are chosen such that they are spectrally distinct from each other. The mixture of at least two fluorescent dyes may be selected from any suitable dye as described above. In some embodiments, the fluorescent dye is a styryl dye. In at least one embodiment, the styryl dye has a structure of the formula Q-B-M, as described above. In some embodiments, the mixture of at least two fluorescent dyes includes a styryl dye as described in Table 2. Examples of dyes that can be used in combination in the compositions include, but are not limited to; Nile red and a styryl dye; Nile red and any mixtures of one or more of SYPRO® Orange. SYPRO® Red and SYPRO® Tangerine; one or more of SYPRO® Orange, SYPRO® Red, and SYPRO® Tangerine.

The at least one protein can be any of the proteins that are discussed herein. The at least one protein can be a single protein, a protein/ligand complex, a complex protein mixture (a mixture containing more than one protein, including, but not limited to human plasma), a membrane protein, a glycoprotein, and the like.

The composition may include a ligand. The ligand may be any suitable ligand as described here. In at least one embodiment, the ligand is a peptide, a polynucleotide, an aptamer, or a synthetic organic molecule.

The composition can include at least one buffer. The buffer can be chosen based on the type of protein or proteins in the composition to increase stability of the protein or proteins. The buffer can include a surfactant and/or a polyol, as described here.

Kits.

Kits including components for PTS assays can be provided. The kits can include a mixture of at least two fluorophore dyes. The fluorophore dyes can be dyes that provide at least a minimally fluorescent signal when they are in association with the protein in its native state. The fluorophore dyes can be dyes that provide a substantially increased fluorescent signal when the fluorophore dye is associated with the unfolded protein. The mixture of at least two fluorescent dyes may be selected from any suitable dye as described above. In some embodiments, when used in combination (of two, three, four, etc), the dyes are chosen such that they are spectrally distinct from each other. In some embodiments, the fluorescent dye includes a styryl dye. In at least one embodiment, the styryl dye has a structure of the formula Q-B-M (Formula I), as described above. In some embodiments, the mixture of at least two fluorescent dyes includes at least one styryl dye as described in Table 2. In some embodiments, the mixture of at least two fluorophore dyes include, but are not limited to; Nile red and a styryl dye of Formula I; Nile red and two or more styryl dyes of Formula I, or a mixture of more than two styryl dyes having a structure of Formula I. In some embodiments, the mixture of at least two fluorophore includes any mixtures of one or more of SYPRO® Orange, SYPRO® Red and SYPRO® Tangerine.

The at least one protein can be any of the proteins that are discussed herein. The at least one protein can be a single protein, a protein/ligand complex (e.g., an antibody/antigen complex), a complex protein mixture (e.g., human plasma), a membrane protein, a glycoprotein, etc. In at least one embodiment, the ligand is a peptide, a polynucleotide, or an aptamer.

The kit can include at least one buffer. The buffer can be chosen based on the type of protein or proteins in the composition or method to be appropriate candidates for use with the at least one protein. The buffer can further include a surfactant and/or a polyol. Alternatively, the kit may include a surfactant and/or a polyol packaged separately from the buffer.

In some embodiments, the kit does not contain the at least one protein. In other embodiments, one protein, which may serve as a control protein in the PTS assays methods, may be provided in the kit. If the kit contains the protein, the protein can be a single protein, a protein/ligand complex (e.g., an antibody/antigen complex), a complex protein mixture (e.g., human plasma), a membrane protein, or a glycoprotein.

In some embodiments, one or more ligands may be provided in the kit. The one or more ligands may be any suitable ligand as described here. The one or more ligands may be packaged separately from other components of the kits.

The kits may be provided for any of the methods described herein. For example, a kit can be provided for screening a specific protein and/or protein-ligand pair for aptamers that increase or decrease stability of the protein or protein-ligand pair.

In at least one embodiment there is provided a kit encompassing at least one or more dyes that are optimal for PTS of a specific protein, protein pair, protein-ligand pair, method, or mixture of proteins (e.g., plasma). The kit may also include one or more components for the PTS assay.

The kits of the present invention may also include instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

In at least one embodiment, the kits and assays are screening kits, diagnostic kits and/or kits for identifying the best fluorophore dye or dye mixture to be used for a specific protein, protein pair, protein ligand and/or conditions.

In at least one embodiment, a kit containing several fluorophore dyes that customers can use to find the one or mixture of dyes that works best for their protein/system is provided. This can allow researchers to screen their samples with these fluorophore dye mixtures, because the dyes bind differentially to different proteins and/or protein complexes. This differential binding can act as a "fingerprint" of that specific sample. Changes to the specific melt profile may be affected by proteins, ligands, buffers, and nucleic acids bound to the protein of interest. These changes can be correlated to a change in the biological state of the protein of interest and correlated to clinically relevant changes.

EXAMPLES

General:

In examples 1-5, SYPRO® Orange is used to show the utility of PTS to rapidly monitor protein thermo-stability and to identify optimal conditions that favor protein stability, including the investigation of protein-ligand interactions and mutations in protein sequences. In Examples 6-13, fluorophore dye mixtures are used to show improvement in the Protein Thermal Shift (PTS) profiles for complex proteins and/or protein mixtures over SYPRO® Orange alone. The optimal fluorophore dye mixture varies depending upon the proteins and the protein mixtures being melted. The methods can be used to study molecules that specifically recognize and bind to proteins (protein complexes) such as protein-antibody complexes, protein-peptide complexes, protein-lectin complexes, protein-aptamer complexes, etc.

The following fluorophore dyes are used in the examples: SYPRO® OrangeProtein Gel Stain (5000× Concentrate in DMSO), (Life Technologies Catalog #: S6650); SYPRO® Tangerine Protein Gel Stain (5000× Concentrate in DMSO), (Life Technologies Catalog #: S-12010); and SYPRO® Red Protein Gel Stain (5000× Concentrate in DMSO); (Life Technologies Catalog #: S6653). Alternatively, a mixture is used: SYPRO® Protein Gel Stain Starter Kit; S12012; Contains SYPRO® Tangerine, SYPRO® Red, SYPRO@Orange, (Life Technologies). Each of SYPRO® Tangerine, SYPRO® Red, and SYPRO® Orange provides fast, easy and sensitive detection of proteins in gels (down to 4 ng/band) without the need for fixatives. Staining is compatible with subsequent Western blotting, zymography, electroelution or mass spectrometry. Compared to Coomassie Brilliant Blue and silver staining, each of these dyes provides more consistent protein-to-protein staining and a much broader linear quantitation range (over three orders of magnitude). Stained proteins can be viewed with a standard UV or blue-light transilluminator or with a laser scanner. For optimal sensitivity with Polaroid film, use of the SYPRO® protein gel stain photographic filter (S-6656) is recommended. Nile Red (Life Technologies Catalog #: N1142) may be used to localize and quantitate lipids, particularly neutral lipid droplets within cells. Nile Red is almost non-fluorescent in water and other polar solvents but undergoes fluorescence enhancement and large absorption and emission blue shifts in nonpolar environments (excitation/emission maxima ~552/636 nm in methanol).

A variety of filters may be used with the dyes to identify the filter that permits the least amount of background fluorescence to be viewed in the measured fluorescence emission spectra of the PTS assays. In the following examples, an X4-M4 filter having Ex580±10 nm-Em 623±14 nM or an Ex5-M5 filter having an Ex640±10 nm-Ex 680±14 nm may be used.

Applied Biosystems® Real-time PCR Systems instruments, as described above, are used to plot the fluorescence data throughout the thermal melt, generating a fluorescence profile specific to the protein of interest within the test buffer environment or in the presence of a test ligand. A MATLAB based TmTool™ which utilizes the Boltzmann equation to calculate the $T_m$ of the protein from the fluorescence melt plot is used to process the raw data recorded with the instrument.

Example 1: Analysis of Protein Thermal Shift Assays for Protein-Ligand Complexes Using T4 DNA Ligase-ATP In Example 1, the utility of the PTS assay in buffer and ligand screening for T4 DNA ligase is demonstrated. It was found that the $T_m$ of T4 DNA ligase shifted in the presence of ATP.

T4 DNA ligase is prepared in phosphate buffered saline (PBS; 137 mM NaCl, 10 mM Phosphate. 2.7 mM KCl, pH 7.4) and 5% glycerol at a concentration of 3 mg/ml of protein. T4 DNA ligase samples are prepared using SYPRO® Orange with and without ligand (ATP at 10 mM concentration). SYPRO® Orange dye solution is prepared as a 1000× stock from a 5000× stock solution in DMSO, then diluted to a 10× stock solution using 100 mM Potassium phosphate buffer. The SYPRO® Orange-protein reaction mixture is prepared by using 1 μl of the protein solution, 2 μl of the 10× dye solution, and 171 μl of the PTS buffer. Quadruplicate samples for each protein-dye mixture are run on a ViiA™ 7 qPCR instrument (Life Technologies, Inc.) and analysis using Protein Thermal Shift™ software (Life Technologies Inc.). The run time conditions are: a temperature hold at 20° C. for one minute followed by a thermal ramp of 0.05° C. with continuous data collection to 95° C., followed by a 1 minute hold at the final temperature.

Figure 2A:
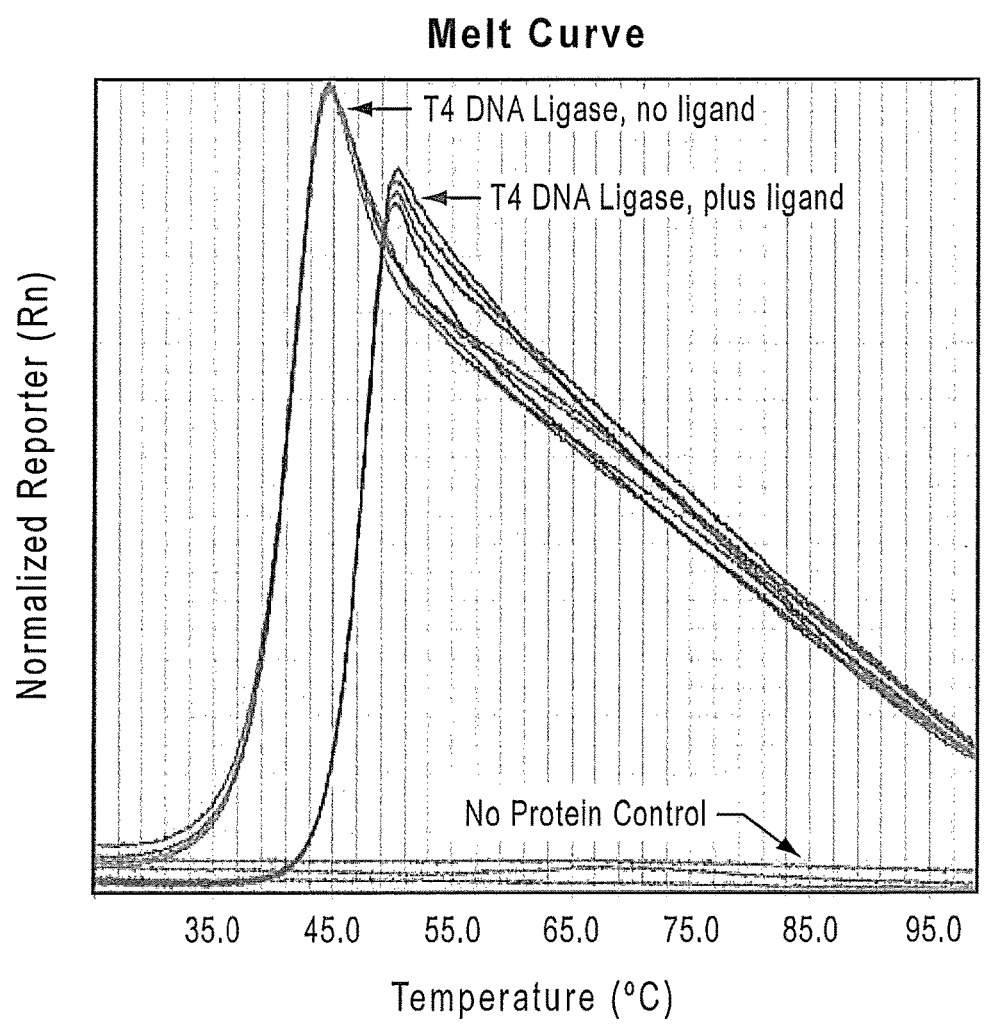
FIGS. 2A through 2B show the effect of ligand interaction on protein stability using PTS according to various embodiments of systems and methods of the present teachings.
Figure 2B:
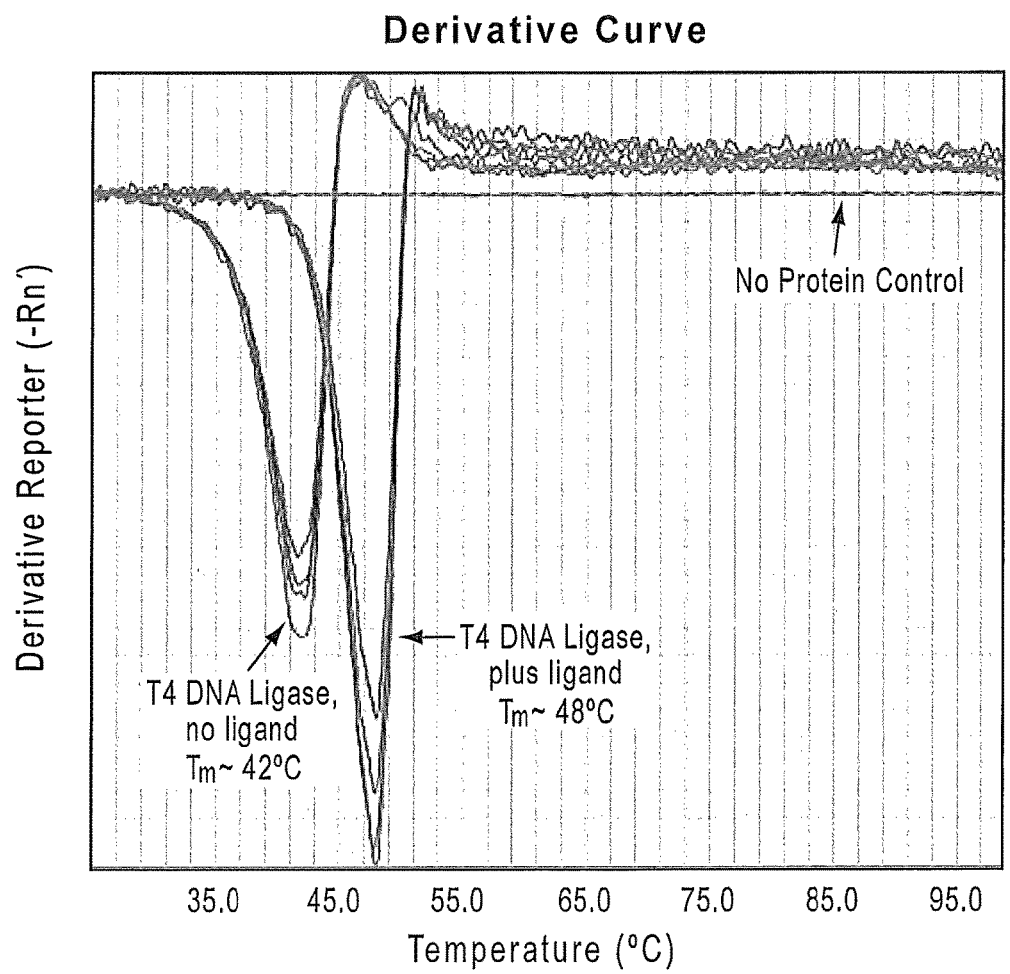

FIGS. 2A and 2B provide melt curve data generated on a Viia™7 Real Time PCR System showing the effect of a specific ligand (ATP) on protein stability (T4 DNA Ligase). The melt curves are shown in FIG. 2A and the derivative of the melt curves are shown in FIG. 2B. In FIG. 2A, the melt curves of T4 DNA Ligase with no ligand present. T4 DNA Ligase with ligand (ATP), and No Protein Control are shown. From the rightward shift to higher temperature (X axis) in the leading edge of the curve comparing the uncomplexed Ligase to the complexed Ligase, the stabilization of T4 DNA Ligase is clearly evident. The $T_m$ of uncomplexed T4 DNA Ligase is found to be about 42° C. and that of the complexed T4 DNA Ligase shifts to about 48° C., as shown in the Derivative curve of FIG. 2B. This shift is a clear demonstration of the increased stability upon addition of ATP.

Example 2: Method of Calculating $T_m$ from Protein Thermal Shift Assays

Figure 3A:
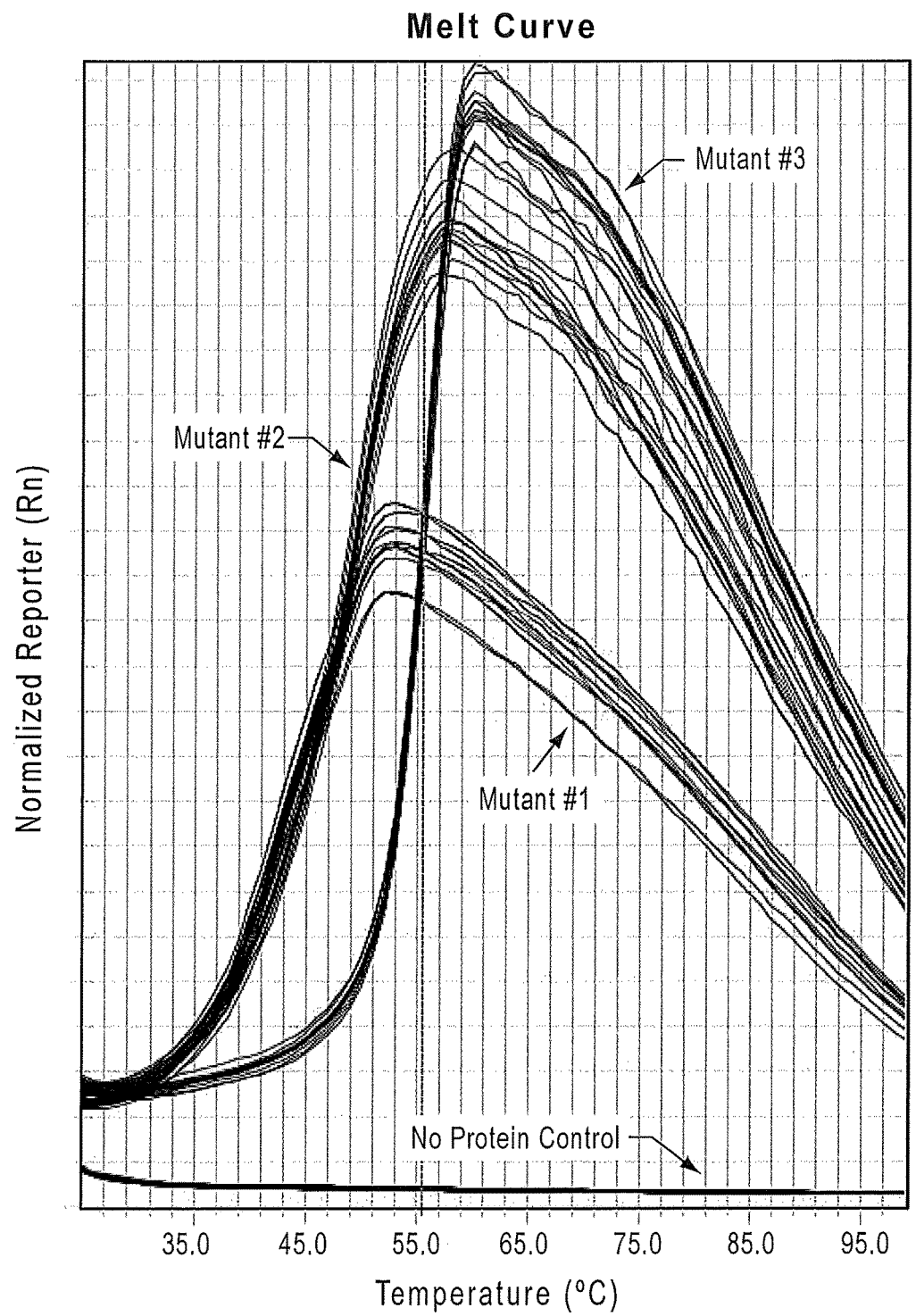
FIGS. 3A through 3C show the effect of point mutations on PTS according to various embodiments of systems and methods of the present teachings.
Figure 3B:
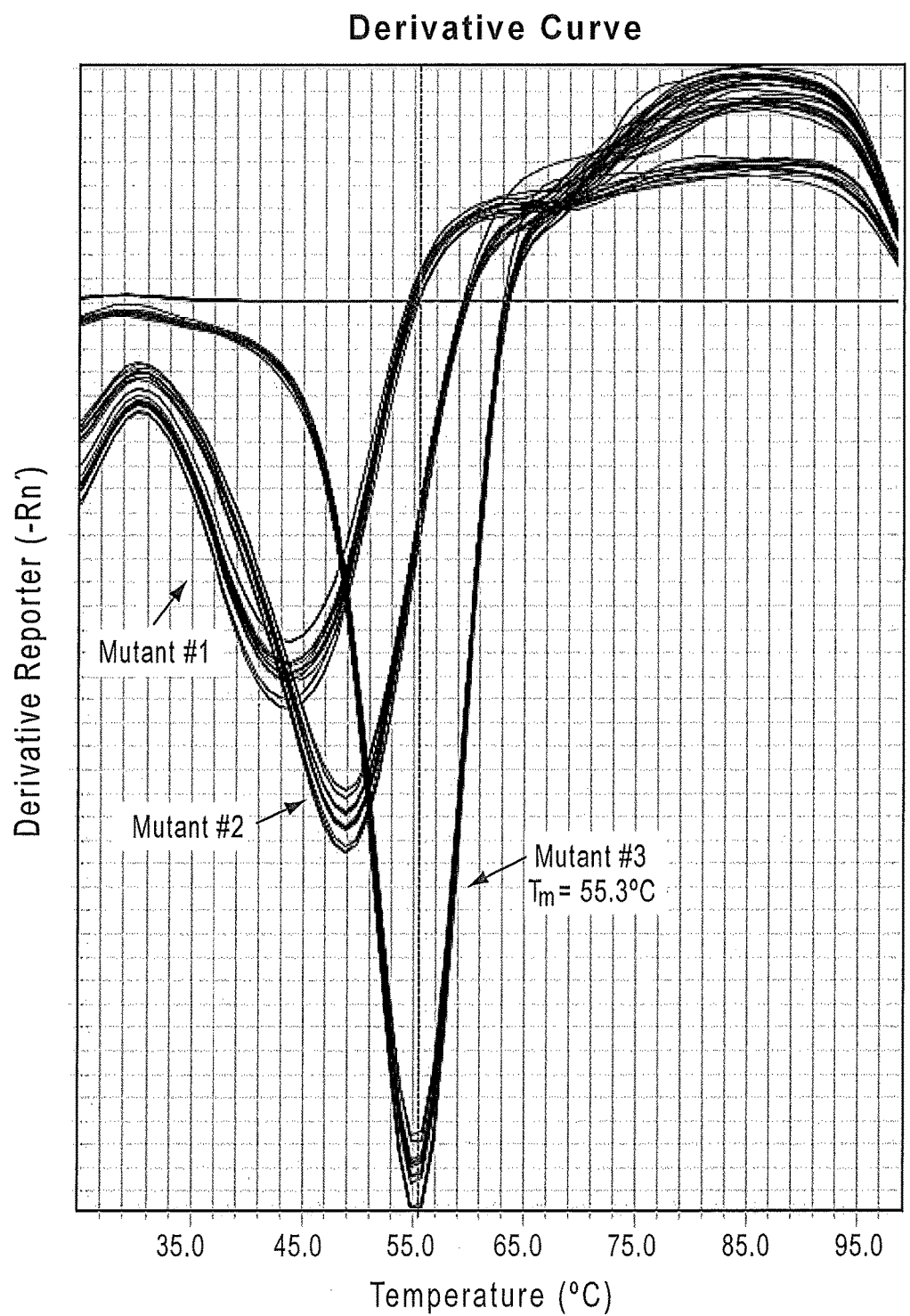
Figure 3C:
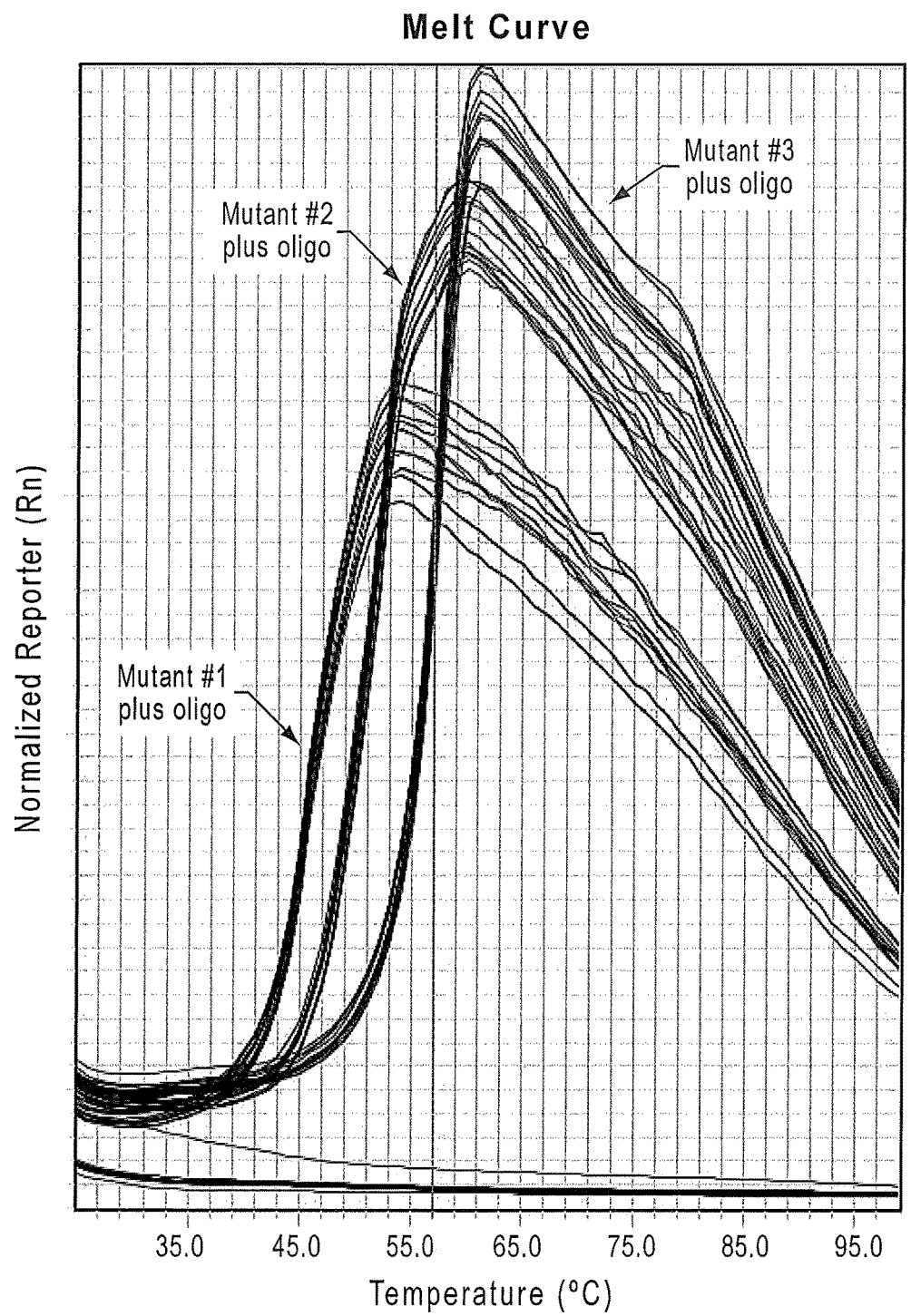

FIGS. 3A through 3C illustrate the method of calculating $T_m$ from a typical PTS. The MATLAB based TmTool™ calculates the $T_m$ of the protein from the shape of the fluorescence plot in FIG. 3a. The thermo-stability of RecA in different buffer and salt conditions is compared and the region of interest is fitted to the Boltzmann equation. RecA is prepared in phosphate buffered saline (PBS; 137 mM NaCl, 10 mM Phosphate, 2.7 mM KCl, pH 7.4) and 5% glycerol at a concentration of 3 mg/ml of protein. SYPRO® Orange dye solution is prepared as a 1000× stock from a 5000× stock solution in DMSO, then diluted to a 10× stock solution with PTS buffer.

TABLE 4

Buffer Compositions.

| Buffer ID # | Sodium Chloride concentration in mM | | | |
|---|---|---|---|---|
| | 0 mM | 50 mM | 100 mM | 150 mM |
| A. 100 mM Sodium Citrate, pH 5.5 | A1 | A2 | A3 | A4 |
| B. 100 mM Potassium Phosphate, pH 6.0 | B1 | B2 | B3 | B4 |
| C. 100 mM Potassium Phosphate, pH 7.0 | C1 | C2 | C3 | C4 |
| D. 100 mM HEPES, pH 7.5 | D1 | D2 | D3 | D4 |

Experimental buffers are made as shown in Table 4. The SYPRO® Orange-protein Protein Thermal Shift Assay reaction mixture is prepared by using 1 µl of the protein solution, 2 µl of the 10× dye solution, and 17 µl of each of experimental buffer solutions A1-A4, B1-B4, C1-C4, and D1-D4. Samples for each protein-dye mixture are run on a ViiA™ 7 qPCR instrument (Life Technologies, Inc.) and analysis using Protein Thermal Shift™ software (Life Technologies Inc.). The run time conditions are: a temperature hold at 20° C. for one minute followed by a thermal ramp of 0.05° C. with continuous data collection to 95° C., followed by a 1 minute hold at the final temperature.

TABLE 5

Results of buffer screen including $T_m$ s.

| Protein | Buffer ID | NaCl in mM | $T_m$ in ° C. | Buffer ID with increase [NaCl] |
|---|---|---|---|---|
| RecA | Buffer-A 100 mM Sodium Citrate, pH 5.5 | 0 mM NaCl | 42.2 | A1 |
| | | 50 mM NaCl | 41.7 | A2 |
| | | 100 mM NaCl | 42.1 | A3 |
| | | 150 mM NaCl | 41.6 | A4 |
| | Buffer-B 100 mM Potassium Phosphate, pH 6.0 | 0 mM NaCl | 41.8 | B1 |
| | | 50 mM NaCl | 41.2 | B2 |
| | | 100 mM NaCl | 41.2 | B3 |
| | | 150 mM NaCl | 41.1 | B4 |
| | Buffer-C 100 mM Potassium Phosphate, pH 7.0 | 0 mM NaCl | 46.8 | C1 |
| | | 50 mM NaCl | 46.6 | C2 |
| | | 100 mM NaCl | 46 | C3 |
| | | 150 mM NaCl | 45.7 | C4 |

The Applied Biosystems' TmTool™ calculator provides the protein $T_m$ calculated via Boltzmann curve-fitting. The results are shown in Table 5, and demonstrate that buffer C provides the best stabilization for RecA in comparison to buffer A and buffer B. Salts within a storage or handling buffer interact with the charged amino acids of a protein, ultimately affecting the stability of the resulting protein tertiary structure. Thus, the methods can be used to identify salt and pH concentrations best suited for stability of a protein as well as conditions for protein storage, crystallography, etc. The Boltzmann equation used is:

$$F(T) = F(\text{pre}) + \frac{[F(\text{post}) - F(\text{pre})]}{1 + e^{\frac{(T_m - T)}{C}}}.$$

Example 3: Effect of Point Mutations on PTS. Effect of Complexation with a Ligand An assay was set up to determine whether a PTS Assay can differentiate between point mutations in a protein that affect the thermal stability of the protein.

Figure 3D:
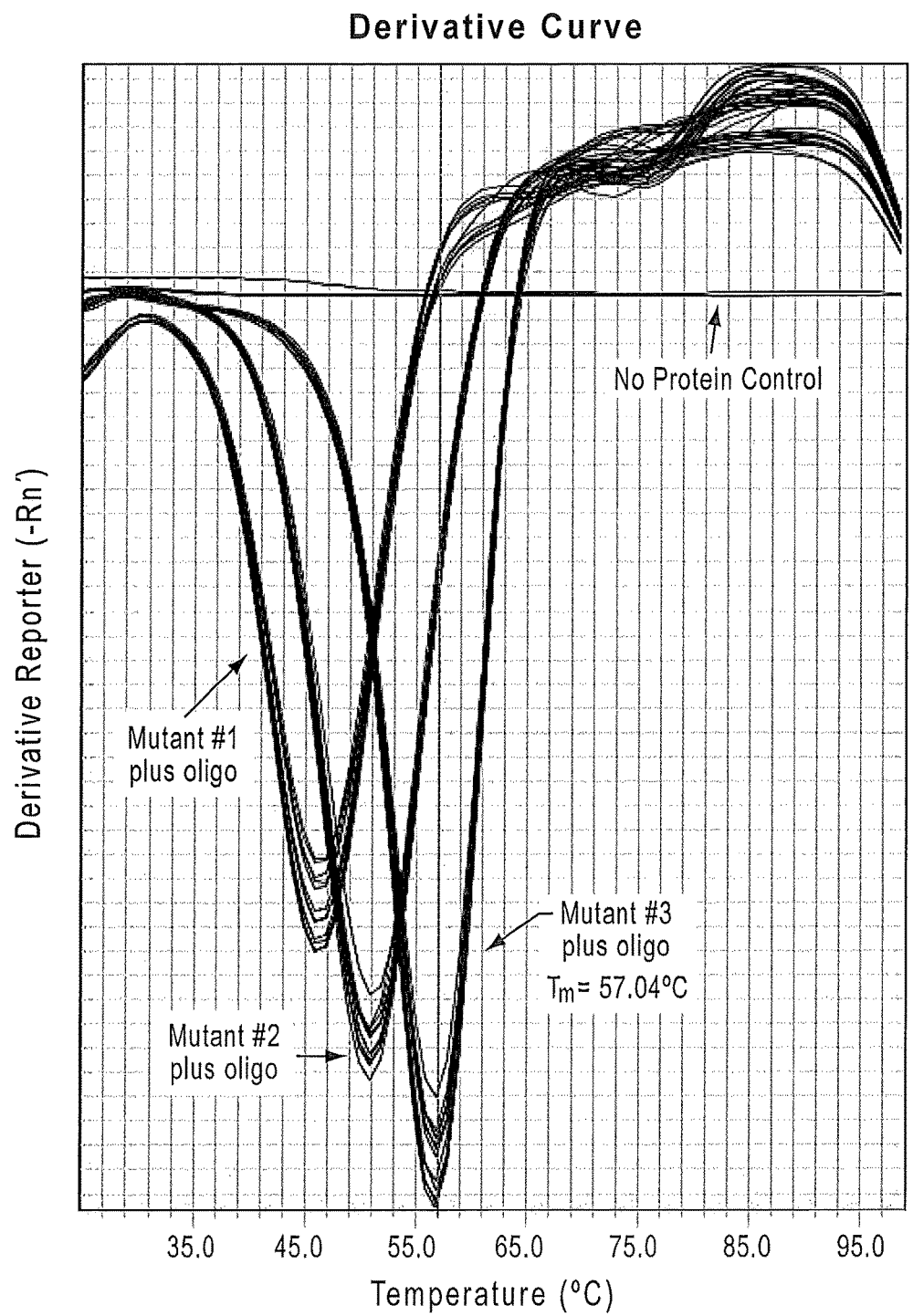
FIG. 3D shows the first derivative graph of the PTS of FIG. 3C.

In FIGS. 3A through 3D, the PTS data (generated on a StepOnePlus™ instrument (Life Technologies, Inc.)) shows the normalized reporter and derivative melt profiles from experimental SuperScript®II (SSII) and SuperScript®III (SSIII) mutants. Data was collected at 1° C. intervals from 25° C. through to 99° C. FIG. 3A shows a melt curve with a normalized reporter for three point mutants of SSII and SSSIII. FIG. 3B shows the first derivative graph of the PTS of FIG. 3A, demonstrating that an averaged $T_m$ of 43.8° C. is found for a first point mutant, a $T_m$ of 49.2° C. for a second point mutant, and 55.5° C. for a third point mutant for SSI or SSIII. FIG. 5C shows a melt curve with a normalized reporter for each of the above point mutants complexed with an oligonucleotide. FIG. 3D shows the first derivative graph of the PTS of FIG. 3C, demonstrating an averaged $T_m$ of 46.3° C. for the first point mutant complexed with oligo; an averaged $T_m$ of 51.1° C. for the second point mutant complexed with oligo, and an averaged $T_m$ of 57.0° C. is found for the third point mutant complexed with oligo.

The results show that the method can differentiate between point mutations in a protein that affect thermal stability of the protein, as the shift to higher $T_m$ can be clearly seen in FIGS. 3B and 3D. Thus, the method can be used to assay or analyze the affects of mutations on the stability of a protein. Further, the methods can be used to assay or analyze the affect of mutations on the stability of binding of a protein with a ligand such as an oligonucleotide.

Example 4: Antibody Binding Increases Protein Thermal Stability

Figure 4A:
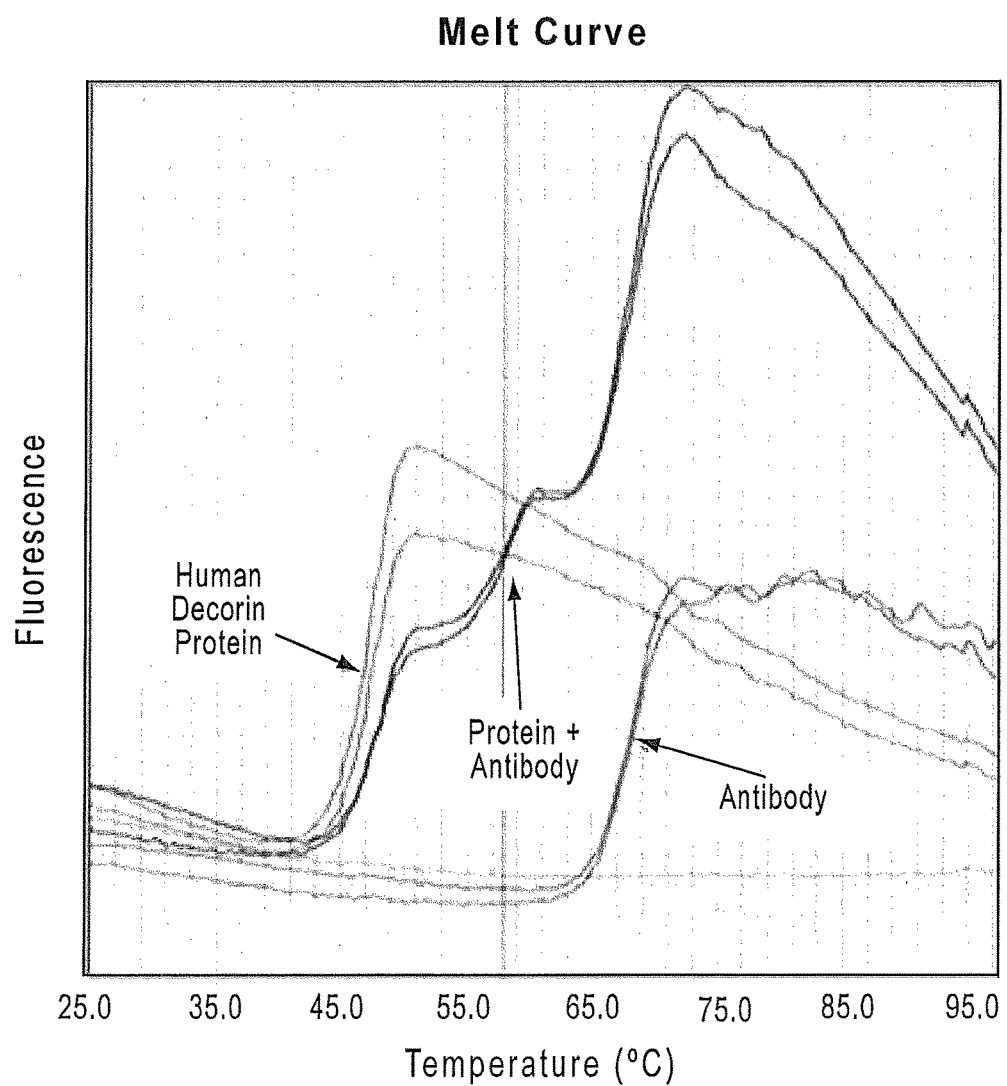
FIGS. 4A through 4B show the effect of antibody binding to a protein (e.g., decorin) to increase protein thermal stability.
Figure 4B:
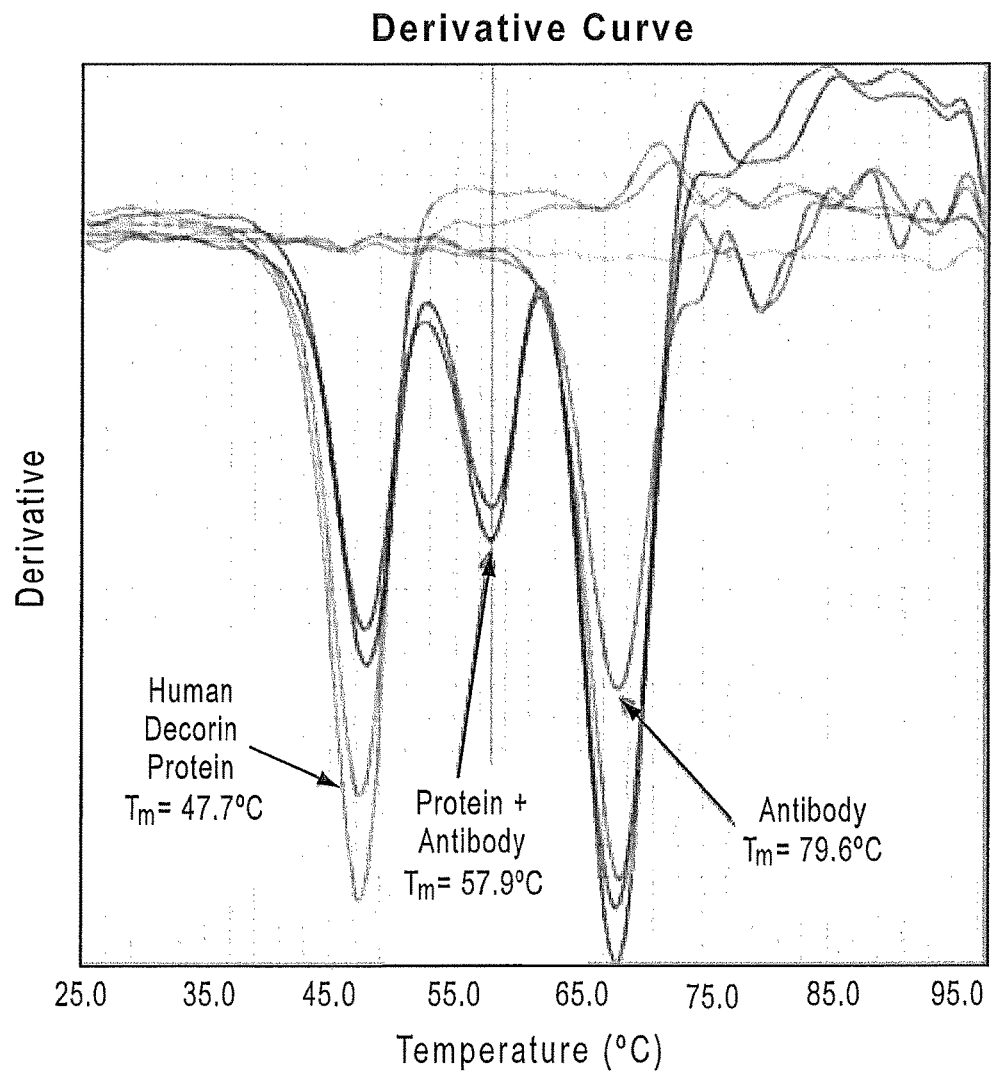

An assay was performed to identify whether PTS can be used to analyze binding of an antibody to its ligand. The method is performed using buffer and reaction conditions as described in EXAMPLE 1. Human Decorin Protein (P/N 143-DE (R&D Systems), a Monoclonal Anti-Human Decorin Antibody (P/N MAB1432 (R&D Systems)), and a mixture of Decorin and Anti-Human Decorin Antibody are each subjected to PTS. FIGS. 4A and 4B show that binding of the monoclonal Ab (anti-human Decorin protein) to the human Decorin protein resulted in a shift in $T_m$ of greater than 10° C., demonstrating effective detection of Ab binding to the protein. Human Decorin has a $T_m$ of 47.7° C., the isolated antibody has a $T_m$ of 79.6° C., and the protein/antibody bound complex has a $T_m$ of 57.9° C. This PTS experiment is performed on the 7500 Fast Real-Time PCR Instrument (non-expert mode).

Example 5: Method of Screening Fluorophore Dye Mixtures and Buffer Conditions Using Bovine Serum Albumin (BSA)

The fluorescent dye formulations are prepared as follows: The formulation tubes are labeled according to the formulation number in Table 6. The indicated amount of dimethylsulfoxide (DMSO) is pipetted into each tube. The remaining formulation components were then added into each tube, as indicated in the chart. Each tube was vortexed on high speed for 10 seconds and then pulse centrifuged. The fluorescent dye mixtures were stored at room temperature, in the dark. Each PTS dye mixture was considered to be 100× that of the final concentration in a PTS reaction.

TABLE 6

Dye formulations.

| Dye Mixture | | DMSO | Nile Red | SYPRO ® Orange | SYPRO ® Red | SYPRO ® Tangerine |
|---|---|---|---|---|---|---|
| | 1 | 90 | 0 | 5 | 0 | 5 |
| Center-point | 2 | 90 | 2.5 | 2.5 | 2.5 | 2.5 |
| | 3 | 95 | 0 | 0 | 5 | 0 |
| | 4 | 90 | 5 | 0 | 0 | 5 |
| | 5 | 80 | 5 | 5 | 5 | 5 |
| Center-point | 6 | 90 | 2.5 | 2.5 | 2.5 | 2.5 |
| | 7 | 85 | 0 | 5 | 5 | 5 |
| | 8 | 85 | 5 | 0 | 0 | 0 |
| | 9 | 95 | 0 | 0 | 0 | 5 |
| SYPRO ® Orange | 10 | 95 | 0 | 5 | 0 | 0 |
| | 11 | 95 | 5 | 0 | 0 | 0 |
| | 12 | 90 | 0 | 0 | 5 | 5 |
| | 13 | 85 | 5 | 0 | 5 | 5 |
| | 14 | 85 | 5 | 5 | 5 | 0 |
| | 15 | 90 | 5 | 5 | 0 | 0 |
| | 16 | 95 | 0 | 0 | 5 | 0 |

The following buffers were prepared: A3 (100 mM Sodium Citrate, pH 5.5, 150 mM NaCl), B3 (100 mM Potassium Phosphate, pH 6.0, 100 mM NaCl), C3 (100 mM Potassium Phosphate, pH 7.0, 100 mM NaCl), D3 (100 mM Hepes, pH 7.5, 100 mM NaCl), E3 (50 mM Tris, pH 8.0, 100 mM NaCl).

The PTS reactions were set up in a 96-well plate, on ice. BSA in a 10 mg/mL stock was diluted 1:1 with 50% glycerol to create a working concentration of 5 mg/mL BSA, in 25% glycerol. Using a multi-channel pipette, the reactions were set up as shown in Table 7.

TABLE 7

PTS reaction set up.

| Buffer A3 2 ul BSA | | Buffer B3 2 ul BSA | | Buffer C3 2 ul BSA | | Buffer D3 2 ul BSA | | Buffer E3 2 ul BSA | | No protein control, Buffer C3 | |
|---|---|---|---|---|---|---|---|---|---|---|---|
| Dye Mix 1 | Dye Mix 9 | Dye Mix 1 | Dye Mix 9 | Dye Mix 1 | Dye Mix 9 | Dye Mix 1 | Dye Mix 9 | Dye Mix 1 | Dye Mix 9 | Dye Mix 1 | Dye Mix 9 |
| Dye Mix 2 | Dye Mix 10 | Dye Mix 2 | Dye Mix 10 | Dye Mix 2 | Dye Mix 10 | Dye Mix 2 | Dye Mix 10 | Dye Mix 2 | Dye Mix 10 | Dye Mix 2 | Dye Mix 10 |
| Dye Mix 3 | Dye Mix 11 | Dye Mix 3 | Dye Mix 11 | Dye Mix 3 | Dye Mix 11 | Dye Mix 3 | Dye Mix 11 | Dye Mix 3 | Dye Mix 11 | Dye Mix 3 | Dye Mix 11 |
| Dye Mix 4 | Dye Mix 12 | Dye Mix 4 | Dye Mix 12 | Dye Mix 4 | Dye Mix 12 | Dye Mix 4 | Dye Mix 12 | Dye Mix 4 | Dye Mix 12 | Dye Mix 4 | Dye Mix 12 |
| Dye Mix 5 | Dye Mix 13 | Dye Mix 5 | Dye Mix 13 | Dye Mix 5 | Dye Mix 13 | Dye Mix 5 | Dye Mix 13 | Dye Mix 5 | Dye Mix 13 | Dye Mix 5 | Dye Mix 13 |
| Dye Mix 6 | Dye Mix 14 | Dye Mix 6 | Dye Mix 14 | Dye Mix 6 | Dye Mix 14 | Dye Mix 6 | Dye Mix 14 | Dye Mix 6 | Dye Mix 14 | Dye Mix 6 | Dye Mix 14 |
| Dye Mix 7 | Dye Mix 15 | Dye Mix 7 | Dye Mix 15 | Dye Mix 7 | Dye Mix 15 | Dye Mix 7 | Dye Mix 15 | Dye Mix 7 | Dye Mix 15 | Dye Mix 7 | Dye Mix 15 |
| Dye Mix 8 | Dye Mix 16 | Dye Mix 8 | Dye Mix 16 | Dye Mix 8 | Dye Mix 16 | Dye Mix 8 | Dye Mix 16 | Dye Mix 8 | Dye Mix 16 | Dye Mix 8 | Dye Mix 16 |

The assays are run on a ViiA™ 7 qPCR instrument (Life Technologies, Inc.) and analyzed using Protein Thermal Shift™ software (Life Technologies Inc.). The run time conditions are: a temperature hold at 20° C. for one minute followed by a thermal ramp of 0.05° C. with continuous data collection to 95° C., followed by a 1 minute hold at the final temperature.

Figure 5A:
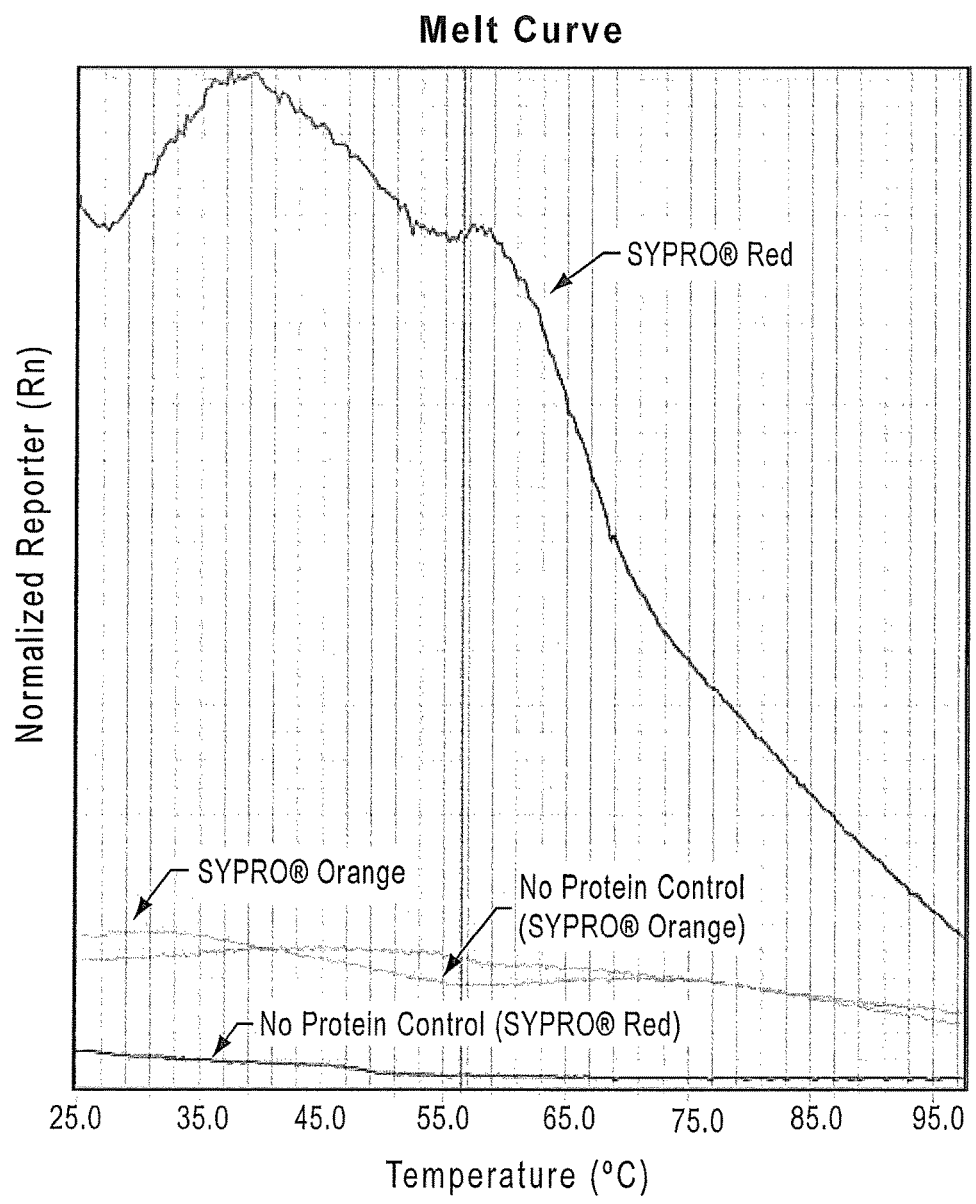
FIGS. 5A through 5C show the effect of differing dyes and buffer mixtures upon observed PTS curves and first derivatives thereof for bovine serum albumin (BSA).
Figure 5B:
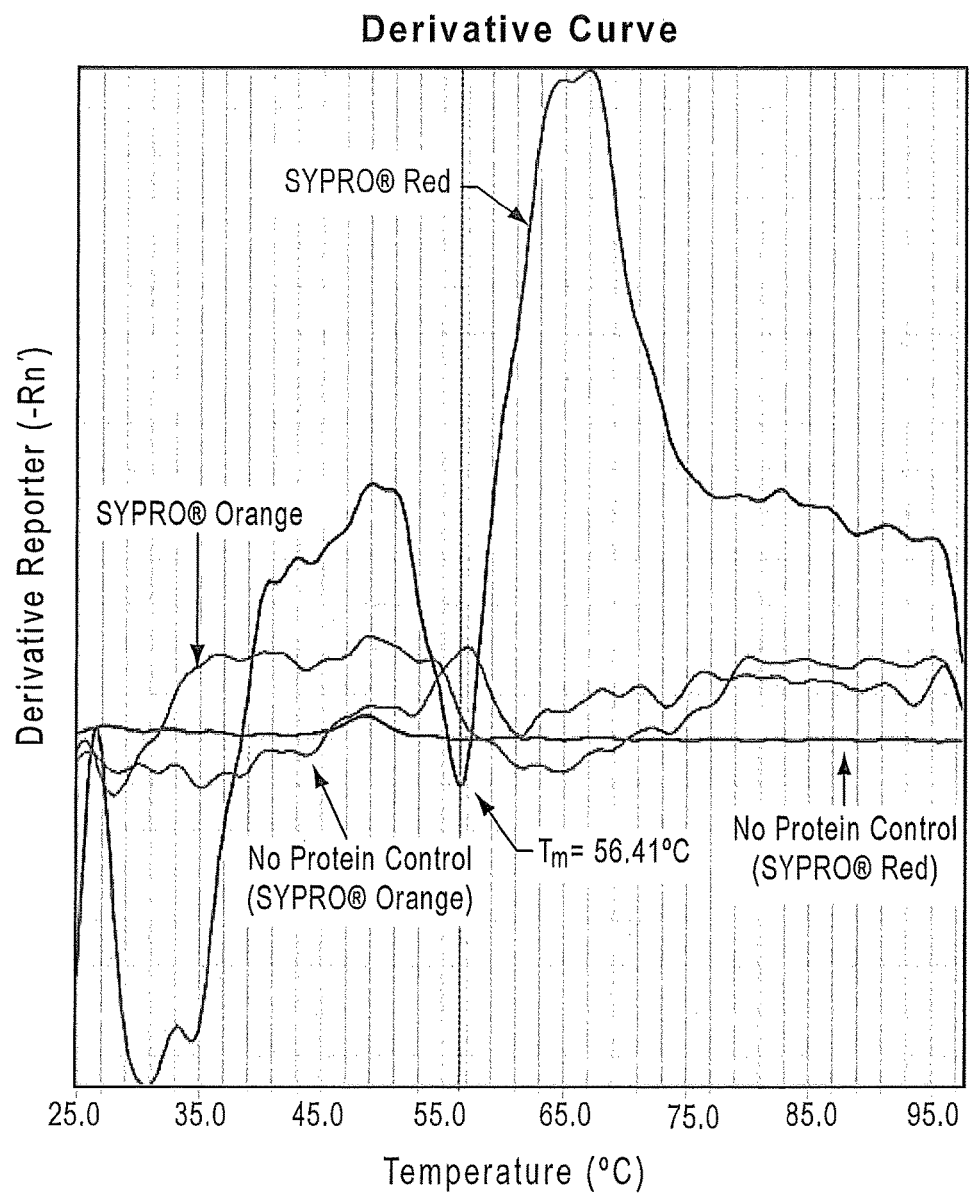
Figure 5C:
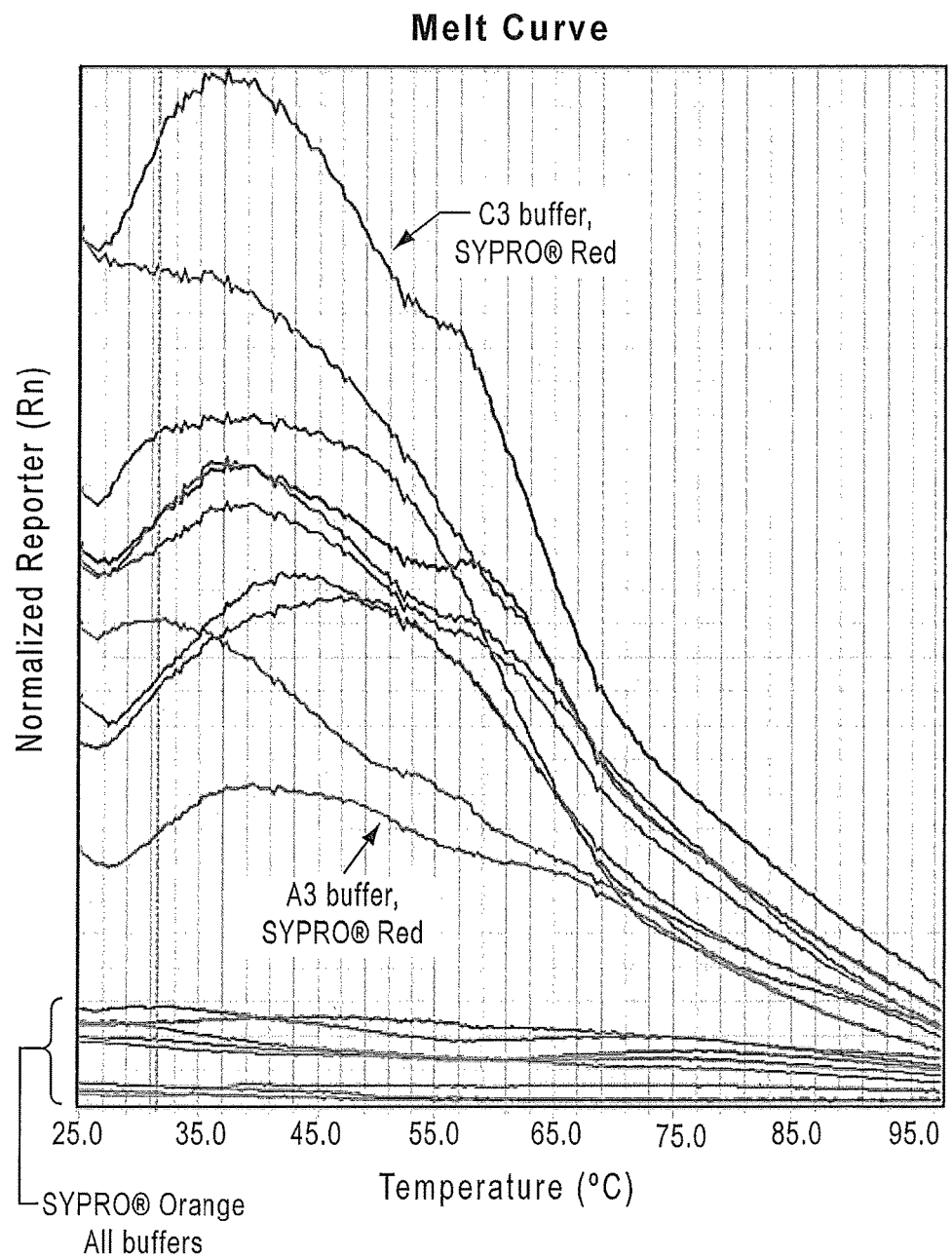

FIGS. 5A (thermal melt curve) and 5B (first derivative of the raw thermal melt curve data) show that Bovine Serum Albumin exhibits a high background in the PTS curve with SYPRO® Orange (dye formulation 10) in A3 buffer, while the use of SYPRO® Red (dye formulation 3) with A3 buffer in the thermal melt assay provides an informative PTS Curve, in the presence of an X4-M4 filter. In FIG. 5B, where the $T_m$ can be identified at the inflection point. Thus, SYPRO® Red is a significantly better fluorophore dye for thermal melt assays of BSA, yielding a better PTS curve, than SYPRO® Orange.

FIG. 5C shows melt curves for BSA using a variety of buffers (A3, B3, C3, D3, and E3) where NPC is a no protein control. The melt curves for BSA, SYPRO® Red in C3 buffer and in A3 buffer are specifically pointed out to show the variance in signal obtained. The melt curves for BSA, SYPRO® Orange, in any of the buffers, are shown in a low band at the bottom of the melt curve graph. FIG. 5C shows that dye mixtures including SYPRO® Red provide meaningful melt curve while the use of SYPRO® Orange, across a selection of buffers cannot provide useful data.

Example 7: PTS of Human Plasma Comparing SYPRO® Red to SYPRO® Orange

The dye mixtures are formulated to be 100× final PTS reaction concentration. 100 µl of each 100× dye mixture is prepared for dye mixtures 1-16 of Table 8.

TABLE 8

Dye mixture formulations

| Dye Mixture | | Nile Red | SYPRO® Orange | SYPRO® Red | SYPRO® Tangerine |
|---|---|---|---|---|---|
| | 1 | 0 | 5 | 0 | 5 |
| Center-point | 2 | 2.5 | 2.5 | 2.5 | 2.5 |
| | 3 | 0 | 0 | 5 | 0 |
| | 4 | 5 | 0 | 0 | 5 |
| | 5 | 5 | 5 | 5 | 5 |
| Center-point | 6 | 2.5 | 2.5 | 2.5 | 2.5 |
| | 7 | 0 | 5 | 5 | 5 |
| | 8 | 5 | 0 | 0 | 0 |
| | 9 | 0 | 0 | 0 | 5 |
| SYPRO® Orange | 10 | 0 | 5 | 0 | 0 |
| | 11 | 5 | 0 | 0 | 0 |
| | 12 | 0 | 0 | 5 | 5 |
| | 13 | 5 | 0 | 5 | 5 |
| | 14 | 5 | 5 | 5 | 0 |
| | 15 | 5 | 5 | 0 | 0 |
| | 16 | 0 | 0 | 5 | 0 |

The PTS reactions are set up without dye as shown in Table 9:

TABLE 9

Protein Thermal Shift reaction set up

| | 1X | 17X |
|---|---|---|
| .4X Buffer | 35 ul | 595 ul |
| Human plasma (10X = ~3 mg/ml) | 14 ul | 238 ul |
| water | 89.7 ul | 1524.9 ul |
| | 138.6 ul/well | |

The reactions are mixed with a gentle vortex and 138.6 µl are aliquoted per mix/well. 1.4 ml 100× dye is added to the mix according to the plate map (see Table 9).

The PTS assay is performed as in Example 5 except the buffers used were B3 (1×: 100 mM Potassium Phosphate, pH 6.0, 100 mM NaCl) and C3 (1×: 100 mM Potassium Phosphate, pH 7.0, 100 mM NaCl).

Figure 6A:
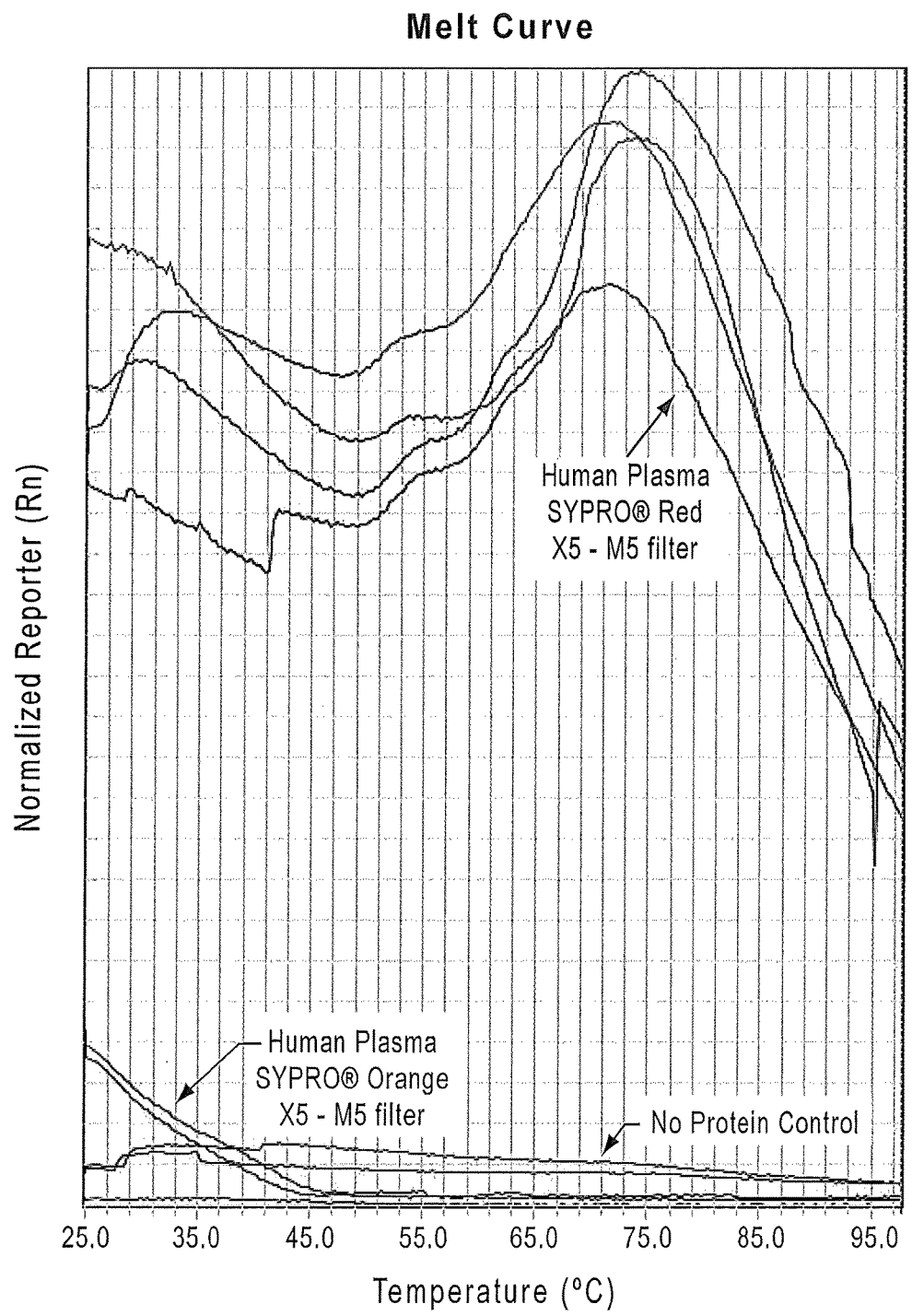
FIGS. 6A through 6D.
Figure 6B:
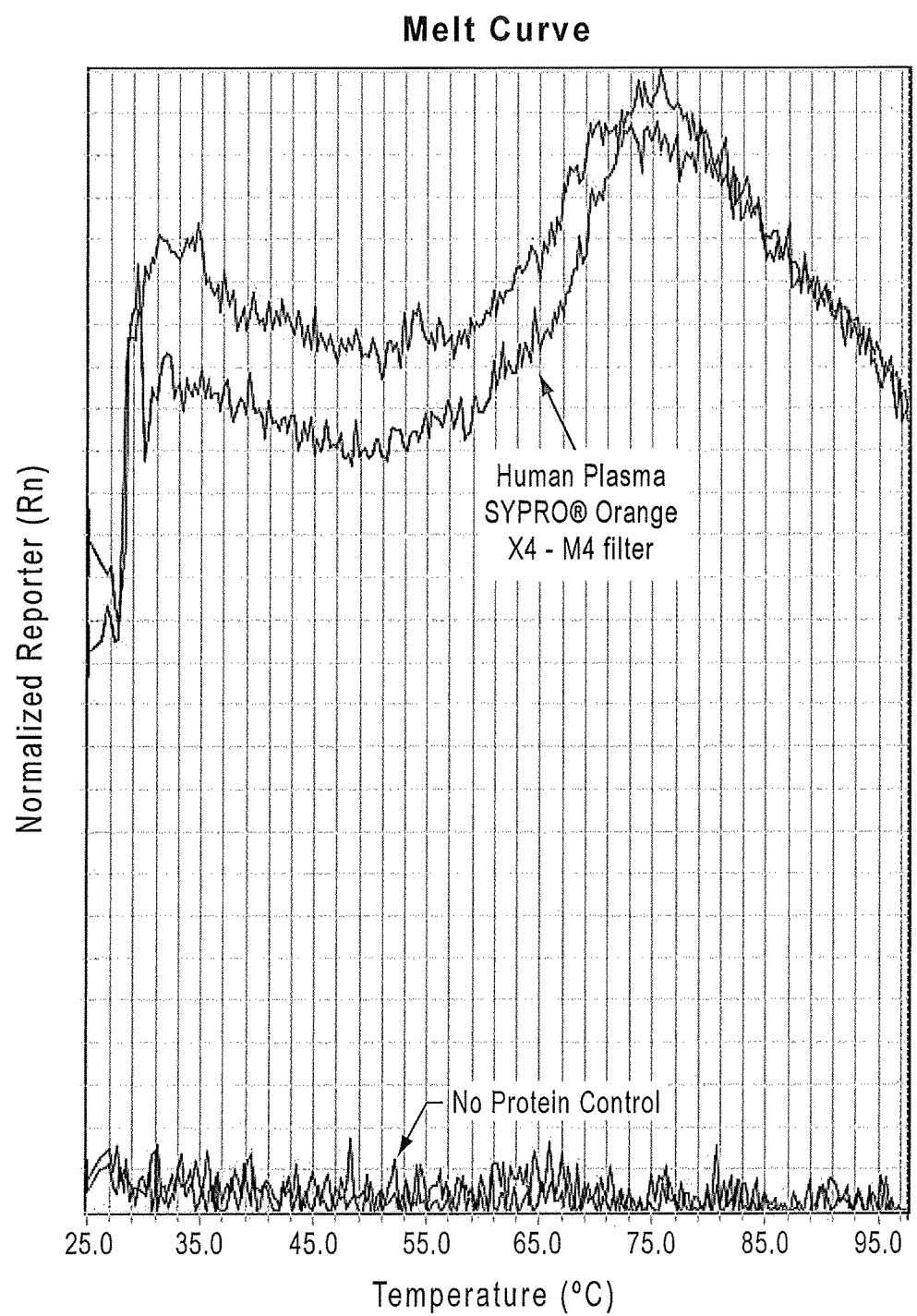
Figure 6C:
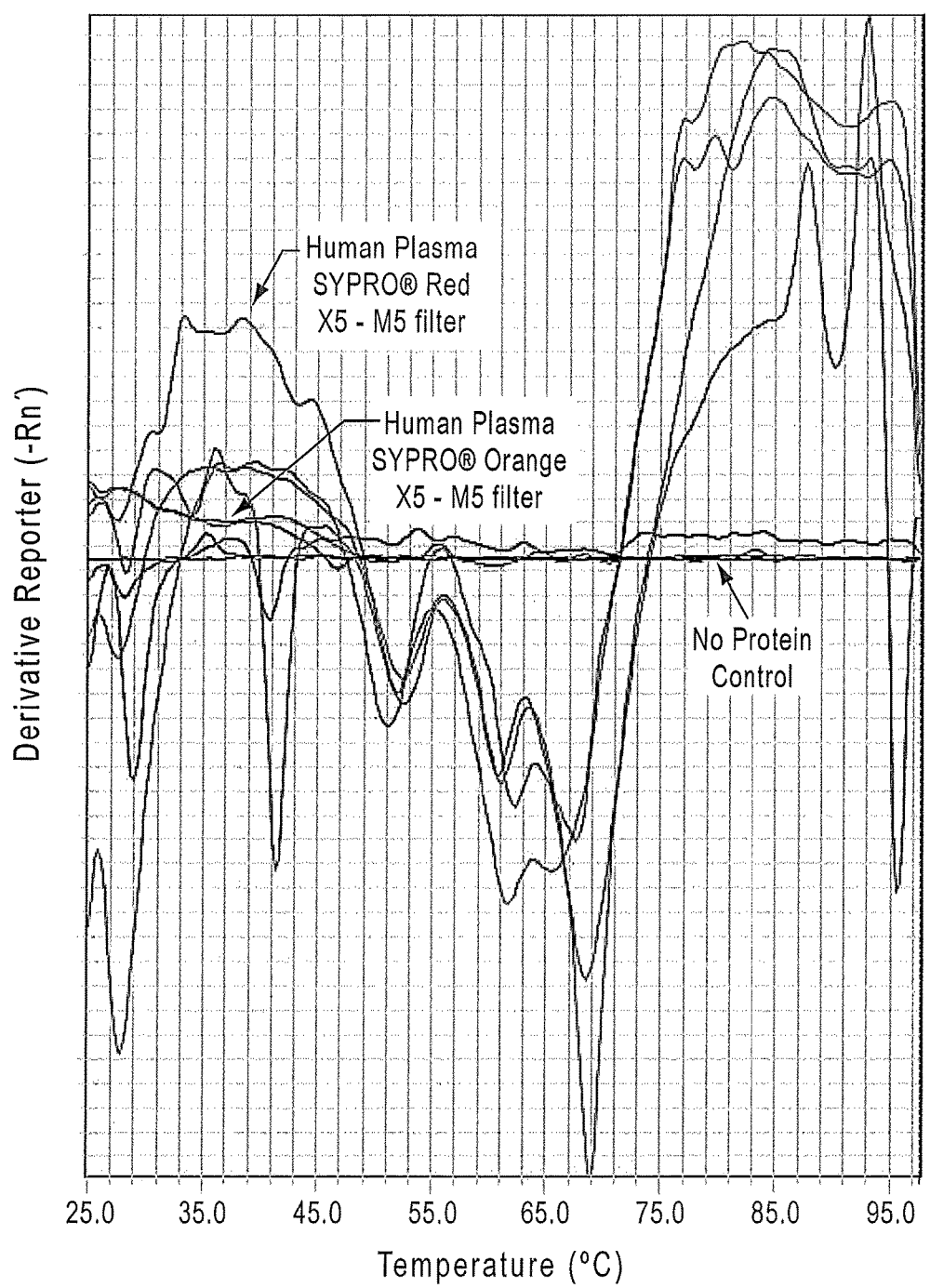
Figure 6D:
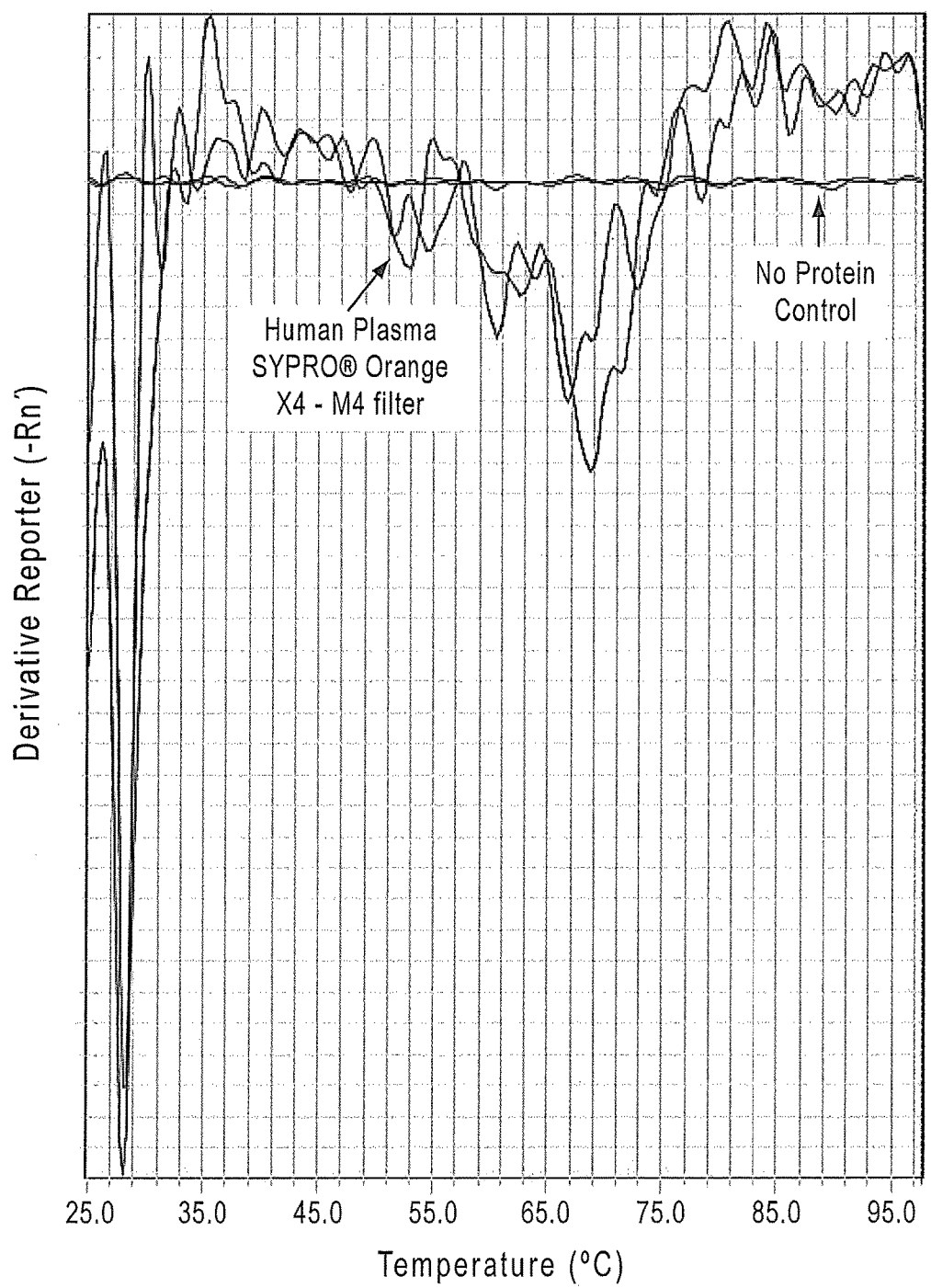
Figure 8A:
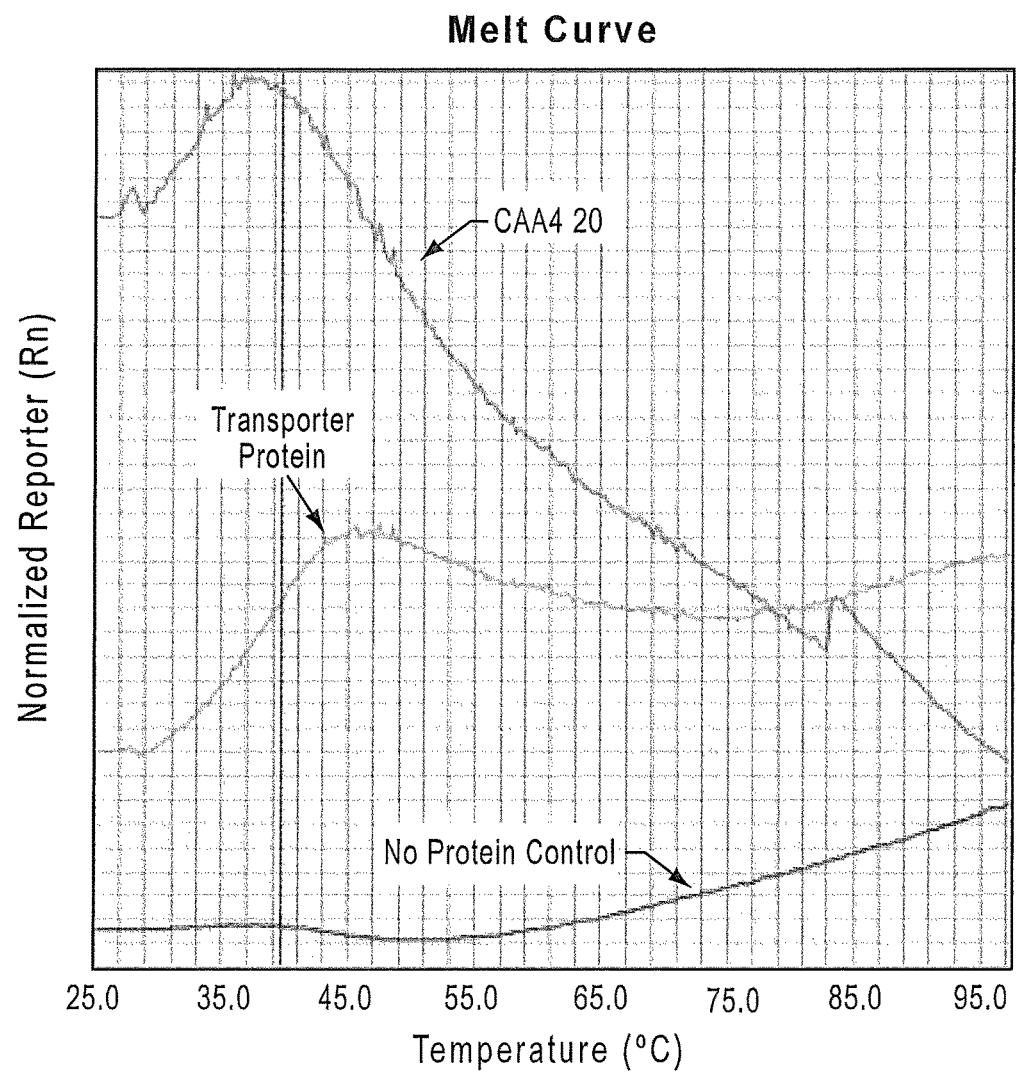

FIGS. 6A and 6B show the effect of two different filters, X5-M5 (FIG. 6A) and M4-X4 (FIG. 6B) on melt curves obtained for Human Plasma. In FIG. 8A, the melt curve of human plasma using X5-M5 filter is shown in combination with either SYPRO® Orange or SYPRO® Red. The combination of SYPRO® Red with an X5-M5 filter provides a much more informative melt curve (FIG. 6A), than that of SYPRO® Orange and X5-M5 filter (FIG. 6A, lower curve at left) or SYPRO® Orange and X4-M4 filter (FIG. 6B). This is more effectively seen in the first derivative graphs FIG. 6C (first derivative of FIG. 6A.) and FIG. 6D (first derivative of FIG. 6B). An abundance of unfolding phenomena is clearly visible using SYPRO® Red with an X5-M5 filter.

Example 7: PTS of Human Plasma Using Fluorescent Dye Mixtures

In Example 7, PTS is performed on blood plasma using either a single fluorophore dye or a mixture of fluorophore dyes. The dyes used are SYPRO® Orange protein gel stain *5000× Concentrate in DMSO, 500 µl, Catalog#S6650 (% DMSO in 5000×=100%, 40×=0.8%, 10×=0.2%). SYPRO® Tangerine Orange protein gel stain *5000× Concentrate in DMSO, 500 µl, Catalog#S12010 (% DMSO in 5000×=100%, 40×=0.8%, 10×=0.2%). SYPRO® Red protein gel stain *5000× Concentrate in DMSO, 500 µl, Catalog#S6653 (% DMSO in 5000×=100%, 40×=0.8%, 10×=0.2%). The dyes are prepared using the individual dyes directly from the tubes, the dye mixture is SYPRO® Orange+ SYPRO® Red+ SYPRO® Tangerine 10 µl each (in total 30 µl). The final % DMSO in the 20 µl reaction is 0.2%. The SYPRO® Orange is diluted in 100 mM Potassium Phosphate buffer, pH 7.0, 150 mM NaCl 1:125 (40×) and 2.5 µl is added to the mix. The final concentration in the protein melt reaction is 10×. The PTS thermal melt reaction mixes are formulated as shown in Table 10.

TABLE 10

Protein Thermal Melt mix.

| | 1X | 4X |
|---|---|---|
| 4X Protein Melt Test buffer C4 | 5 µl | 20 µl |
| 40X Protein Melt Dye Mixture; final Concentration is 10X in 20 µl | 5 µl | 20 µl |
| H₂O | 7 µl | 28 µl |
| Protein in Plasma | 3 µl | 12 µl |
| Total | 20 µl | 80 µl |

4×PTS reactions are prepared without dye—PTS buffer, protein and water only. 15 µl of the appropriate mixture is aliquoted into each well of a 96 well plate. 51 µl of 40× dye and dye mixture is added per well. Each well is mixed by pipetting up and down four times. The plate is immediately loaded onto the plate in the instrument after a 1 min centrifugation @1000 rpm.

Figure 7:
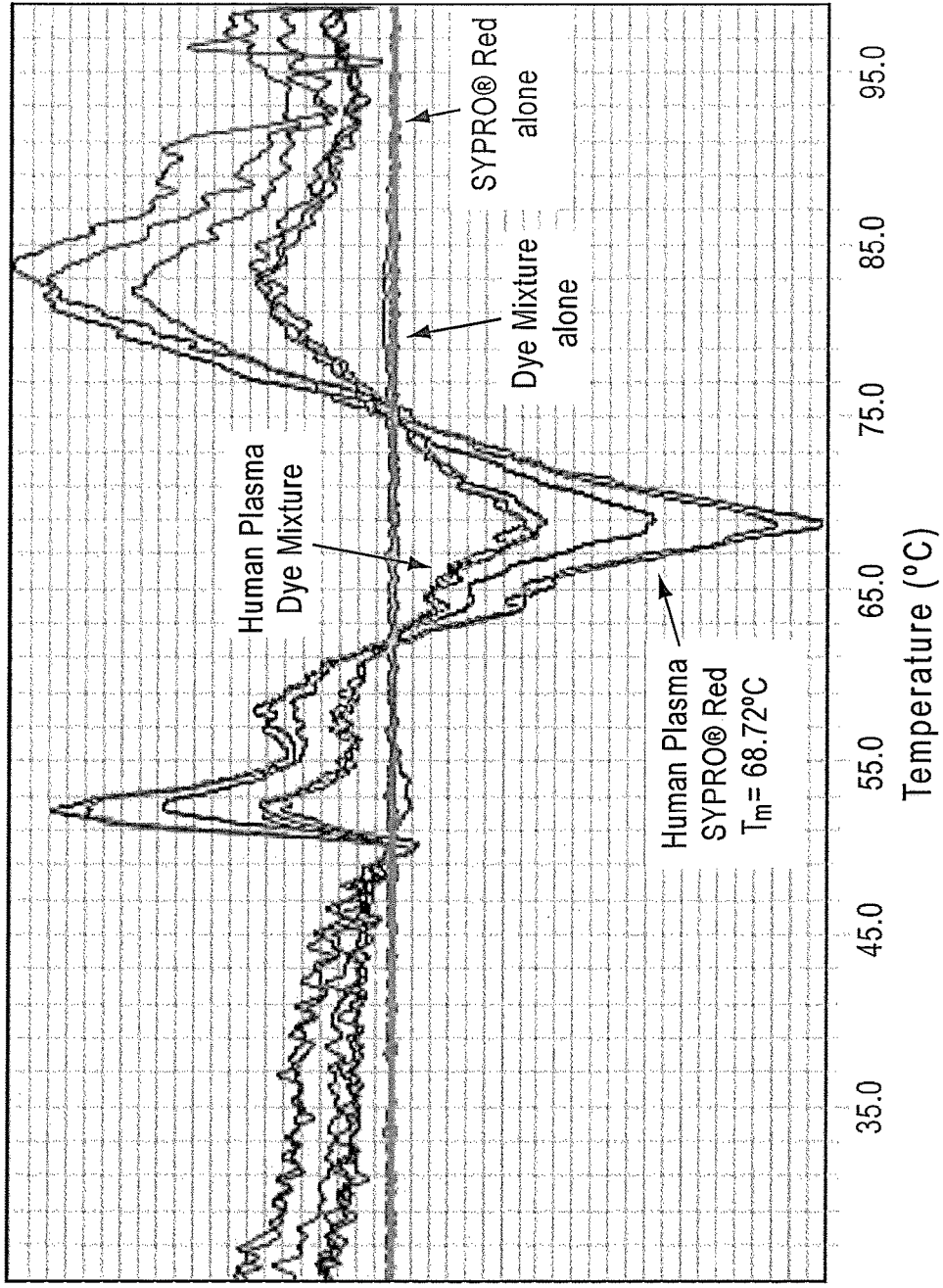
FIG. 7 shows PTS curves of human plasma, dyes, and plasma-dye combinations using an X5-M5 filter.

FIG. 7 shows the overlay of the first derivative graph of SYPRO® Red alone, dye mixture containing SYPRO® Orange+SYPRO® Red+SYPRO® Tangerine, plasma plus SYPRO® Red alone, and plasma plus the above dye mixture, in the presence of an X5-M5 filter.

Example 8: Identification of Best Dye Mixture for PTS of Membrane Proteins

PTS was performed on membrane proteins including a hydrophobic membrane transporter protein and CAA4 20)

(including a no protein control (NPC) using the following methods. The dye mixtures are prepared as shown in Table 6. 100 µl of each dye are prepared. Each of the membrane proteins is diluted in 50% glycerol, 1× buffer C3 (100 mM potassium phosphate, pH 7.0, 100 mM NaCl). The transporter is diluted 1:4; the CAA4 20 is diluted 1:2. The reactions are set up without the dye as follows: 1×=5 µl 4× buffer C3, 2 µl protein (10×=~2.5 mg/ml) and 12 µl water (total 19 µl/well). 20×=100 µl 4× buffer C3, 40 µl protein (10×=~2.5 mg/ml) and 240 µl water (total 19 µl/well). The reactions are mixed with gentle pipetting up and down. 20 µl of each reaction is aliquoted into each well as shown in the Plate Map of Table 11. 1 µl of each of the 16 dye formulations is added also according to Table 11, for a total of 48 wells (16 for each of the two membrane protein samples and 16 for the no protein control). The protein thermal shift experiment is performed using standard protocol using run time conditions as follows: a temperature hold at 20° C. for one minute followed by a thermal ramp of 0.05° C. with continuous data collection to 95° C., followed by a 1 minute hold at the final temperature.

TABLE 11

Plate map.

| Trans-porter | d.m. 9 | d.m. 10 | d.m. 11 | d.m. 12 | d.m. 13 | d.m. 14 | d.m. 15 | d.m. 16 |
|---|---|---|---|---|---|---|---|---|
| | d.m. 1 | d.m. 2 | d.m. 3 | d.m. 4 | d.m. 5 | d.m. 6 | d.m. 7 | d.m. 8 |
| CAA4 20 | d.m. 9 | d.m. 10 | d.m. 11 | d.m. 12 | d.m. 13 | d.m. 14 | d.m. 15 | d.m. 16 |
| | d.m. 1 | d.m. 2 | d.m. 3 | d.m. 4 | d.m. 5 | d.m. 6 | d.m. 7 | d.m. 8 |
| No protein control | d.m. 9 | d.m. 10 | d.m. 11 | d.m. 12 | d.m. 13 | d.m. 14 | d.m. 15 | d.m. 16 |
| | d.m. 1 | d.m. 2 | d.m. 3 | d.m. 4 | d.m. 5 | d.m. 6 | d.m. 7 | d.m. 8 | d.m. = dye mixture of Table 8.

Figure 8B:
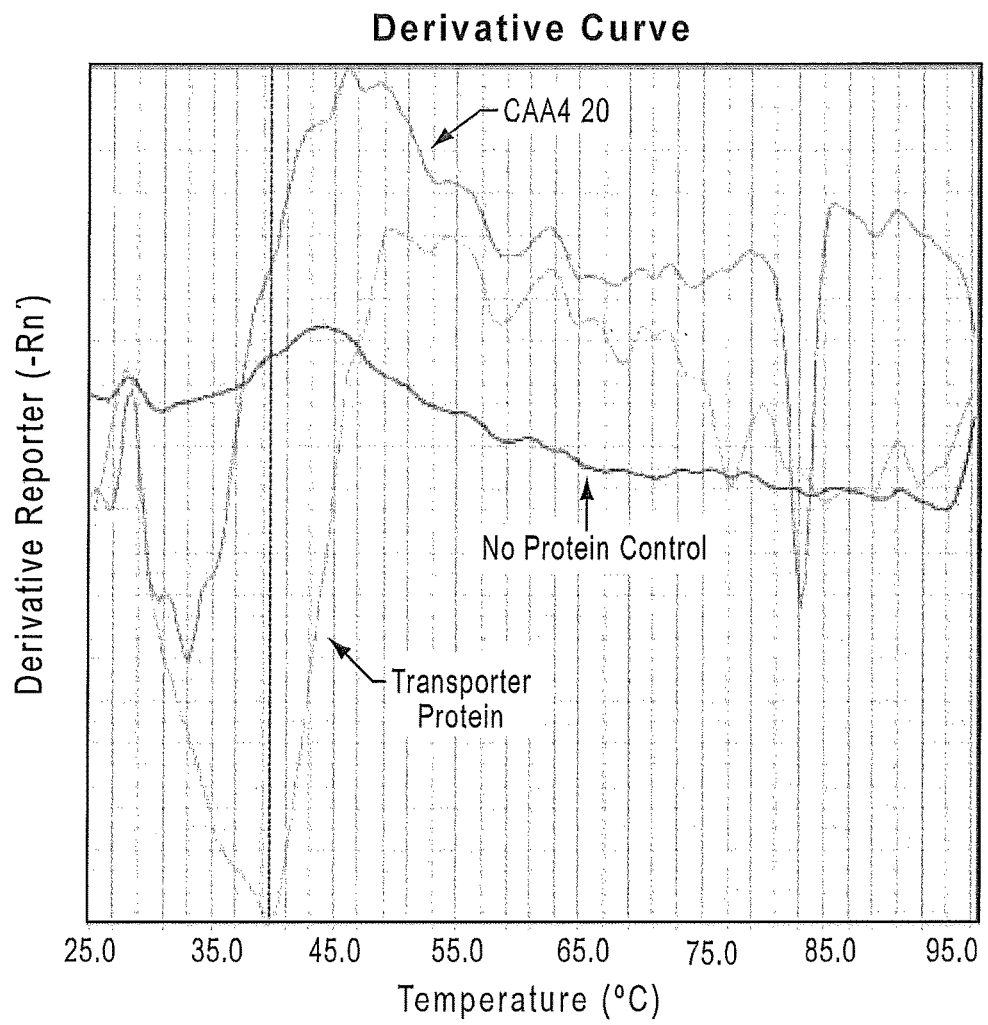
Figure 8C:
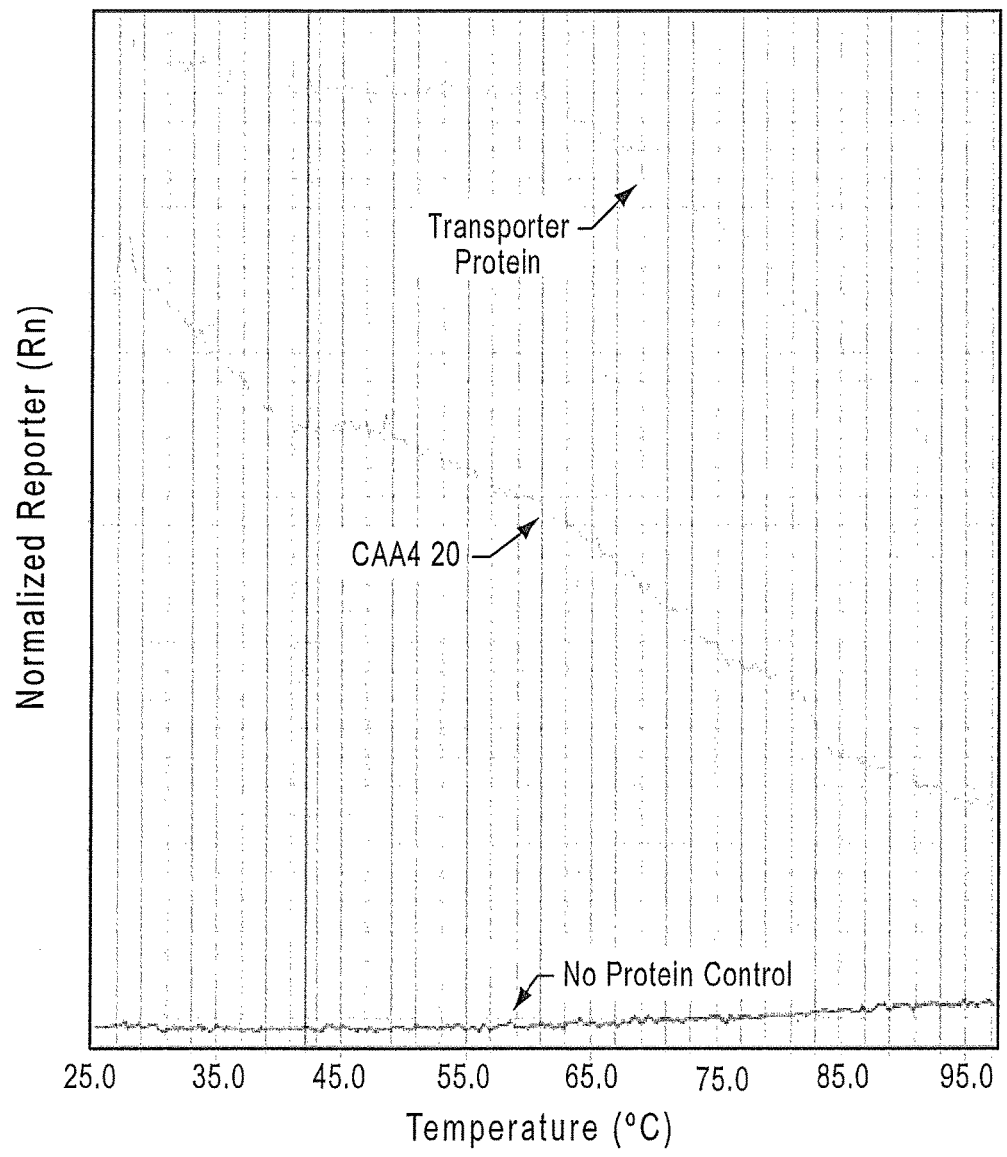
FIGS. 8C and 8D show the first derivative graphs for FIG. 6A and FIG. 6B respectively.
Figure 8D:
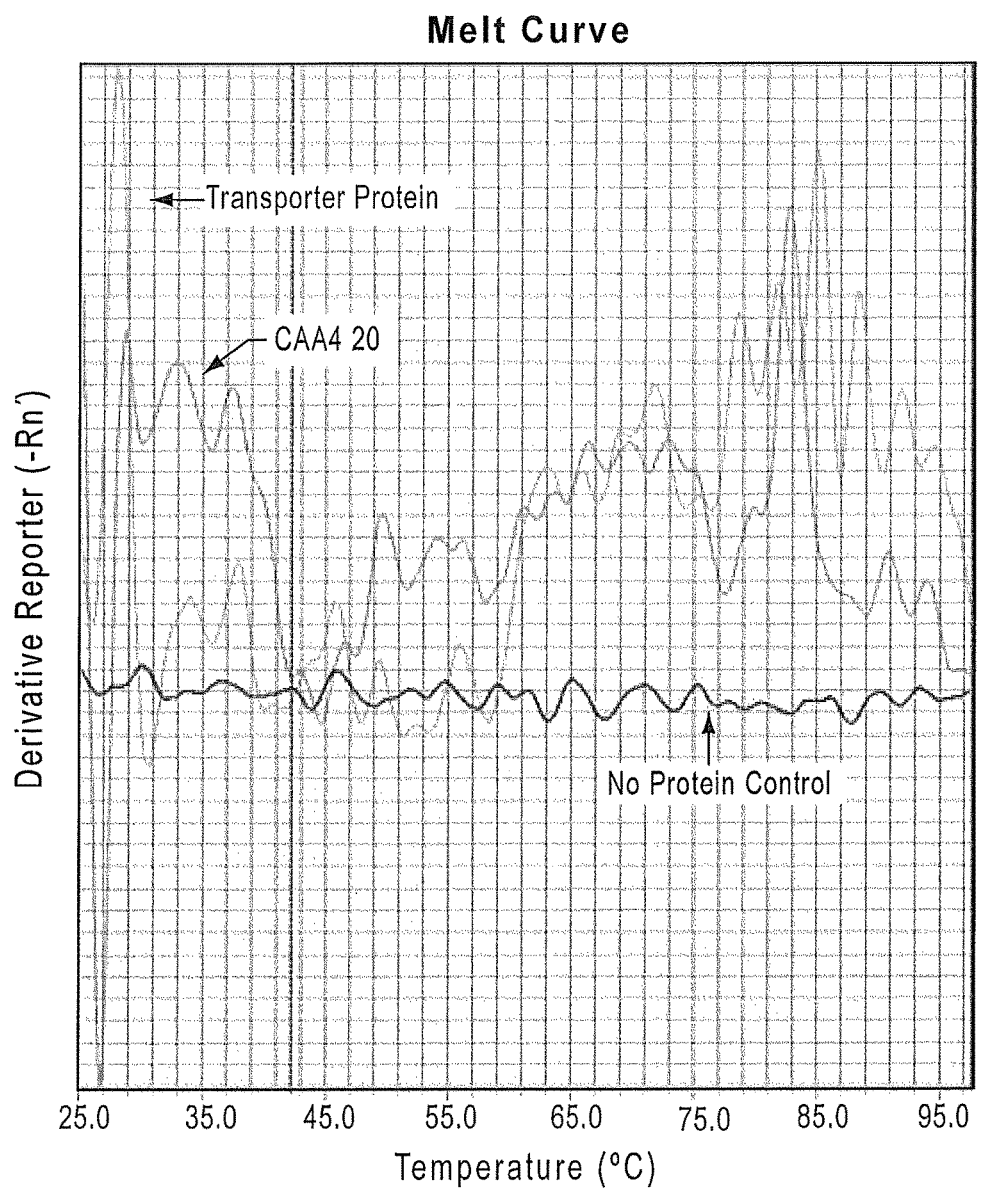

FIGS. 8A-B show PTS using a Nile Red and SYPRO® Orange mixture and FIGS. 8C-D show PTS of each membrane protein using SYPRO® Orange alone, both using an X4-M4 filter. The results demonstrate that the mixture of Nile Red and SYPRO® Orange yields the best PTS curve for the transporter and the CAA4 20 membrane proteins.

Figure 9A:
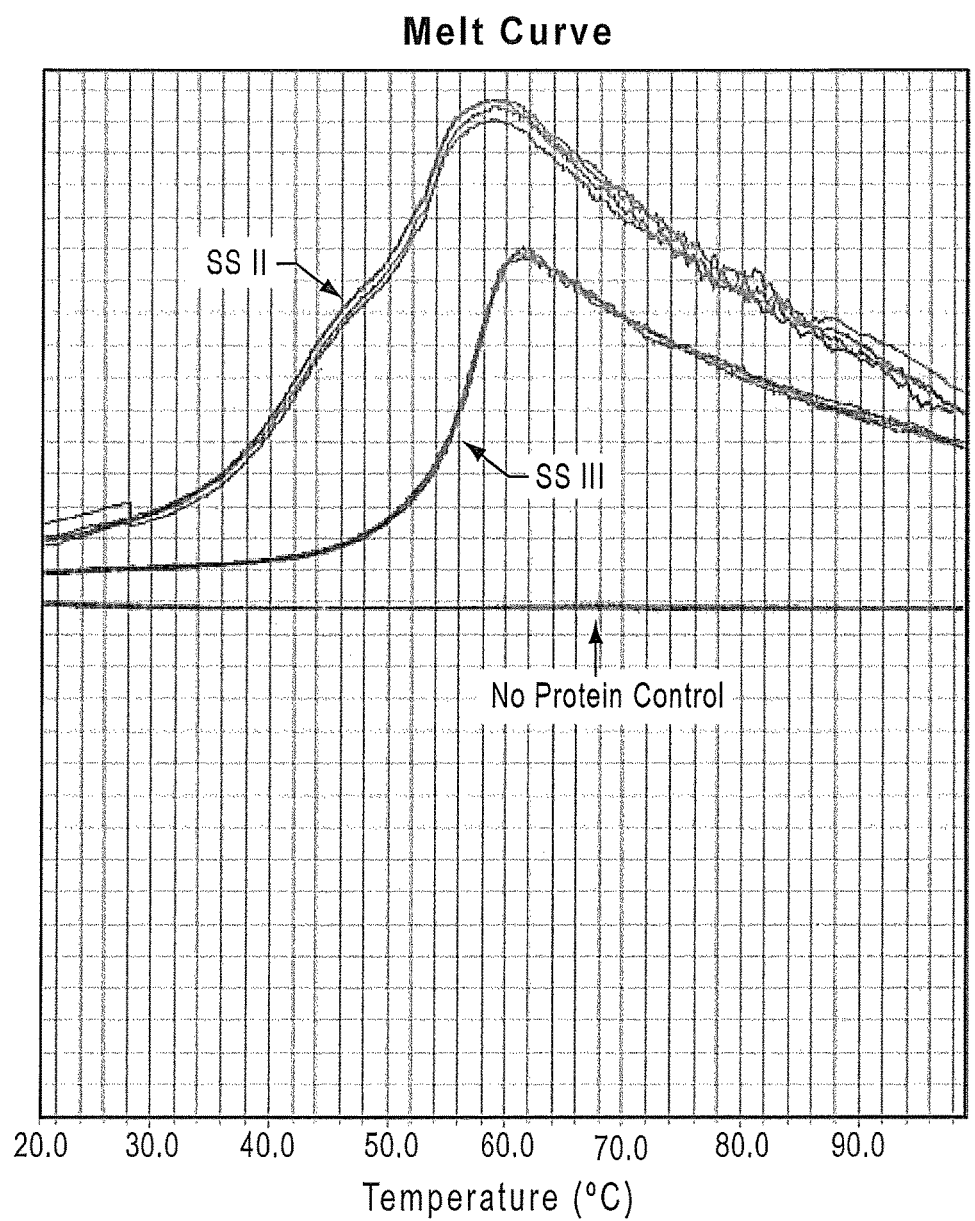
FIGS. 9A through 9D shows melt curves and the first derivative curves for SuperScript®II and SuperScript®III reverse transcriptase PTS using a variety of dyes, buffers and filters.
Figure 9B:
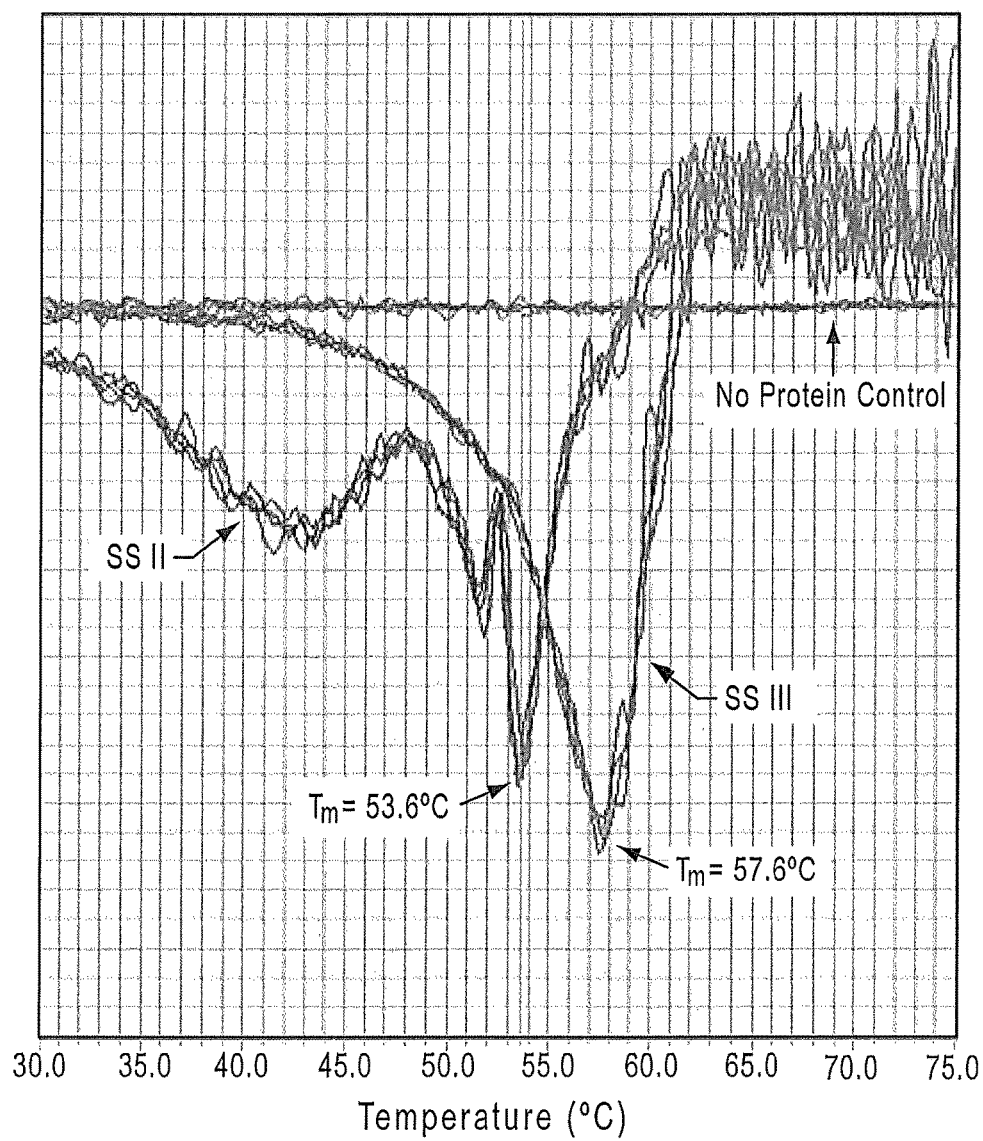
Figure 9C:
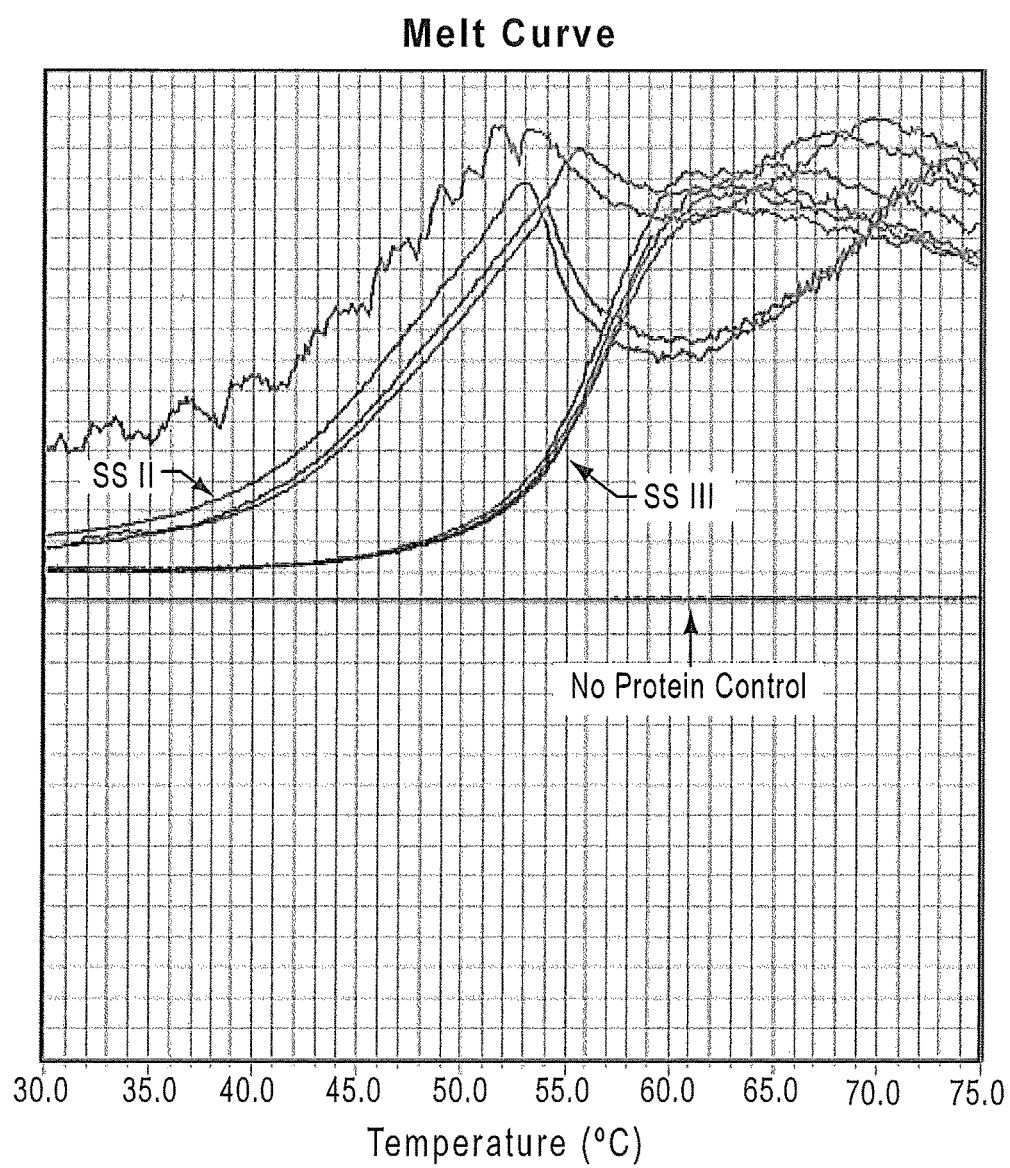
Figure 9D:
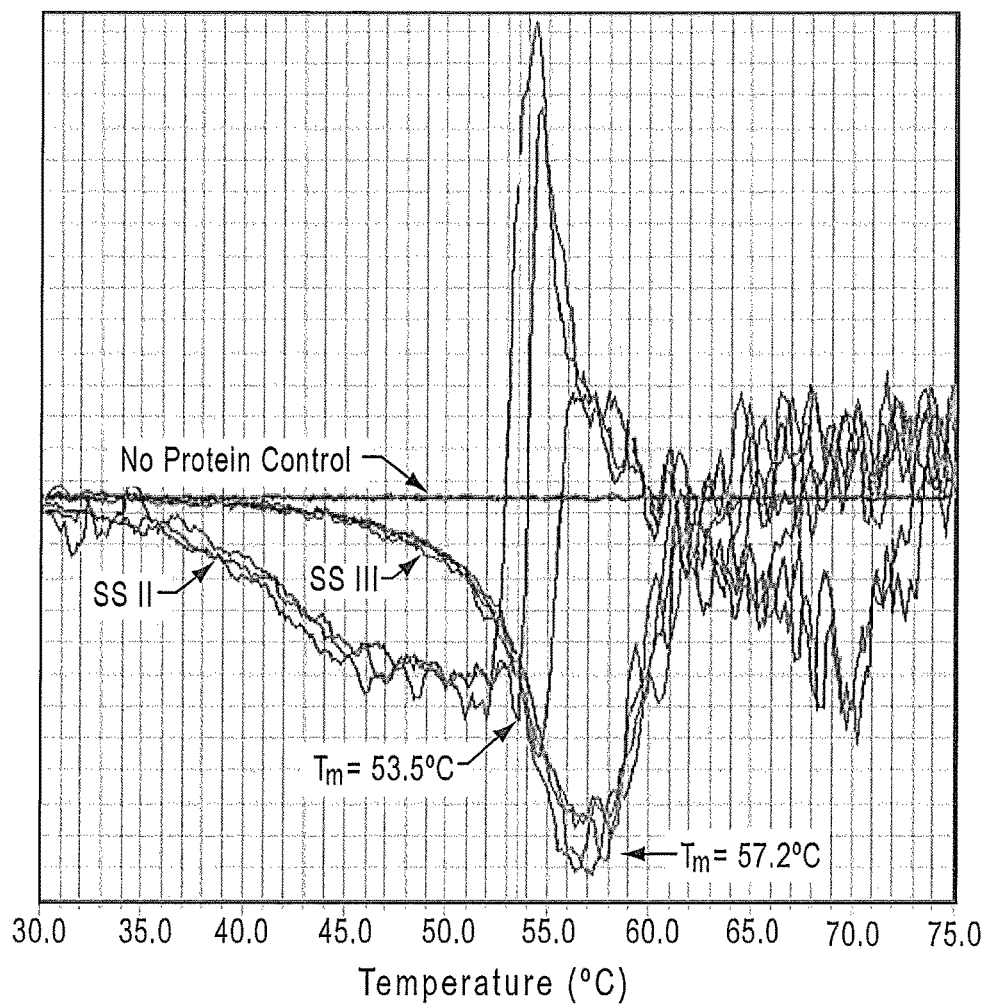

Example 9: Identification of Best Dye Mixture for SuperScript®II and SuperScript®III Reverse Transcriptases in PTS Assays PTS is performed on SuperScript®II (SSII) and SuperScript®III (SSIII) using reaction condition as described in Example 9 using buffer C3 or buffer E (of EXAMPLE 6). Each enzyme is prepared as a 10× solution (approx 3 mg/ml) and reaction wells containing either 14 µl (1×) or 238 µl (17×) of the enzyme are prepared, adding either 35 ul (1×) or 595 ul (17×) buffer. 1.4 µl of each of the 16 different 100× dye formulations is added according to Table 8. The thermal shift experiment is run as described in EXAMPLE 8. As shown in FIGS. 9A-D, a dye mixture of SYPRO® Orange, SYPRO® Red and SYPRO® Tangerine (Dye formulation 7) yields the best resolution of protein domain melting. FIGS. 9A through B show the results using an X5-M5 filter for buffer C3. $T_m$s of 56.6° C. and 57.6° C. in buffer C3 are identified in FIG. 9A for SSII and SSIII respectively. FIGS. 9C through D show the results using an X4-M4 filter and using SYPRO® Orange alone (Dye formulation 10) and buffer C3, where somewhat lower $T_m$s are observed. $T_m$s of 53.5° C. and 57.2° C. are found for SSII and SSIII, respectively.

Figure 10A:
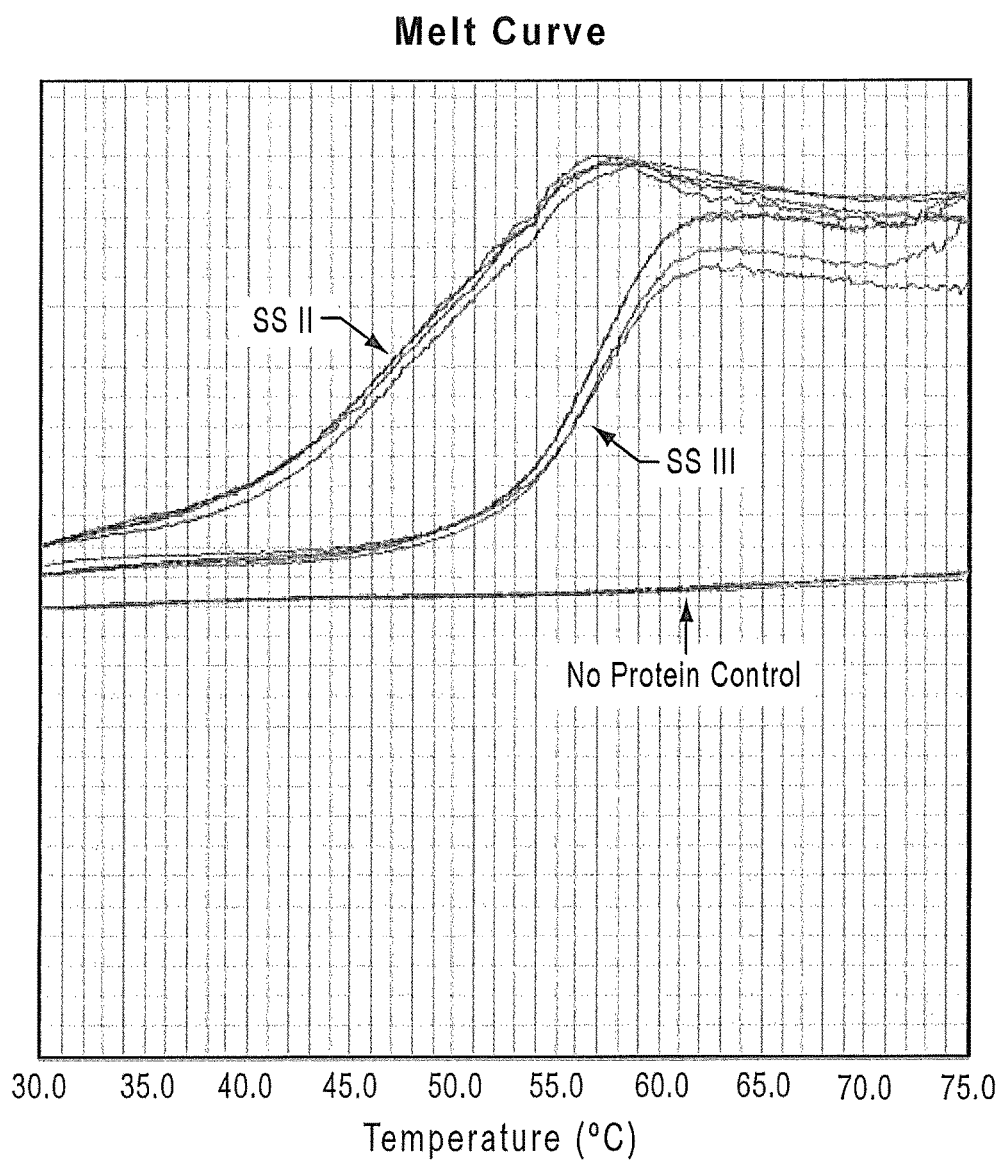
FIGS. 10A through 10B show PTS of SuperScript®II and SuperScript®III using a mixture of SYPRO® Orange and SYPRO® Red as compared to SYPRO® Orange alone, in the presence of an X4-M4 filter.
Figure 10B:
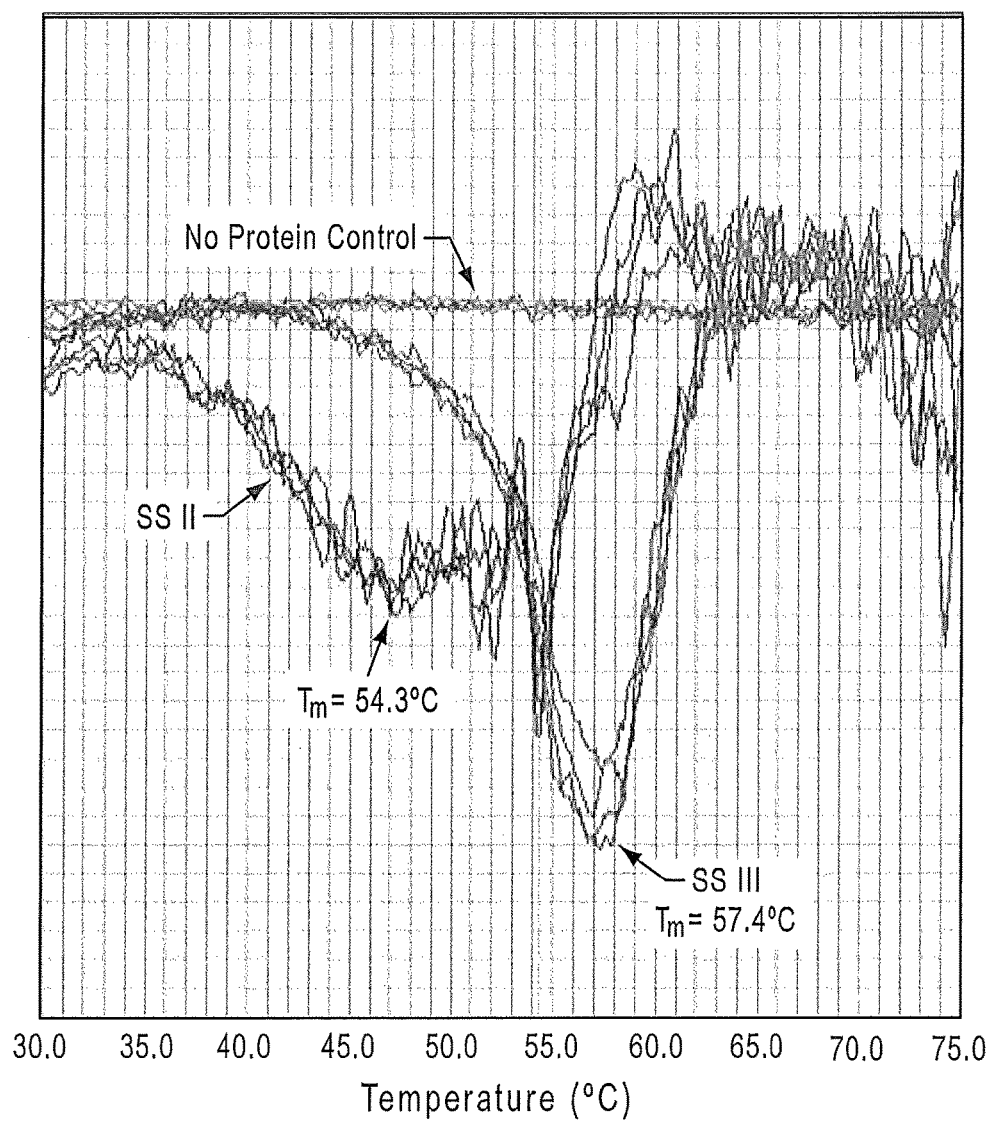

FIGS. 10A-B show the results for SSII and SSII using a mixture of Nile Red and SYPRO® Orange (dye formulation 15) in C3 buffer, which can be compared to SYPRO® Orange alone (FIGS. 9C-D). This dye mixture provides maximal resolution of the protein domain melting using an X4-M4 filter. $T_m$s of 54.3° C. and 57.4° C. are observed for SSII and SSIII.

Figure 11A:
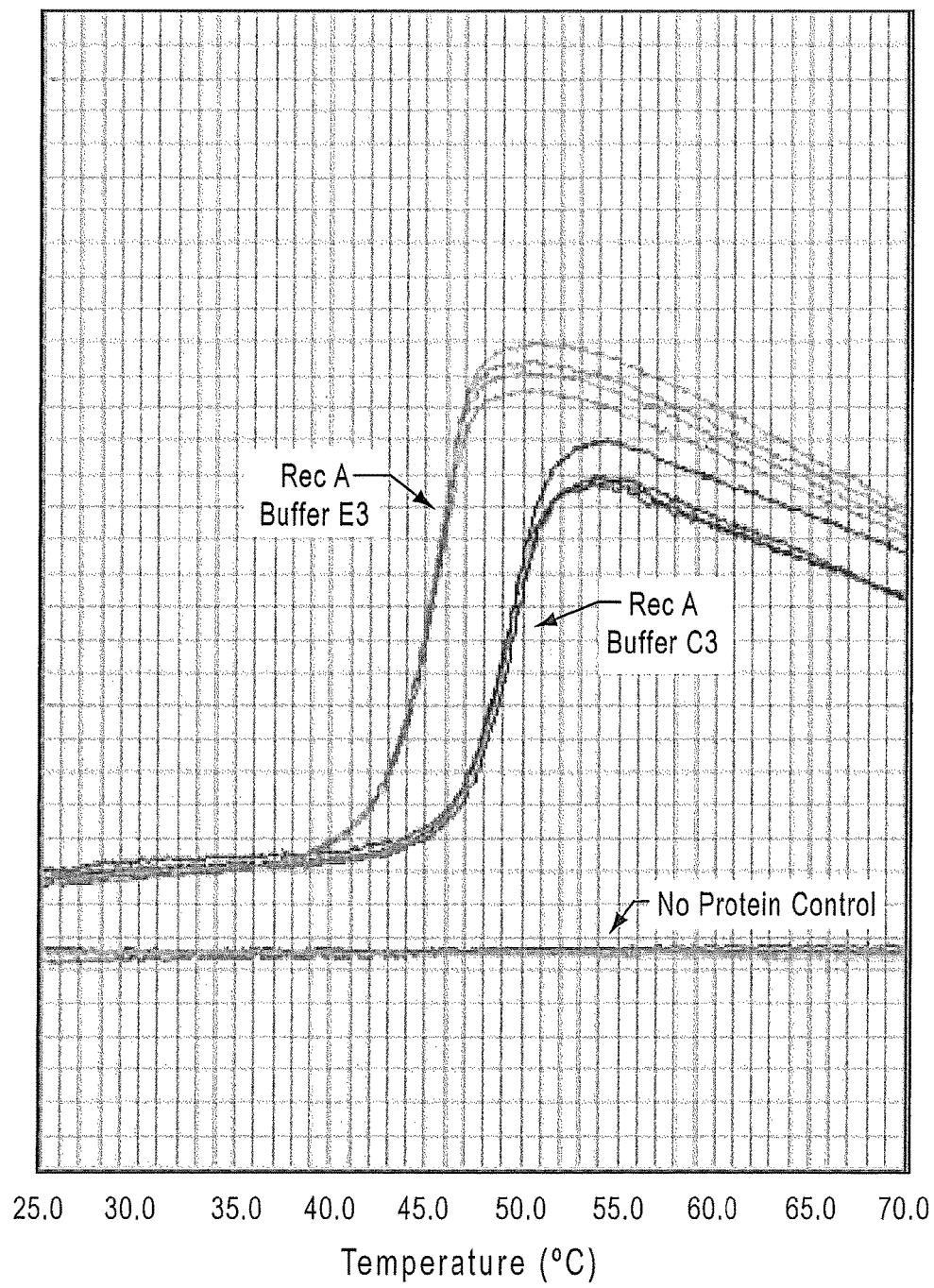
FIGS. 11A through 11D shows PTS of RecA DNA repair protein using a mixture of SYPRO® Orange, SYPRO® Tangerine and SYPRO® Red as compared to SYPRO® Orange alone.
Figure 11B:
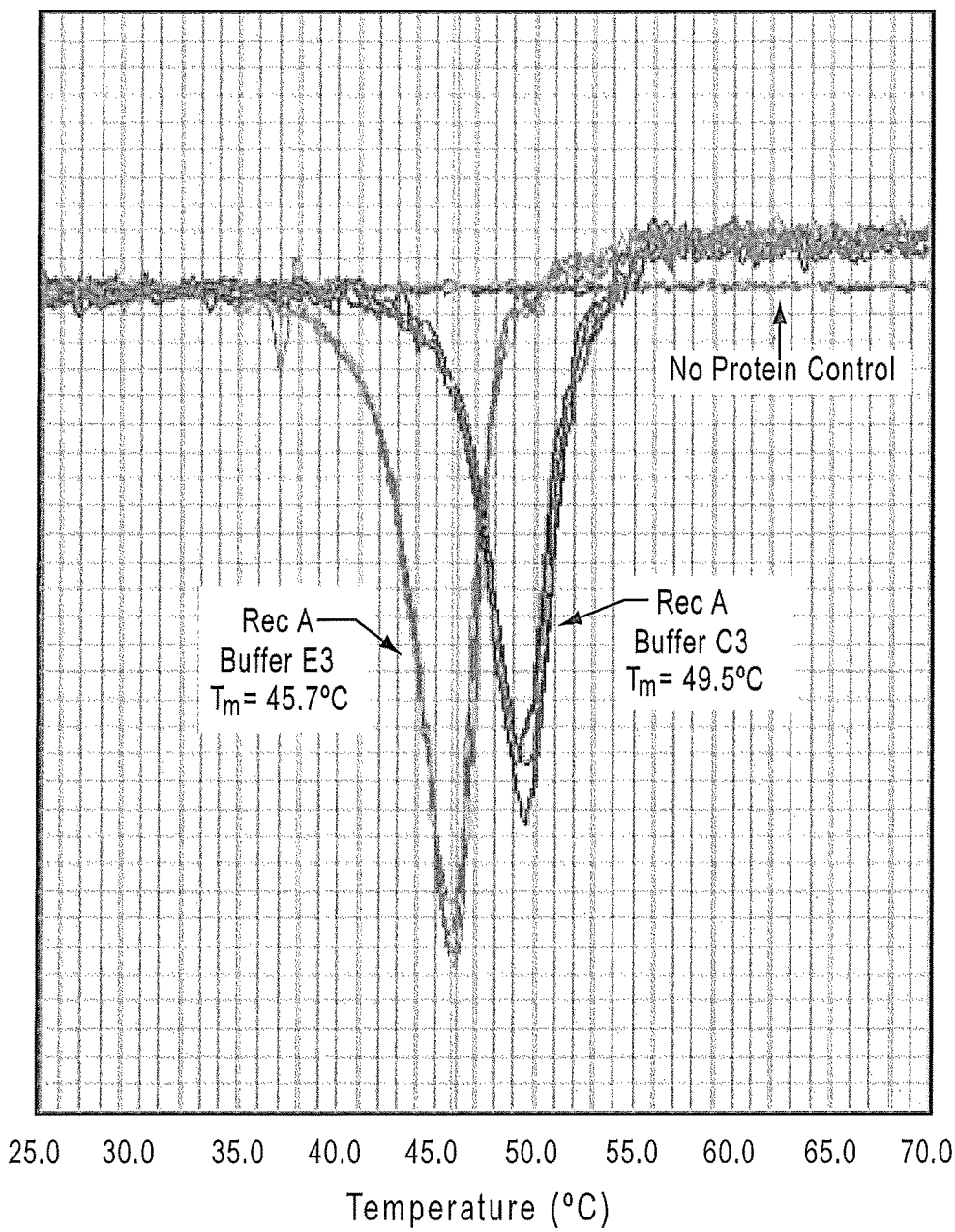
Figure 11C:
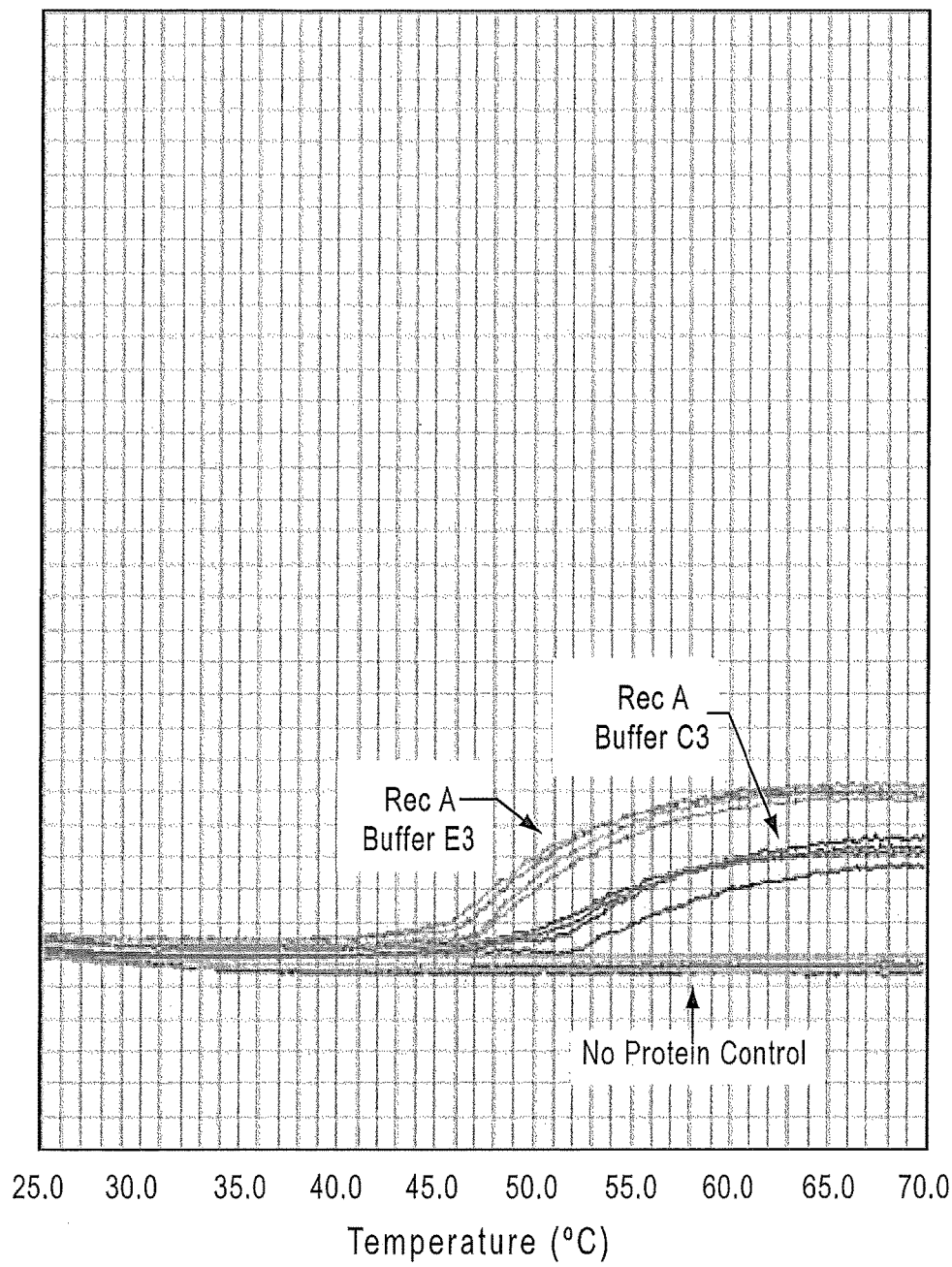
Figure 11D:
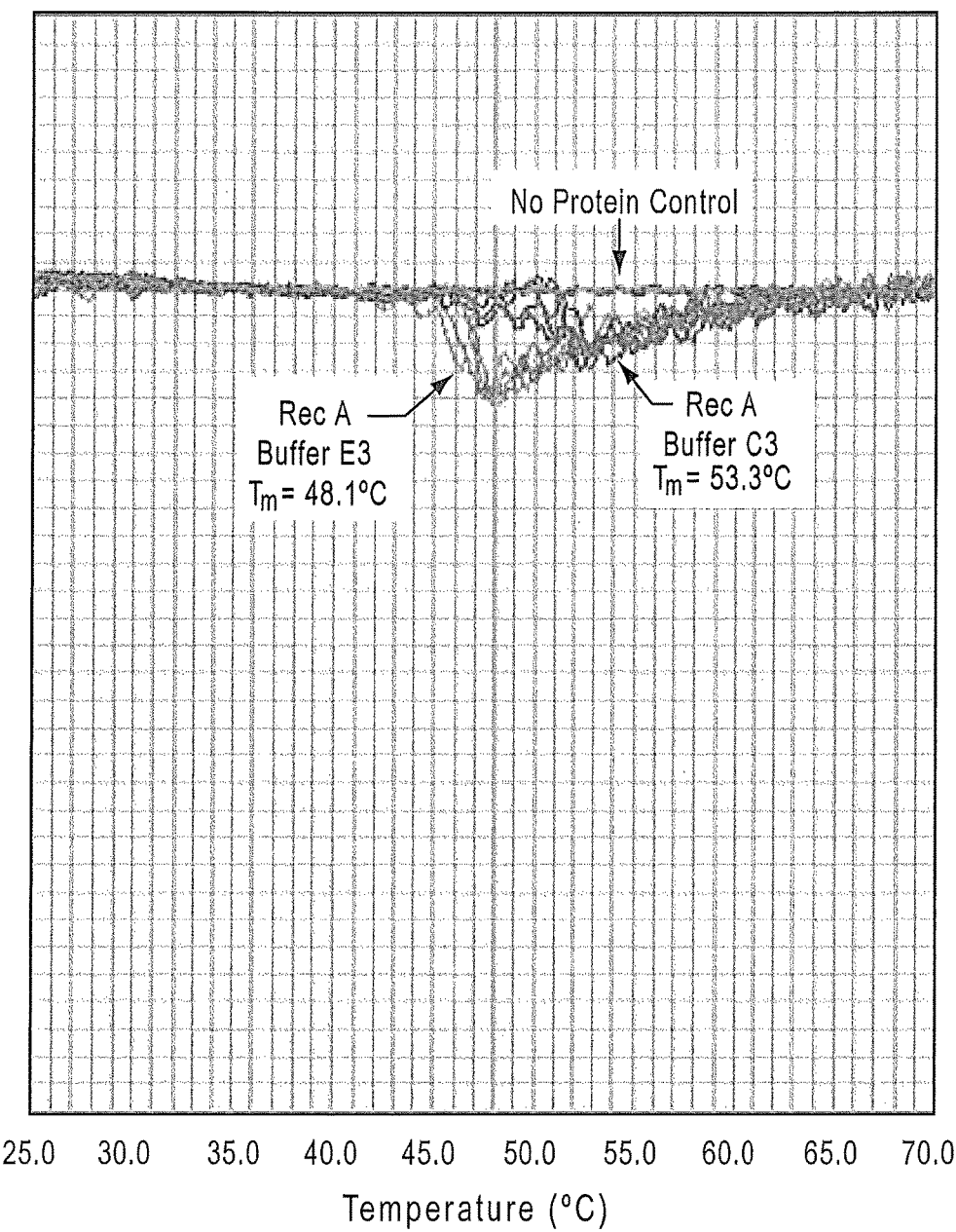
Figure 13A:
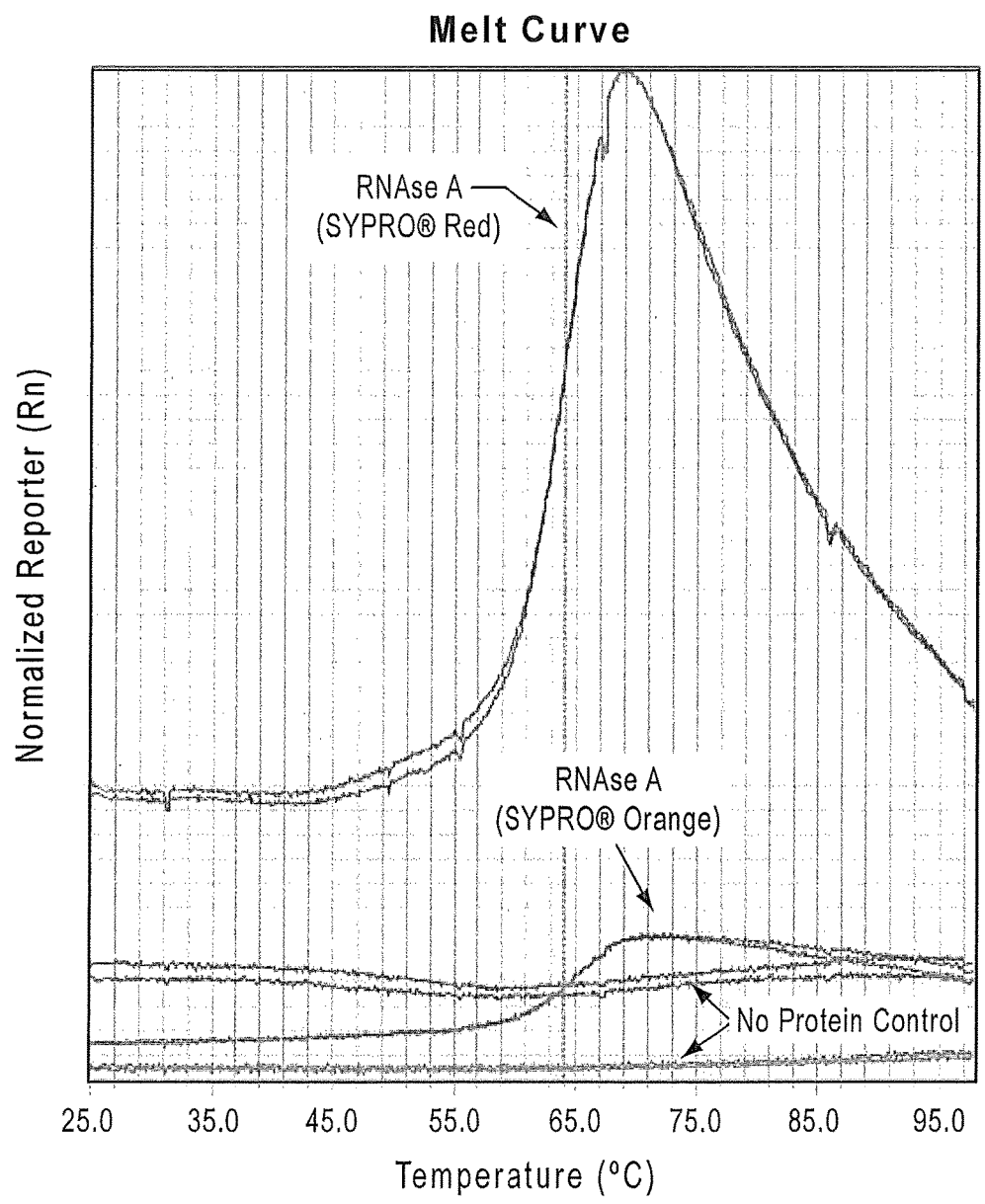
FIGS. 13A through 13B show PTS of RNAse A using SYPRO® Red versus SYPRO® Orange.
Figure 13B:
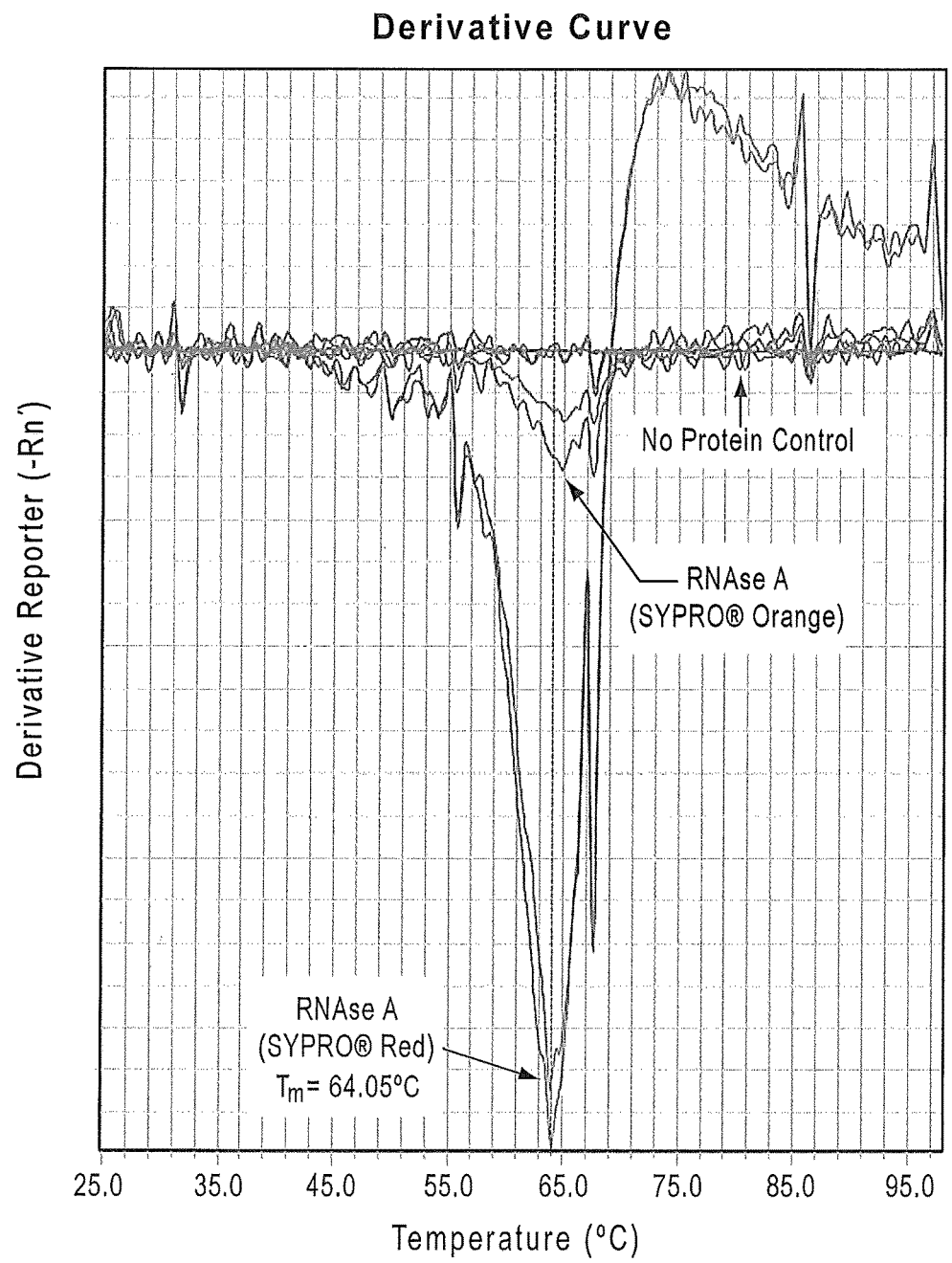

Example 10: Identification of Best Dye Mixture for RecA DNA Repair Protein in PTS PTS is performed on RecA, using conditions as is discussed in Example 6. 1.4 µl of each of the 100× dye formulations is added according to Table 9. PTS reproducibility is improved with dye formulation 7 (SYPRO® Orange, SYPRO® Red and SYPRO® Tangerine) (FIGS. 13A and 13B) using an X5-M5 filter relative to SYPRO® Orange alone using an X4-M4 filter (FIGS. 13C and 13D). In FIG. 13A, using the mixture of dyes (formulation 7), the two melt curves shown are for RecA in E3 and C3 buffer, respectively. $T_m$s of 49.5° C. and 45.7° C. are identified for RecA in Buffer C3 and RecA in Buffer E3 respectively, as shown in FIG. 11B. FIG. 11C shows the melt curve for RecA in E3 and C3 buffer, overlaid, using SYPRO® Orange alone and an X4-M4 filter, $T_m$s of 53.3° C. and 48.1° C. are identified for RecA in Buffer C3 and RecA in Buffer E3 respectively, as shown in FIG. 11D.

Example 11: Identification of Best Dye Mixture for PTS of Proteinase K

Figure 12A:
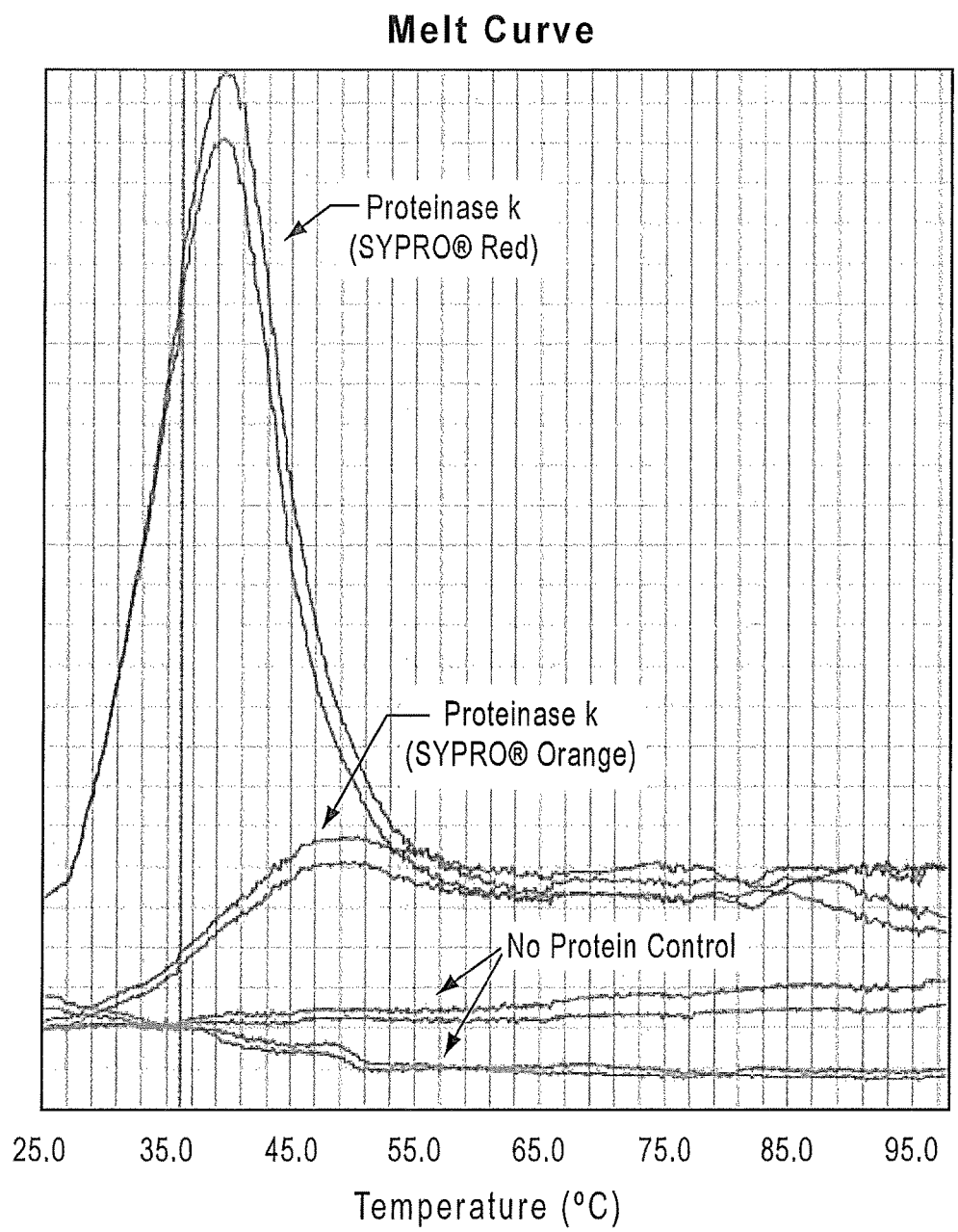
FIGS. 12A through 12B show PTS of T4 Proteinase K using SYPRO® Red versus SYPRO® Orange.
Figure 12B:
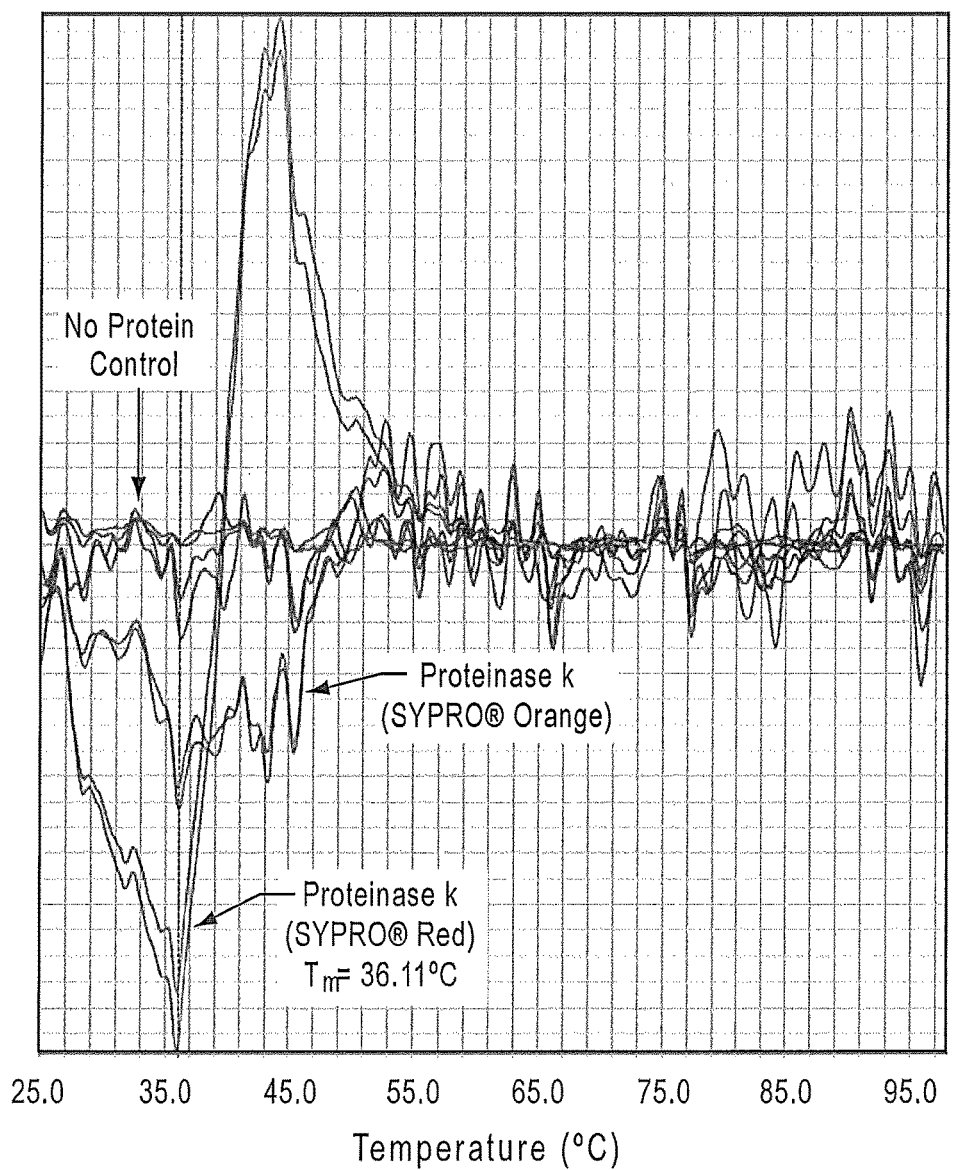

PTS is performed on Proteinase K as discussed in Example 6. 1.4 µl of each of the 100× dye formulations is added according to Table 8. As shown in FIG. 12A, the best results for Proteinase K is obtained using SYPRO® Red (FIG. 12A) as compared to the results using SYPRO® Orange, which are overlaid on the same curve. The amplitude of the signal from SYPRO® Red is much increased relative to that arising from SYPRO® Orange. The background was also higher with SYPRO® Orange as shown in FIG. 12B (the derivative plot). The X4-M4 filter was used in FIGS. 12A-B.

Example 12: Identification of Best Dye for PTS of RNAse A

PTS is performed on RNAse A as discussed in Example 6. 1.4 µl of the 100× dye mix is added according to Table 6. As shown in FIG. 13A, the best results are obtained using SYPRO® Red as compared to the results using SYPRO® Orange (lower curve in FIG. 13A). The background is also higher with SYPRO® Orange as shown in FIG. 15B (the derivative plot). The X5-M5 Filter is used in FIGS. 13A-B.

The optimal dye mixture varies, depending on the protein under examination. If proteins possess significant amounts of hydrophobic residues on the exterior of the folded protein, the use of a single dye like SYPRO® Orange may provide a high background to the melt curve. With proteins with multiphasic melts, clear differentiation may be possible, with optimized dye mixtures and filters, such as seen for SSII and SSIII.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. The teachings should not be read as limited to the described order or elements unless stated to that effect. It should be understood that various changes in form and detail may be made without departing from the scope of the present teachings, including the order and arrangement of disclosed method steps. Therefore, all embodiments that come within the scope and spirit of the present teachings and equivalents thereto are claimed.

What is claimed is:

1. A method of measuring stability of at least one protein under at least two different conditions, comprising:
   (a) under a first condition, forming a first sample solution mixture comprising the protein and at least two different fluorophore dyes, wherein at least one of the at least two different fluorophore dyes is selected from the group consisting of SYPRO Orange, SYPRO Red, and SYPRO Tangerine;
   (b) applying a controlled heating to the mixture wherein the protein undergoes unfolding;
   (c) measuring fluorescence emitted over a temperature range; and
   (d) calculating a first Tm value of the at least one protein under the first condition using the measured fluorescence from step (c);
   (e) repeating steps (a) through (d), using a second sample solution mixture comprising the protein and the fluorophore dyes selected for calculating the first Tm value, to calculate a second Tm value of the at least one protein under a second condition; and
   (f) comparing the first Tm value with the second Tm value of the same protein under the first condition and the second condition, respectively, thereby measuring the stability of the at least one protein under at least two different conditions.

2. The method of claim 1, wherein the first and second sample solution mixtures are formed when the at least one protein is in its native state.

3. The method of claim 2, wherein when the at least one protein is present in its native state, then each of the at least two different fluorophore dyes is configured to provide at least a minimally fluorescent signal and when the at least one protein is present in an unfolded state, then each of the at least two different fluorophore dyes is configured to provide a substantially increased fluorescent signal.

4. The method of claim 1, wherein the measuring step is performed in the presence of a filter.

5. The method of claim 1, wherein each of the at least two different fluorophore dyes are spectrally distinct.

6. The method of claim 1, wherein one of the at least two different fluorophore dyes is 9-diethylamino-5H-benzo[a]phenoxazine-5-one (Nile Red).

7. The method of claim 1, wherein the second sample solution mixture further comprises a ligand which is configured to form a protein/ligand complex with the at least one protein.

8. The method of claim 7, wherein the protein/ligand complex is an antibody/antigen complex.

9. The method of claim 7, wherein the ligand is a peptide, a polynucleotide, or an aptamer.

10. The method of claim 7, wherein the method comprises the steps of:
    (e) performing the steps (a)-(c) wherein the sample solution mixture contains only the at least one protein;
    (f) calculating the first $T_m$ value of the at least one protein using the measured fluorescence;
    (g) performing the steps (a)-(c) wherein the sample solution mixture contains the at least one protein and a ligand in a protein/ligand complex;
    (h) calculating the second $T_m$ value of the at least one protein and the ligand using the measured fluorescence of step (g); and
    (i) comparing the first $T_m$ value obtained in step (f) and the second $T_m$ value obtained in step (h); and
    (j) thereby measuring the change in stability upon forming the protein/ligand complex with the at least one protein.

11. The method of claim 1, wherein the controlled heating is a thermal ramp.

12. The method of claim 1, wherein the first and second sample solution mixtures further comprise a buffer.

13. The method of claim 1, wherein the first and second sample solution mixtures further comprise a surfactant.

14. The method of claim 1, wherein the first and second sample solution mixtures further comprise a polyol.

15. The method of claim 12,
    wherein the first sample solution mixture comprises a first buffer,
    and the second sample solution mixture comprises a second buffer, and
    comparing the first $T_m$ value and the second $T_m$ value, thereby measuring the stability of the at least one protein in the presence of the first buffer compared to the stability of the at least one protein in the presence of the second buffer.

16. The method of claim 1, wherein the at least two different flurophore dyes comprise one of the following combinations:
    1) 9-diethylamino-5H-benzo[a]phenoxazine-5-one (Nile Red) and SYPRO Orange;
    2) 9-diethylamino-5H-benzo[a]phenoxazine-5-one (Nile Red) and SYPRO Red;
    4) 9-diethylamino-5H-benzo[a]phenoxazine-5-one (Nile Red) and SYPRO Tangerine;
    5) SYPRO Orange, SYPRO Red, and SYPRO Tangerine.

17. The method of claim 1, wherein the first sample solution mixture and/or the second sample solution mixture further comprises one or more reagents selected from a surfactant, a polyol or a buffer.

18. The method of claim 1 wherein the protein is a membrane protein, a transporter protein, or an enzyme.

19. The method of claim 1, wherein the first and second sample solution mixtures have an assay volume of 1 pl to 5 pl.

20. The method of claim 19, wherein about 1 mg of the protein can be used to conduct $10^3$-$10^4$ of reactions in a miniaturized format.

21. The method of claim 20 performed on a high density microplate assay array.

22. The method of claim 1, wherein the protein used in the first sample solution mixture is a wild type protein and the protein used in the second sample solution mixture is a mutated version of the protein.

* * * * *